(12) United States Patent
Dabideen et al.

(10) Patent No.: US 9,029,532 B2
(45) Date of Patent: May 12, 2015

(54) 5,6-RING-SUBSTITUTED NAPHTHOPYRAN COMPOUNDS

(71) Applicant: Transitions Optical, Inc., Pinellas Park, FL (US)

(72) Inventors: Darrin R. Dabideen, Pittsburgh, PA (US); Meng He, Murrysville, PA (US); Anil Kumar, Murrysville, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 214 days.

(21) Appl. No.: 13/792,345

(22) Filed: Mar. 11, 2013

(65) Prior Publication Data

US 2014/0256935 A1   Sep. 11, 2014

(51) Int. Cl.
*C07D 493/04* (2006.01)
*G02B 1/04* (2006.01)
*G03C 1/73* (2006.01)

(52) U.S. Cl.
CPC ................ *G02B 1/04* (2013.01); *C07D 493/04* (2013.01); *G03C 1/73* (2013.01)

(58) Field of Classification Search
CPC ................................. G02B 1/04; C07D 493/04
USPC ......................................................... 544/150
See application file for complete search history.

(56) References Cited

U.S. PATENT DOCUMENTS

| | | | |
|---|---|---|---|
| 5,658,501 | A | 8/1997 | Kumar et al. |
| 6,022,497 | A | 2/2000 | Kumar |
| 6,153,126 | A | 11/2000 | Kumar |
| 6,348,604 | B1 | 2/2002 | Nelson et al. |
| 6,353,102 | B1 | 3/2002 | Kumar |
| 6,719,925 | B1 | 4/2004 | Breyne et al. |
| 7,459,555 | B2 | 12/2008 | Melzig et al. |

FOREIGN PATENT DOCUMENTS

| | | |
|---|---|---|
| WO | 9527914 A1 | 10/1995 |
| WO | 9920619 A1 | 4/1999 |
| WO | 9920629 A1 | 4/1999 |

*Primary Examiner* — Rebecca Anderson
(74) *Attorney, Agent, or Firm* — The Webb Law Firm

(57) ABSTRACT

The present invention relates to naphthopyran compounds that include at least one compound represented by the following Formulas (I), (II), and (III):

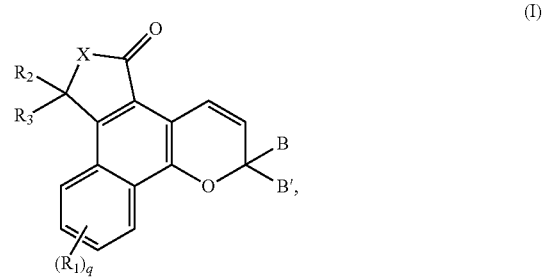

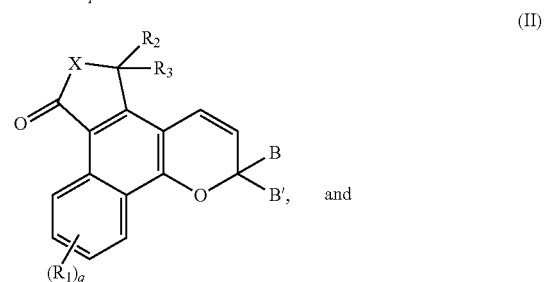

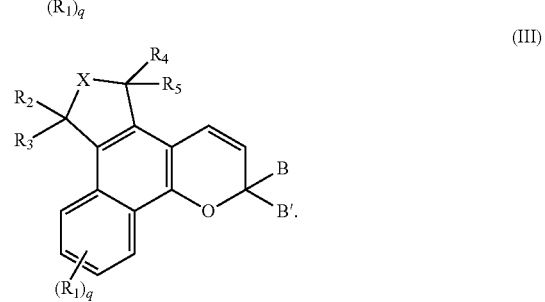

With reference to Formulas (I), (II), and (III), there is the proviso that: (i) at least one $R_1$ is a group L; and/or (ii) B and/or B' is substituted with at least one group L. The group L can be described as a lengthening group. The present invention also relates to photochromic-dichroic naphthopyran compounds and photochromic-dichroic articles containing such compounds.

11 Claims, 8 Drawing Sheets

Scheme 1

Scheme 2

Scheme 3

Scheme 4

Scheme 5

Scheme 6

Scheme 7

5,6-RING-SUBSTITUTED NAPHTHOPYRAN COMPOUNDS

FIELD

The present invention relates to 5,6-ring-substituted naphthopyran compounds that include at least one chiral or achiral group bonded thereto, and articles, such as photochromic-dichroic articles, that include such compounds.

BACKGROUND

Conventional linearly polarizing elements, such as linearly polarizing lenses for sunglasses and linearly polarizing filters, are typically formed from stretched polymer sheets containing a dichroic material, such as a dichroic dye. Consequently, conventional linearly polarizing elements are static elements having a single, linearly polarizing state. Accordingly, when a conventional linearly polarizing element is exposed to either randomly polarized radiation or reflected radiation of the appropriate wavelength, some percentage of the radiation transmitted through the element will be linearly polarized.

In addition, conventional linearly polarizing elements are typically tinted. Typically, conventional linearly polarizing elements contain a coloring agent and have an absorption spectrum that does not vary in response to actinic radiation. The color of the conventional linearly polarizing element will depend upon the coloring agent used to form the element, and most commonly, is a neutral color (for example, brown or gray). Thus, while conventional linearly polarizing elements are useful in reducing reflected light glare, because of their tint, they are typically not well suited for use under low-light conditions.

Conventional linearly polarizing elements are typically formed using sheets of stretched polymer films containing a dichroic material. Correspondingly, while dichroic materials are capable of preferentially absorbing one of two orthogonal plane polarized components of transmitted radiation, if the molecules of the dichroic material are not suitably positioned or arranged, no net linear polarization of transmitted radiation will be achieved. Without intending to be bound by any theory it is believed that due to the random positioning of the molecules of the dichroic material, selective absorption by the individual molecules will cancel each other such that no net or overall linear polarizing effect is achieved. As such, it is typically necessary to position or arrange the molecules of the dichroic material by alignment with another material so as to achieve a net linear polarization.

A common method of aligning the molecules of a dichroic dye involves heating a sheet or layer of polyvinyl alcohol ("PVA") to soften the PVA and then stretching the sheet to orient the PVA polymer chains. Thereafter, the dichroic dye is impregnated into the stretched sheet, and the impregnated dye molecules adopt the orientation of the polymer chains. Resultantly, at least some of the dye molecules become aligned, such that the long axis of each aligned dye molecule is generally parallel to the oriented polymer chains. Alternatively, the dichroic dye can be first impregnated into the PVA sheet, and thereafter the sheet can be heated and stretched as described above to orient the PVA polymer chains and associated dye. In this manner, the molecules of the dichroic dye can be suitably positioned or arranged amongst the oriented polymer chains of the PVA sheet, and a net linear polarization can be correspondingly achieved. As a result, the PVA sheet can be made to linearly polarize transmitted radiation, and correspondingly a linearly polarizing filter can thus be formed.

In contrast to the dichroic elements discussed above, conventional photochromic elements, such as photochromic lenses that are formed using conventional thermally reversible photochromic materials are generally capable of converting from a first state, for example a "clear state," to a second state, for example a "colored state," in response to actinic radiation, and reverting back to the first state in response to thermal energy. Thus, conventional photochromic elements are generally well suited for use in both low-light and elevated-light (or bright) conditions. Conventional photochromic elements, however, that do not include linearly polarizing filters are generally not capable of linearly polarizing incident radiation, such as direct or reflected light. The dichroic ratio of conventional photochromic elements, in either state, is generally less than two. Therefore, conventional photochromic elements are not capable of reducing reflected light glare to the same extent as conventional linearly polarizing elements. In addition, conventional photochromic elements have a limited ability to store or display information.

Photochromic-dichroic compounds and materials have been developed that provide both photochromic properties and dichroic properties, if properly and at least sufficiently aligned. Photochromic-dichroic compounds can be aligned in accordance with the stretching methods described above with regard to dichroic dyes, and/or other methods, such as electromagnetic alignment methods. Some current photochromic-dichroic compounds, however, can be subject to reduced stability. For example, some current photochromic-dichroic compounds can have poor fatigue resistance. Photochromic-dichroic compounds and materials having reduced fatigue resistance typically will exhibit a reduced or degraded photochromic response after extended exposure to actinic radiation. A reduced or degraded photochromic response can involve an undesirable increase in the amount of time required for the photochromic-dichroic compound or material to transition between a first state and a second state, such as from a colored state to a non-colored state, and visa versa.

It would be desirable to develop new photochromic-dichroic compounds that provide a desirable combination of photochromic properties and dichroic properties. In would be further desirable that such newly developed photochromic-dichroic compounds also posses improved stability, such as improved fatigue resistance.

SUMMARY

In accordance with the present invention, there is provided a naphthopyran compound comprising at least one compound represented by the following Formula (I), Formula (II), and Formula (III),

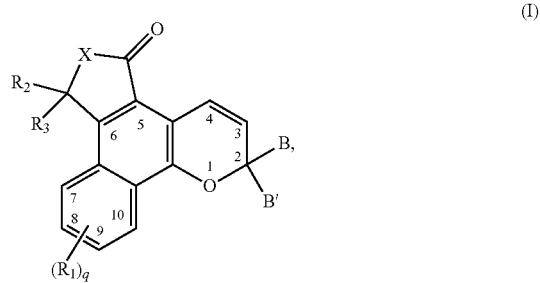

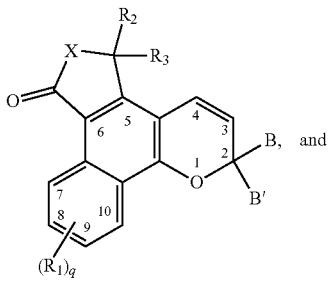

(II)

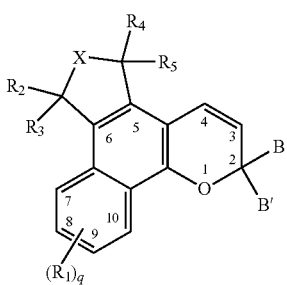

(III)

With reference to Formulas (I), (II), and (III): each X is independently selected from —O—, —S—, and —N(R$_6$)— where R$_6$ is selected from hydrogen, hydrocarbyl, and substituted hydrocarbyl; and each q is independently from 1 to 4.

With further reference to Formulas (I), (II), and (III), R$_1$ for each q is independently selected from: hydrogen, hydrocarbyl, and substituted hydrocarbyl each optionally and independently interrupted with at least one of —O—, —S—, —C(O)—, —C(O)O—, —S(O)—, —S(O$_2$)—, —N═N—, —N(R$_7$)— where R$_7$ is selected from hydrogen, hydrocarbyl or substituted hydrocarbyl, —Si(OR$_8$)$_w$(R$_6$)$_t$—, where w and t are each independently selected from 0 to 2, provided that the sum of w and t is 2, and each R$_7$ is independently selected from hydrogen, hydrocarbyl and substituted hydrocarbyl, and combinations of two or more thereof; halogen; cyano; —N(R$_9$)R$_{10}$, wherein R$_9$ and R$_{10}$ are each independently selected from hydrogen, hydrocarbyl or substituted hydrocarbyl, or R$_9$ and R$_{10}$ together form a ring structure optionally including at least one heteroatom; and a group L as defined further herein below.

With additional reference to Formulas (I), (II), and (III), R$_2$, R$_3$, R$_4$, and R$_5$ are each independently selected from hydrogen, hydrocarbyl and substituted hydrocarbyl each optionally and independently interrupted with at least one of —O—, —S—, —N(R$_7$)— where R$_7$ is selected from hydrogen, hydrocarbyl or substituted hydrocarbyl, —Si(OR$_6$)$_w$(R$_8$)$_t$—, where w and t are each independently selected from 0 to 2, provided that the sum of w and t is 2, and each R$_8$ is independently selected from hydrogen, hydrocarbyl and substituted hydrocarbyl, and combinations of two or more thereof; halogen; —N(R$_9$)R$_{10}$, wherein R$_9$ and R$_{10}$ are each independently selected from hydrogen, hydrocarbyl or substituted hydrocarbyl, or R$_9$ and R$_{10}$ together form a ring structure optionally including at least one heteroatom.

Alternatively, and with further reference to Formulas (I), (II), and (III), R$_2$ and R$_3$ can, with some embodiments, together form a ring structure optionally including at least one heteroatom.

Alternatively, and with further reference to Formulas (I), (II), and (III), R$_4$ and R$_5$ together form a ring structure optionally including at least one heteroatom.

With additional further reference to Formulas (I), (II), and (III), B and B' are each independently selected from, hydrogen, unsubstituted aryl, substituted aryl, unsubstituted heteroaryl, and substituted heteroaryl, or B and B' taken together form a ring structure selected from unsubstituted fluoren-9-ylidene, substituted fluoren-9-ylidene, saturated spiro-monocyclic hydrocarbon ring, saturated spiro-bicyclic hydrocarbon ring, and spiro-tricyclic hydrocarbon ring.

With further reference to Formulas (I), (II), and (III), there is the proviso that: (i) at least one R$_1$ is the group L; and/or (ii) at least one of B and B' is substituted with at least one group L, in which each group L is independently as described further herein below.

Each group L of the naphthopyran compounds according to the present invention as represented by Formulas (I), (II), and (III), is independently represented by the following Formula (IV),

—[S$_1$]$_c$-[Q$_1$-[S$_2$]$_d$]$_{d'}$-[Q$_2$-[S$_3$]$_e$]$_{e'}$-[Q$_3$-[S$_4$]$_f$]$_{f'}$-S$_5$—P    Formula (IV)

With reference to Formula (IV), (a) Q$_1$, Q$_2$, and Q$_3$ for each occurrence, are independently selected from a divalent group selected from optionally substituted aryl, optionally substituted heteroaryl, optionally substituted cycloalkyl, and optionally substituted heterocycloalkyl.

With further reference to Q$_1$, Q$_2$, and Q$_3$ of Formula (IV), the aryl substituents, heteroaryl substituents, cycloalkyl substituents, and heterocycloalkyl substituents are each independently selected from P (as described further herein), liquid crystal mesogens, halogen, poly(C$_1$-C$_{18}$ alkoxy), C$_1$-C$_{18}$ alkoxycarbonyl, C$_1$-C$_{18}$ alkylcarbonyl, C$_1$-C$_{18}$ alkoxycarbonyloxy, aryloxycarbonyloxy, perfluoro(C$_1$-C$_{18}$)alkoxy, perfluoro(C$_1$-C$_{18}$)alkoxycarbonyl, perfluoro(C$_1$-C$_{18}$)alkylcarbonyl, perfluoro(C$_1$-C$_{18}$)alkylamino, di-(perfluoro(C$_1$-C$_{18}$)alkyl)amino, perfluoro(C$_1$-C$_{18}$)alkylthio, C$_1$-C$_{18}$ alkylthio, C$_1$-C$_{18}$ acetyl, C$_3$-C$_{10}$ cycloalkyl, C$_3$-C$_{10}$ cycloalkoxy, straight-chain C$_1$-C$_{18}$ alkyl, and branched C$_1$-C$_{18}$alkyl.

With additional reference to Q$_1$, Q$_2$, and Q$_3$ of Formula (IV), the straight-chain C$_1$-C$_{18}$ alkyl and branched C$_1$-C$_{18}$ alkyl are, with some embodiments, mono-substituted with a group selected from cyano, halogen, and C$_1$-C$_{18}$ alkoxy.

With additional further reference to Q$_1$, Q$_2$, and Q$_3$ of Formula (IV), alternatively the straight-chain C$_1$-C$_{18}$ alkyl and branched C$_1$-C$_{18}$ alkyl are, with some embodiments, poly-substituted with at least two groups independently selected from halogen, -M(T)$_{(v-1)}$ and -M(OT)$_{(v-1)}$, wherein M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and v is the valence of M.

With reference to Formula (IV), (b) subscripts c, d, e, and f are each independently chosen from an integer of from 1 to 20.

The groups S$_1$, S$_2$, S$_3$, S$_4$, and S$_5$ of Formula (IV) are each independently chosen for each occurrence from a spacer unit selected from (i), (ii), and/or (iii) as follows.

With some embodiments, S$_1$, S$_2$, S$_3$, S$_4$, and S$_5$ of Formula (IV) are each independently chosen for each occurrence from a spacer unit selected from (i) optionally substituted alkylene, optionally substituted haloalkylene, —Si(CH$_2$)$_g$—, and —(Si[(CH$_3$)$_2$]O)$_h$—, wherein g for each occurrence is independently chosen from an integer from 1 to 20; h for each occurrence is independently chosen from an integer from 1 to 16; and the substituents for the alkylene and haloalkylene are independently selected from C$_1$-C$_{18}$alkyl, C$_3$-C$_{10}$ cycloalkyl and aryl.

With some additional embodiments, $S_1$, $S_2$, $S_3$, $S_4$, and $S_5$ of Formula (IV) are each independently chosen for each occurrence from a spacer unit selected from (ii) —N(Z)—, —C(Z)═C(Z)—, —C(Z)═N—, —C(Z')$_2$—C(Z')$_2$—, and a single bond, wherein Z for each occurrence is independently selected from hydrogen, $C_1$-$C_{18}$ alkyl, $C_3$-$C_{10}$ cycloalkyl and aryl, and Z' for each occurrence is independently selected from $C_1$-$C_{18}$ alkyl, $C_3$-$C_{10}$ cycloalkyl and aryl.

With some further embodiments, $S_1$, $S_2$, $S_3$, $S_4$, and $S_5$ of Formula (IV) are each independently chosen for each occurrence from a spacer unit selected from (iii) —O—, —C(═O)—, —C≡C—, —N═N—, —S—, —S(═O)—, —(O═)S(═O)—, —(O═)S(═O)O—, —O(O═)S(═O)O— and straight-chain or branched $C_1$-$C_{24}$ alkylene residue, where the $C_1$-$C_{74}$ alkylene residue is unsubstituted, mono-substituted by cyano or halogen, or poly-substituted by halogen.

With further reference to $S_1$, $S_2$, $S_3$, $S_4$, and $S_5$ of Formula (IV), there is the proviso that: when two spacer units comprising heteroatoms are linked together the spacer units are linked so that heteroatoms are not directly linked to each other; each bond between $S_1$ and a naphthopyran compound represented by Formulas (I), (II), and (III) is in each case free of two heteroatoms linked together, and the bond between $S_5$ and P is free of two heteroatoms linked to each other.

With additional reference to $S_1$, $S_2$, $S_3$, $S_4$, and $S_5$ of Formula (IV), there is the further proviso that $S_2$ is not —N(H)— and not —O—.

With reference to Formula (IV), (c) P independently for each group L is selected from hydroxy, amino, $C_2$-$C_{18}$ alkenyl, $C_2$-$C_{18}$ alkynyl, azido, silyl, siloxy, silylhydride, (tetrahydro-2H-pyran-2-yl)oxy, thio, isocyanato, thioisocyanato, acryloyloxy, methacryloyloxy, 2-(acryloyloxy)ethylcarbamyl, 2-(methacryloyloxy)ethylcarbamyl, aziridinyl, allyloxycarbonyloxy, epoxy, carboxylic acid, carboxylic ester, acryloylamino, methacryloylamino, aminocarbonyl, $C_1$-$C_{18}$ alkyl aminocarbonyl, aminocarbonyl($C_1$-$C_{18}$)alkyl, $C_1$-$C_{18}$alkyloxycarbonyloxy, halocarbonyl, hydrogen, aryl, hydroxy($C_1$-$C_{18}$)alkyl, $C_1$-$C_{18}$ alkyl, $C_1$-$C_{18}$alkoxy, amino($C_1$-$C_{18}$)alkyl, $C_1$-$C_{18}$ alkylamino, di-($C_1$-$C_{18}$)alkylamino, $C_1$-$C_{18}$ alkyl($C_1$-$C_{18}$)alkoxy, $C_1$-$C_{18}$ alkoxy($C_1$-$C_{18}$)alkoxy, nitro, poly($C_1$-$C_{18}$)alkyl ether, ($C_1$-$C_{18}$)alkyl($C_1$-$C_{18}$)alkoxy($C_1$-$C_{18}$)alkyl, polyethyleneoxy, polypropyleneoxy, ethylene, acryloyl, acryloyloxy($C_1$-$C_{18}$) alkyl, methacryloyl, methacryloyloxy($C_1$-$C_{18}$)alkyl, 2-chloroacryloyl, 2-phenylacryloyl, acryloyloxyphenyl, 2-chloroacryloylamino, 2-phenylacryloylaminocarbonyl, oxetanyl, glycidyl, cyano, isocyanato($C_1$-$C_{18}$)alkyl, itaconic acid ester, vinyl ether, vinyl ester, a styrene derivative, main-chain and side-chain liquid crystal polymers, siloxane derivatives, ethyleneimine derivatives, maleic acid derivatives, maleimide derivatives, fumaric acid derivatives, unsubstituted cinnamic acid derivatives, cinnamic acid derivatives that are substituted with at least one of methyl, methoxy, cyano and halogen, and substituted or unsubstituted chiral or non-chiral monovalent or divalent groups chosen from steroid radicals, terpenoid radicals, alkaloid radicals and mixtures thereof, wherein the substituents are independently chosen from $C_1$-$C_{18}$ alkyl, $C_1$-$C_1$, alkoxy, amino, $C_3$-$C_{10}$ cycloalkyl, $C_1$-$C_{18}$ alkyl($C_1$-$C_{18}$)alkoxy, fluoro($C_1$-$C_{18}$)alkyl, cyano, cyano($C_1$-$C_{18}$)alkyl, cyano($C_1$-$C_{18}$)alkoxy, or mixtures and/or combinations thereof. Alternatively, each P independently is a structure having from 2 to 4 reactive groups, or P is an unsubstituted or substituted ring opening metathesis polymerization precursor, or P is a substituted or unsubstituted photochromic compound.

With reference subscripts d', e', and f' of Formula (IV): d' is chosen from 1, 2, 3, and 4; and e' and f' are each independently chosen from 0, 1, 2, 3, and 4. With further reference subscripts d', e', and f of Formula (IV), there is the proviso that the sum of d'+e'+f' is at least 2.

The features that characterize the present invention are pointed out with particularity in the claims, which are annexed to and form a part of this disclosure. These and other features of the invention, its operating advantages and the specific objects obtained by its use will be more fully understood from the following detailed description in which non-limiting embodiments of the invention are illustrated and described.

BRIEF DESCRIPTION OF THE DRAWINGS

In FIGS. 1-8 like characters refer to the same aspects, structural features, and/or components, as the case may be, unless otherwise stated.

DETAILED DESCRIPTION

Figure 1:
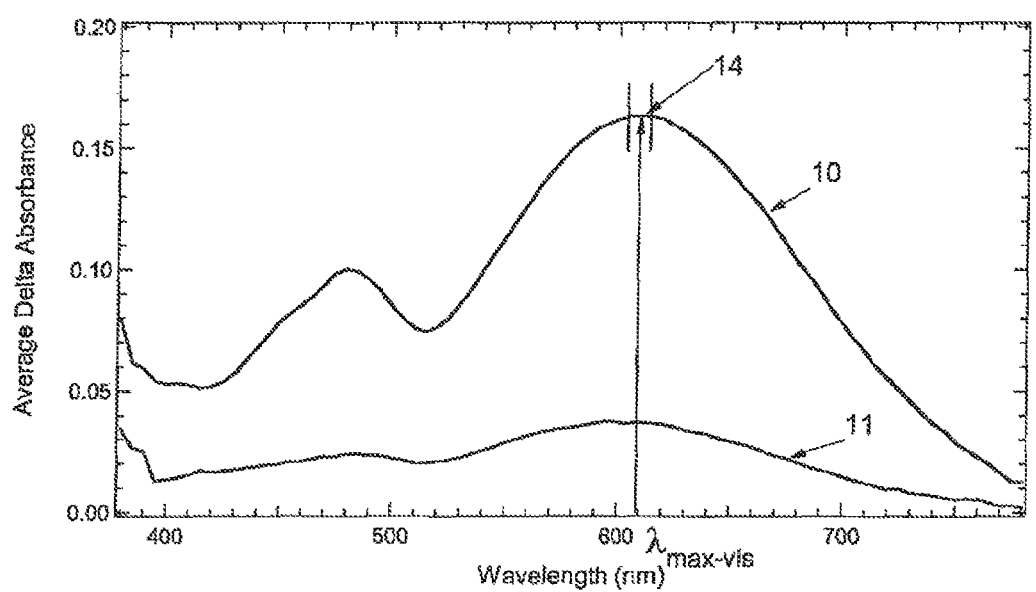
FIG. 1 is an illustrative graphical representation of two average difference absorption spectrum obtained for a photochromic-dichroic compound, and is provided for purposes of illustrating and explaining the CELL METHOD.

As used herein, the articles "a," "an," and "the" include plural referents unless otherwise expressly and unequivocally limited to one referent.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

As used herein, unless otherwise indicated, left-to-right representations of linking groups, such as divalent linking groups, are inclusive of other appropriate orientations, such as, but not limited to, right-to-left orientations. For purposes of non-limiting illustration, the left-to-right representation of the divalent linking group

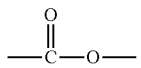

or equivalently —C(O)O—, is inclusive of the right-to-left representation thereof,

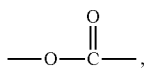

or equivalently —O(O)C— or —OC(O)—.

Other than in the operating examples, or where otherwise indicated, all numbers expressing quantities of ingredients, reaction conditions, and so forth used in the specification and claims are to be understood as modified in all instances by the term "about."

The naphthopyran compounds of the present invention, including those represented by Formulas (I), (II), and (III), in each case optionally further include one or more co-products, resulting from the synthesis of such naphthopyran compounds.

As used herein, the term "photochromic" and similar terms, such as "photochromic compound" means having an absorption spectrum for at least visible radiation that varies in response to absorption of at least actinic radiation. Further, as used herein the term "photochromic material" means any substance that is adapted to display photochromic properties (such as, adapted to have an absorption spectrum for at least visible radiation that varies in response to absorption of at least actinic radiation) and which includes at least one photochromic compound.

As used herein, the term "actinic radiation" means electromagnetic radiation that is capable of causing a response in a material, such as, but not limited to, transforming a photochromic material from one form or state to another as will be discussed in further detail herein.

As used herein, the term "photochromic material" includes thermally reversible photochromic materials and compounds and non-thermally reversible photochromic materials and compounds. The term "thermally reversible photochromic compounds/materials" as used herein means compounds/materials capable of converting from a first state, for example a "clear state," to a second state, for example a "colored state," in response to actinic radiation, and reverting back to the first state in response to thermal energy. The term "non-thermally reversible photochromic compounds/materials" as used herein means compounds/materials capable of converting from a first state, for example a "clear state," to a second state, for example a "colored state," in response to actinic radiation, and reverting back to the first state in response to actinic radiation of substantially the same wavelength(s) as the absorption(s) of the colored state (e.g., discontinuing exposure to such actinic radiation).

As used herein to modify the term "state," the terms "first" and "second" are not intended to refer to any particular order or chronology, but instead refer to two different conditions or properties. For purposes of non-limiting illustration, the first state and the second state of a photochromic compound can differ with respect to at least one optical property, such as but not limited to the absorption of visible and/or UV radiation. Thus, according to various non-limiting embodiments disclosed herein, the photochromic compounds of the present invention can have a different absorption spectrum in each of the first and second state. For example, while not limiting herein, a photochromic compound of the present invention can be clear in the first state and colored in the second state. Alternatively, a photochromic compound of the present invention can have a first color in the first state and a second color in the second state.

As used herein the term "linearly polarize" means to confine the vibrations of the electric vector of electromagnetic waves, such as light waves, to one direction or plane.

As used herein the term "dichroic ratio" refers to the ratio of the absorbance of radiation linearly polarized in a first plane to the absorbance of the same wavelength radiation linearly polarized in a plane orthogonal to the first plane, in which the first plane is taken as the plane with the highest absorbance.

As used herein the term "optical" means pertaining to or associated with light and/or vision. For example, according to various non-limiting embodiments disclosed herein, the optical article or element or device can be chosen from ophthalmic articles, elements and devices, display articles, elements and devices, windows, mirrors, and active and passive liquid crystal cell articles, elements and devices.

As used herein the term "ophthalmic" means pertaining to or associated with the eye and vision. Non-limiting examples of ophthalmic articles or elements include corrective and non-corrective lenses, including single vision or multi-vision lenses, which can be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intra-ocular lenses, magnifying lenses, and protective lenses or visors.

As used herein the term "ophthalmic substrate" means lenses, partially formed lenses, and lens blanks.

As used herein the term "coating" means a supported film derived from a flowable composition, which can or can not have a uniform thickness, and specifically excludes polymeric sheets. A layer that includes one or more photochromic compounds of the present invention can, with some embodiments, be a photochromic coating.

As used herein the term "sheet" means a pre-formed film having a generally uniform thickness and capable of self-support.

As used herein the term "connected to" means in direct contact with an object or indirect contact with an object through one or more other structures or materials, at least one of which is in direct contact with the object. For purposes of non-limiting illustration, a coating containing one or more naphthopyran compounds of the present invention, for example, can be in direct contact (e.g., abutting contact) with at least a portion of a substrate, such as an optical article, or it can be in indirect contact with at least a portion of the substrate through one or more other interposed structures or materials, such as a monomolecular layer of a coupling or adhesive agent. For example, although not limiting herein, a coating containing one or more naphthopyran compounds of the present invention, can be in contact with one or more other interposed coatings, polymer sheets or combinations thereof, at least one of which is in direct contact with at least a portion of the substrate.

As used herein, the term "photosensitive material" means materials that physically or chemically respond to electromagnetic radiation, including, but not limited to, phosphorescent materials and fluorescent materials.

As used herein, the term "non-photosensitive materials" means materials that do not physically or chemically respond to electromagnetic radiation, including, but not limited to, static dyes.

As used herein, the term "polymer" means homopolymers (e.g., prepared from a single monomer species), copolymers (e.g., prepared from at least two monomer species), and graft polymers.

As used herein, the term "(meth)acrylate" and similar terms, such as "(meth)acrylic acid ester" means methacrylates and/or acrylates. As used herein, the term "(meth)acrylic acid" means methacrylic acid and/or acrylic acid.

As used herein, spatial or directional terms, such as "left", "right", "inner", "outer", "above", "below", and the like, relate to the invention as it is depicted in the drawing figures. However, it is to be understood that the invention can assume various alternative orientations and, accordingly, such terms are not to be considered as limiting.

As used herein, the terms "formed over," "deposited over," "provided over," "applied over," residing over," or "positioned over," mean formed, deposited, provided, applied, residing, or positioned on but not necessarily in direct (or abutting) contact with the underlying element, or surface of the underlying element. For example, a layer "positioned over" a substrate does not preclude the presence of one or more other layers, coatings, or films of the same or different composition located between the positioned or formed layer and the substrate.

All documents, such as but not limited to issued patents and patent applications, referred to herein, and unless otherwise indicated, are to be considered to be "incorporated by reference" in their entirety.

As used herein, recitations of "linear or branched" groups, such as linear or branched alkyl, are herein understood to include: a methylene group or a methyl group; groups that are linear, such as linear $C_2$-$C_{20}$ alkyl groups; and groups that are appropriately branched, such as branched $C_3$-$C_{20}$ alkyl groups.

As used herein, recitations of "optionally substituted" group, means a group, including but not limited to, alkyl group, cycloalkyl group, heterocycloalkyl group, aryl group, and/or heteroaryl group, in which at least one hydrogen thereof has been optionally replaced or substituted with a group that is other than hydrogen, such as, but not limited to, halo groups (e.g., F, Cl, I, and Br), hydroxyl groups, ether groups, thiol groups, thio ether groups, carboxylic acid groups, carboxylic acid ester groups, phosphoric acid groups, phosphoric acid ester groups, sulfonic acid groups, sulfonic acid ester groups, nitro groups, cyano groups, hydrocarbyl groups (including, but not limited to: alkyl; alkenyl; alkynyl; cycloalkyl, including poly-fused-ring cycloalkyl and polycyclocalkyl; heterocycloalkyl; aryl, including hydroxyl substituted aryl, such as phenol, and including poly-fused-ring aryl; heteroaryl, including poly-fused-ring heteroaryl; and aralkyl groups), and amine groups, such as —N($R^{11}$)($R^{12}$) where $R^{11}$ and $R^{12}$ are each independently selected from hydrogen, linear or branched $C_1$-$C_{20}$ alkyl, $C_3$-$C_{12}$ cycloalkyl, $C_3$-$C_{12}$ heterocycloalkyl, aryl, and heteroaryl.

As used herein, recitations of "halo substituted" and related terms (such as, but not limited to, haloalkyl groups, haloalkenyl groups, haloalkynyl groups, haloaryl groups and haloheteroaryl groups) means a group in which at least one, and up to and including all of the available hydrogen groups thereof is substituted with a halo group. The term "halo-substituted" is inclusive of "perhalo-substituted." As used herein, the term perhalo-substituted group and related terms (such as, but not limited to perhaloalkyl groups, perhaloalkenyl groups, perhaloalkynyl groups, perhaloaryl groups and perhalo-heteroaryl groups) means a group in which all of the available hydrogen groups thereof is substituted with a halo group. For example, perhalomethyl is —$CX_3$; perhalophenyl is —$C_6X_5$, where each X independently represents a halo group (e.g., F).

The naphthopyran compounds of the present invention include groups and sub-groups, such as, but not limited to, $R^1$-$R^5$, $R_7$, $R_8$, $R_9$, and $R_{10}$, that can in each case be independently selected from hydrocarbyl and/or substituted hydrocarbyl. As used herein the term "hydrocarbyl" and similar terms, such as "hydrocarbyl substituent," means: linear or branched $C_1$-$C_{25}$ alkyl (e.g., linear or branched $C_1$-$C_{10}$ alkyl); linear or branched $C_2$-$C_{25}$ alkenyl (e.g., linear or branched $C_2$-$C_{10}$ alkenyl); linear or branched $C_2$-$C_{25}$ alkynyl (e.g., linear or branched $C_2$-$C_{10}$ alkynyl); $C_3$-$C_{12}$ cycloalkyl (e.g., $C_3$-$C_{10}$ cycloalkyl); $C_3$-$C_2$ heterocycloalkyl (having at least one hetero atom in the cyclic ring); $C_5$-$C_{18}$ aryl (including polycyclic aryl groups) (e.g., $C_5$-$C_{10}$ aryl); $C_5$-$C_{18}$ heteroaryl (having at least one hetero atom in the aromatic ring); and $C_6$-$C_{24}$ aralkyl (e.g., $C_6$-$C_{10}$ aralkyl).

Representative alkyl groups include but are not limited to methyl, ethyl, propyl, isopropyl, butyl, isobutyl, sec-butyl, tert-butyl, pentyl, neopentyl, hexyl, heptyl, octyl, nonyl and decyl. Representative alkenyl groups include but are not limited to vinyl, allyl and propenyl. Representative alkynyl groups include but are not limited to ethynyl, 1-propynyl, 2-propynyl, 1-butynyl, and 2-butynyl. Representative cycloalkyl groups include but are not limited to cyclopropyl, cyclobutyl, cyclopentyl, cyclohexyl, and cyclooctyl substituents. Representative heterocycloalkyl groups include but are not limited to imidazolyl, tetrahydrofuranyl, tetrahydropyranyl and piperidinyl. Representative aryl groups include but are not limited to phenyl, naphthyl, anthracynyl and triptycenyl. Representative heteroaryl groups include but are not limited to furanyl, pyranyl, pyridinyl, isoquinoline, and pyrimidinyl. Representative aralkyl groups include but are not limited to benzyl, and phenethyl.

The term "substituted hydrocarbyl" as used herein means a hydrocarbyl group in which at least one hydrogen thereof has been substituted with a group that is other than hydrogen, such as, but not limited to, halo groups, hydroxyl groups, ether groups, thiol groups, thio ether groups, carboxylic acid groups, carboxylic acid ester groups, phosphoric acid groups, phosphoric acid ester groups, sulfonic acid groups, sulfonic acid ester groups, nitro groups, cyano groups, hydrocarbyl groups (e.g., alkyl, alkenyl, alkynyl, cycloalkyl, heterocycloalkyl, aryl, heteroaryl, and aralkyl groups), and amine groups, such as —N($R_9$)($R_{10}$) where $R_9$ and $R_{10}$ are each independently selected from hydrogen, hydrocarbyl and substituted hydrocarbyl.

The term "substituted hydrocarbyl" is inclusive of halohydrocarbyl (or halo substituted hydrocarbyl) substituents. The term "halohydrocarbyl" as used herein, and similar terms, such as halo substituted hydrocarbyl, means that at least one hydrogen atom of the hydrocarbyl (e.g., of the alkyl, alkenyl, alkynyl, cycloalkyl, heterocycloalkyl, aryl, heteroaryl, and aralkyl groups) is replaced with a halogen atom selected from chlorine, bromine, fluorine and iodine. The degree of halogenation can range from at least one hydrogen atom but less than all hydrogen atoms being replaced by a halogen atom (e.g., a fluoromethyl group), to full halogenation (perhalogenation) in which all replaceable hydrogen atoms on the hydrocarbyl group have each been replaced by a halogen atom (e.g., trifluoromethyl or perfluoromethyl). Correspondingly, the term "perhalohydrocarbyl group" as used herein means a hydrocarbyl group in which all replaceable hydrogens have been replaced with a halogen. Examples of perhalohydrocarbyl groups include, but are not limited to, perhalogenated phenyl groups and perhalogenated alkyl groups.

The hydrocarbyl and substituted hydrocarbyl groups from which the various groups described herein can each be independently selected, such as, but not limited to, $R^1$-$R^5$, $R_7$, $R_8$, $R_9$, and $R_{10}$, can in each case be independently and optionally interrupted with at least one of —O—, —S—, —C(O)—, —C(O)O—, —OC(O)O—, —S(O)—, —SO$_2$—, —N($R_7$)— and —Si(O$R_8$)$_w$($R_8$)$_t$—. As used herein, by interrupted with at least one of —O—, —S—, —C(O)—, —C(O)O—, —OC(O)O—, —S(O)—, —SO$_2$—, —N($R_7$)—, and —Si(O$R_8$)$_w$($R_8$)$_t$—, means that at least one carbon of, but less than all of the carbons of, the hydrocarbyl group or substituted hydrocarbyl group, is in each case independently replaced with one of the recited divalent non-carbon linking groups. The hydrocarbyl and substituted hydrocarbyl groups can be interrupted with two or more of the above recited linking groups, which can be adjacent to each other or separated by one or more carbons. For purposes of non-limiting illustration, a combination of adjacent —C(O)— and —N($R_7$)— can provide a divalent amide linking or interrupting group, —C(O)—N($R_7$)—. For purposes of further non-limiting illustration, a combination of adjacent —N($R_7$)—, —C(O)— and —O— can provide a divalent carbamate (or urethane) linking or interrupting group, —N($R_7$)—C(O)—O—, where $R_7$ is hydrogen.

The term "alkyl" as used herein, in accordance with some embodiments, means linear or branched alkyl, such as but not limited to, linear or branched $C_1$-$C_{25}$ alkyl, or linear or branched $C_1$-$C_{10}$ alkyl, or linear or branched $C_2$-$C_{10}$ alkyl. Examples of alkyl groups from which the various alkyl groups of the present invention can be selected from, include, but are not limited to, those recited previously herein. Alkyl groups of the various compounds of the present invention can, with some embodiments, include one or more unsaturated linkages selected from —CH=CH— groups and/or one or more —C≡C— groups, provided the alkyl group is free of two or more conjugated unsaturated linkages. With some embodiments, the alkyl groups are free of unsaturated linkages, such as —CH=CH— groups and —C≡C— groups.

The term "cycloalkl" as used herein, in accordance with some embodiments, means groups that are appropriately cyclic, such as but not limited to, $C_3$-$C_{12}$ cycloalkyl (including, but not limited to, cyclic $C_5$-$C_7$ alkyl) groups. Examples of cycloalkyl groups include, but are not limited to, those recited previously herein. The term "cycloalkyl" as used herein in accordance with some embodiments also includes: bridged ring polycycloalkyl groups (or bridged ring polycyclic alkyl groups), such as but not limited to, bicyclo[2.2.1]heptyl (or norbornyl) and bicyclo[2.2.2]octyl; and fused ring polycycloalkyl groups (or fused ring polycyclic alkyl groups), such as, but not limited to, octahydro-1H-indenyl, and decahydronaphthalenyl.

The term "heterocycloalkyl" as used herein, in accordance with some embodiments, means groups that are appropriately cyclic, such as but not limited to, $C_3$-$C_{12}$ heterocycloalkyl groups or $C_5$-$C_7$ heterocycloalkyl groups, and which have at least one hetero atom in the cyclic ring, such as, but not limited to, O, S, N, P, and combinations thereof. Examples of heterocycloalkyl groups include, but are not limited to, those recited previously herein. The term "heterocycloalkyl" as used herein, in accordance with some embodiments, also includes: bridged ring polycyclic heterocycloalkyl groups, such as but not limited to, 7-oxabicyclo[2.2.1]heptanyl; and fused ring polycyclic heterocycloalkyl groups, such as but not limited to, octahydrocyclopenta[b]pyranyl, and octahydro-1H-isochromenyl.

The term "heteroaryl," as used herein, in accordance with some embodiments, includes but is not limited to $C_5$-$C_{18}$ heteroaryl, such as but not limited to $C_5$-$C_{10}$ heteroaryl (including fused ring polycyclic heteroaryl groups) and means an aryl group having at least one hetero atom in the aromatic ring, or in at least one aromatic ring in the case of a fused ring polycyclic heteroaryl group. Examples of heteroaryl groups include, but are not limited to, those recited previously herein.

As used herein, the term "fused ring polycyclic-aryl-alkyl group" and similar terms such as, fused ring polycyclic-alkyl-aryl group, fused ring polycyclo-aryl-alkyl group, and fused ring polycyclo-alkyl-aryl group means a fused ring polycyclic group that includes at least one aryl ring and at least one cycloalkyl ring that are fused together to form a fused ring structure. For purposes of non-limiting illustration, examples of fused ring polycyclic-aryl-alkyl groups include, but are not limited to indenyl, 9H-flourenyl, cyclopentanaphthenyl, and indacenyl.

The term "aralkyl," as used herein, and in accordance with some embodiments, includes but is not limited to $C_6$-$C_{24}$ aralkyl, such as but not limited to $C_6$-$C_{10}$ aralkyl, and means an aryl group substituted with an alkyl group. Examples of aralkyl groups include, but are not limited to, those recited previously herein.

As used herein, the term "ring-position" and related terms, such as "Position" means a particular position in the ring structure, such as the fused ring structure, of a chemical compound, such as the naphthopyran compounds represented by Formulas (I), (II), and (III) of the present invention, and which are depicted herein in accordance with some embodiments by numbers within the ring structures of representative chemical formulas.

The naphthopyran compounds of the present invention can be referred to herein with regard to various groups at (or bonded to) various positions of the naphthopyran compounds. The positions are referred to herein, with some embodiments, with regard to the ring-positions as enumerated in the representative Formulas (I), (II), and (III) as provided above.

For purposes of non-limiting illustration, with the naphthopyran compounds represented by Formulas (I), (II), and (III): B and B' are each at (or bonded to) Position-2 (or the 2-position); $R_1$ is at (or bonded to) at least one of Position-7, Position-8, Position-9, and Position-10 (or the 7-Position, 8-Position, 9-Position, and/or 10-Position). With further reference to Formulas (I), (II), and (III) the five-membered ring that includes X is, in each case, fused to (or across) Position-5 and Position-6.

With reference to Formula (I), the groups $R_2$ and $R_3$ are both positioned on the five-membered fused ring at a position that is adjacent to Position-6, as depicted.

With reference to Formula (II), the groups $R_2$ and $R_3$ are both positioned on the five-membered fused ring at a position that is adjacent to Position-5, as depicted.

With reference to Formula (III), the groups $R_2$ and $R_3$ are both positioned on the five-membered fused ring at a position that is adjacent to Position-6, as depicted. With further reference to Formula (II), the groups $R_4$ and $R_5$ are both positioned on the five-membered fused ring at a position that is adjacent to Position-5, as depicted.

The naphthopyran compounds of the present invention, for example as represented by Formulas (I), (II), and (III), and the various groups thereof are described in further detail herein as follows.

With reference to Formulas (I), (II), and (III), $R_1$ independently for each of Formulas (I), (II), and (III), and independently for each q is selected from, with some embodiments: a reactive substituent; a compatiblizing substituent; hydrogen; fluoro; chloro; $C_1$-$C_6$ alkyl; $C_3$-$C_7$ cycloalkyl; substituted or unsubstituted phenyl; —$OR_{10}$' or —$OC(=O)R_{10}$', wherein $R_{10}$' is hydrogen, $C_1$-$C_6$ alkyl, phenyl($C_1$-$C_3$)alkyl, mono($C_1$-$C_6$)alkyl substituted phenyl($C_1$-$C_3$)alkyl, mono($C_1$-$C_6$) alkoxy substituted phenyl($C_1$-$C_3$)alkyl, ($C_1$-$C_6$)alkoxy($C_2$-$C_4$)alky, $C_3$-$C_7$ cycloalkyl, or mono($C_1$-$C_4$)alkyl substituted $C_3$-$C_7$ cycloalkyl, and said phenyl substituents being hydroxyl, halogen, carbonyl, $C_1$-$C_6$ alkoxycarbonyl, cyano, halo($C_1$-$C_6$)alkyl, $C_1$-$C_6$ alkyl or $C_1$-$C_6$ alkoxy; —$N(R_{11}')R_{12}'$, wherein $R_{11}'$ and $R_{12}'$ are each independently hydrogen, $C_1$-$C_8$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$-$C_8$ alkylaryl, $C_3$-$C_{20}$ cycloalkyl, $C_4$-$C_{20}$ bicycloalkyl, $C_5$-$C_{20}$ tricycloalkyl or $C_1$-$C_{20}$ alkoxyalkyl, wherein said aryl group is phenyl or naphthyl, or $R_{11}'$ and $R_{12}'$ come together with the nitrogen atom to form a $C_3$-$C_{20}$ hetero-bicycloalkyl ring or a $C_4$-$C_{20}$ hetero-tricycloalkyl ring.

With reference to Formulas (I), (II), and (III), $R_1$ independently for each of Formulas (I), (II), and (III), and independently for each q is selected from, with some embodiments, a nitrogen containing ring represented by the following graphic formula (VA):

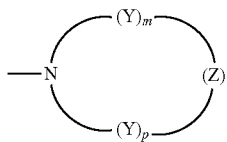

(VA)

With reference to Formula (VA), and in accordance with some embodiments, each —Y— is independently chosen for each occurrence from —$CH_2$—, —$CH(R_{13}')$—, —$C(R_{13}')_2$—, —CH(aryl)-, —C(aryl)$_2$-, and —$C(R_{13}')$(aryl)-, and Z is —Y—, —O—, —S—, —S(O)—, —$SO_2$—, —NH—, —$N(R_{13}')$—, or —N(aryl)-, wherein each $R_{13}'$ is independently $C_1$-$C_6$ alkyl, each aryl is independently phenyl or naphthyl, p is an integer 1, 2 or 3, and m is an integer 0, 1, 2, or 3, and provided that when m is 0, Z is —Y—.

With further reference to Formulas (I), (II), and (III), $R_1$ independently for each of Formulas (I), (II), and (III), and independently for each q is selected from, with some embodiments, a group represented by one of the following Formulas (VB) or (VC):

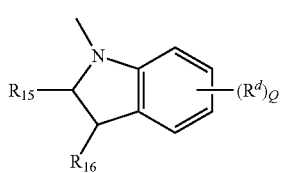

(VB)

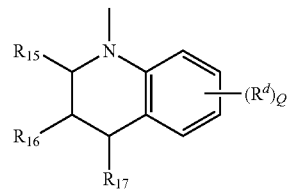

(VC)

With reference to Formulas (VB) and (VC), and in accordance with some embodiments: $R_{15}$, $R_{16}$, and $R_{17}$ are each independently, hydrogen, $C_1$-$C_6$ alkyl, phenyl, or naphthyl, or the groups $R_{15}$ and $R_{16}$ together form a ring of 5 to 8 carbon atoms; each $R^d$ is independently for each occurrence selected from $C_1$-$C_6$ alkyl, $C_1$-$C_6$ alkoxy, fluoro or chloro; and Q is an integer 0, 1, 2, or 3.

With further reference to Formulas (I), (II), and (III), $R_1$ independently for each of Formulas (I), (II), and (III), and independently for each q is selected from, with some embodiments, unsubstituted, mono-, or di-substituted $C_4$-$C_{18}$ spirobicyclic amine, or unsubstituted, mono-, and di-substituted $C_4$-$C_{18}$ spirotricyclic amine, wherein the substituents are independently aryl, $C_1$-$C_6$ alkyl, $C_1$-$C_6$ alkoxy, or phenyl($C_1$-$C_6$)alkyl.

Independently for each of Formulas (I), (II), and (III), and with some embodiments, two adjacent $R^1$ groups as Position-7 and Position-8 together form a group represented by the following Formulas (VD) or (VE):

(VD)

(VE)

With reference to Formulas (VD) and (VE), T and T' are each independently oxygen or the group —$NR_{11'}$—, where $R_{11'}$, $R_{15}$, and $R_{16}$ are as set forth and described herein above.

With reference to Formulas (I), (II), and (II), and in accordance with some embodiments, there is the proviso that at least one $R_1$ is the group L as described herein.

With further reference to Formulas (I), (II), and (III), and in accordance with some embodiments, $R_2$, $R_3$, $R_4$, and $R_6$, are each independently chosen in each case from hydrogen, linear or branched $C_1$-$C_{20}$ alkyl, $C_3$-$C_7$ cycloalkyl, unsubstituted aryl, and substituted aryl, where said aryl substituents are selected from at least one of hydroxyl, halogen, cyano, hydrocarbyl, substituted hydrocarbyl, alkoxy, and —$N(R_9)R_{10}$ where $R_9$ and $R_{10}$ are each independently selected from hydrogen and linear or branched $C_1$-$C_{20}$ alkyl and $C_3$-$C_7$ cycloalkyl.

Alternatively, and with further reference to Formulas (I), (II), and (III), $R_2$ and $R_3$, independently for each of Formulas (I), (II), and (III), together form an optionally substituted $C_5$-$C_8$ cyclic ring, with some embodiments.

Further alternatively, and with further reference to Formulas (I), (II), and (III), $R_4$ and $R_6$ together form an optionally substituted $C_5$-$C_8$ cyclic ring, with some embodiments.

With additional reference to Formulas (I), (II), and (III), B and B' are each independently: an aryl group that is monosubstituted with a reactive substituent or a compatiblizing substituent; a substituted phenyl; a substituted aryl; a substituted 9-julolindinyl; a substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl, wherein the phenyl, aryl, 9-julolindinyl, or heteroaromatic substituent is the reactive substituent R; an unsubstituted, mono-, di-, or tri-substituted phenyl or aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl.

Each of the phenyl substituents, aryl substituents, and heteroaromatic substituents, of B and B', are each independently, with some embodiments: hydroxyl, a group —C(=O)$R_{21}$, wherein $R_{21}$ is —$OR_2$, —$N(R_{23})R_{24}$, piperidino, or morpholino, wherein $R_{22}$ is allyl, $C_1$-$C_6$ alkyl, phenyl, mono($C_1$-$C_6$)alkyl substituted phenyl, mono($C_1$-$C_6$)alkoxy substituted phenyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl ($C_1$-$C_3$)alkyl, $C_1$-$C_6$ alkoxy($C_2$-$C_4$)alkyl or $C_1$-$C_6$haloalkyl, $R_{23}$ and $R_{24}$ are each independently $C_1$-$C_8$ alkyl, $C_5$-$C_7$ cycloalkyl, phenyl or substituted phenyl, the phenyl substituents being $C_1$-$C_6$ alkyl or $C_1$-$C_6$ alkoxy, and said halo substituent is chloro or fluoro, aryl, mono($C_1$-$C_{12}$)alkoxyaryl, di($C_1$-$C_{12}$)alkoxyaryl, mono($C_1$-$C_{12}$)alkylaryl, di($C_1$-$C_{12}$) alkylaryl, haloaryl, $C_3$-$C_7$ cycloalkylaryl, $C_3$-$C_7$ cycloalkyl, $C_3$-$C_7$ cycloalkyloxy, $C_3$-$C_7$ cycloalkyloxy($C_1$-$C_{12}$)alkyl, $C_3$-$C_7$ cycloalkyloxy($C_1$-$C_{12}$)alkoxy, aryl($C_1$-$C_{12}$)alkyl, aryl ($C_1$-$C_{12}$)alkoxy, aryloxy, aryloxy($C_1$-$C_{12}$)alkyl, aryloxy($C_1$-$C_{12}$)alkoxy, mono- or di($C_1$-$C_{12}$)alkylaryl($C_1$-$C_{12}$)alkyl, mono- or di-($C_1$-$C_{12}$)alkoxyaryl($C_1$-$C_{12}$)alkyl, mono- or di-($C_1$-$C_{12}$)alkylaryl($C_1$-$C_{12}$)alkoxy, mono- or di-($C_1$-$C_{12}$) alkoxyaryl($C_1$-$C_{12}$)alkoxy, amino, mono- or di-($C_1$-$C_{12}$) alkylamino, diarylamino, piperazino, N—($C_1$-$C_{12}$) alkylpiperazino, N-arylpiperazino, aziridino, indolino, piperidino, morpholino, thiomorpholino, tetrahydroquinolino, tetrahydroisoquinolino, pyrrolidyl, $C_1$-$C_{12}$ alkyl, $C_1$-$C_{12}$ haloalkyl, $C_1$-$C_{12}$ alkoxy, mono($C_1$-$C_{12}$)alkoxy($C_1$-$C_{12}$)alkyl, acryloxy, methacryloxy, or halogen.

With some further embodiments, B and B' are each independently an unsubstituted or mono-substituted group chosen from pyrazolyl, imidazolyl, pyrazolinyl, imidazolinyl, pyrrolinyl, phenothiazinyl, phenoxazinyl, phenazinyl, and acridinyl, each of said substituents being $C_1$-$C_{12}$ alkyl, $C_1$-$C_{12}$ alkoxy, phenyl, or halogen.

With some additional embodiments, B and B' are each independently a group represented by one of the following Formulas (VIA) and (VI)B:

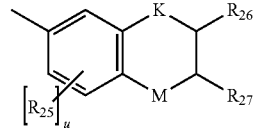

(VIA)

and

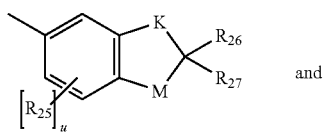

(VIB)

With reference to Formulas (VIA) and (VIB), K is —$CH_2$— or —O—, and M is —O— or substituted nitrogen, provided that when M is substituted nitrogen, K is —$CH_2$—, the substituted nitrogen substituents being hydrogen, $C_1$-$C_{12}$ alkyl, or $C_1$-$C_{12}$ acyl, each $R_{25}$ being independently chosen for each occurrence from $C_1$-$C_{12}$ alkyl, $C_1$-$C_{12}$ alkoxy, hydroxy, and halogen.

With further reference to Formulas (VIA) and (VIB), $R_{26}$ and $R_{27}$ can each be, with some embodiments, independently hydrogen or $C_1$-$C_{12}$ alkyl, and u is an integer ranging from 0 to 2; or a group represented by the following Formulas (VIC):

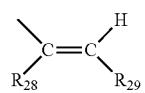

(VIC)

With reference to Formula (VIC), $R_{28}$ is hydrogen or $C_1$-$C_{12}$ alkyl, and $R_{29}$ is an unsubstituted, mono-, or di-substituted group chosen from naphthyl, phenyl, furanyl, and thienyl, wherein the substituents are $C_1$-$C_{12}$ alkyl, $C_1$-$C_{12}$ alkoxy, or halogen.

In accordance with some embodiments. B and B' taken together form one of a fluoren-9-ylidene, mono-, or di-substituted fluoren-9-ylidene. Each of the fluoren-9-ylidene substituents can independently be chosen from $C_1$-$C_{12}$ alkyl, $C_1$-$C_{12}$ alkoxy, and halogen, with some embodiments.

With some further embodiments, and with further reference to group L as represented by Formula (IV), (a) $Q_1$, $Q_2$, and $Q_3$ for each occurrence, are independently selected from optionally substituted aryl and optionally substituted cycloalkyl, where the optional aryl substituents and optional cycloalkyl substituents are selected from one or more classes and examples as recited previously herein with regard to $Q_1$, $Q_2$, and $Q_3$.

With some further embodiments, and with further reference to group L as represented by Formula (IV), (b) each $S_1$, $S_2$, $S_3$, $S_4$, and $S_5$ is independently chosen for each occurrence from a spacer unit selected from (ii) and (iii) as follows. With some embodiments, (b) each $S_1$, $S_2$, $S_3$, $S_4$, and $S_5$ is independently chosen for each occurrence from a spacer unit selected from (ii) —N(Z)—, —C(Z)=C(Z)—, —C(Z)=N—, —C(Z')$_2$—C(Z')$_2$—, and a single bond, wherein Z for each occurrence is independently selected from hydrogen, $C_1$-$C_8$ alkyl, $C_3$-$C_6$ cycloalkyl and aryl, and Z' for each occurrence is independently selected from $C_1$-$C_8$ alkyl, $C_3$-$C_6$ cycloalkyl and aryl. With some further embodiments, (b) each $S_1$, $S_2$, $S_3$, $S_4$, and $S_5$ is independently chosen for each occurrence from a spacer unit selected from (iii) —O—, —C(=O)—, —C≡C—, —N=N—, —S—, —S(=O)—, and straight-chain or branched $C_1$-$C_{12}$ alkylene residue, said $C_1$-$C_{12}$ alkylene residue being unsubstituted, mono-substituted by cyano or halogen, or poly-substituted by halogen.

With some further embodiments, and with further reference to group L as represented by Formula (IV), (c) P for each occurrence is independently selected from hydrogen, hydroxy, amino, $C_2$-$C_8$ alkenyl, $C_2$-$C_8$ alkynyl, acryloyloxy, methacryloyloxy, 2-(acryloyloxy)ethylcarbamyl, 2-(methacryloyloxy)ethylcarbamyl, epoxy, carboxylic acid, carboxylic ester, acryloylamino, methacryloylamino, aminocarbonyl, $C_1$-$C_8$ alkyl aminocarbonyl, aminocarbonyl($C_1$-$C_8$)alkyl, $C_1$-$C_8$ alkyloxycarbonyloxy, halocarbonyl, aryl, hydroxy($C_1$-$C_8$)alkyl, $C_1$-$C_8$ alkyl, $C_1$-$C_8$ alkoxy, amino($C_1$-$C_8$)alkyl, $C_1$-$C_8$ alkylamino, di-($C_1$-$C_8$)alkylamino, $C_1$-$C_8$ alkyl($C_1$-$C_8$)alkoxy, $C_1$-$C_8$ alkoxy($C_1$-$C_8$)alkoxy, nitro, poly($C_1$-$C_8$) alkyl ether, ($C_1$-$C_8$)alkyl($C_1$-$C_8$)alkoxy($C_1$-$C_8$)alkyl, polyethyleneoxy, polypropyleneoxy, ethylene, acryloyl, acryloyloxy($C_1$-$C_{18}$)alkyl, methacryloyl, methacryloyloxy ($C_1$-$C_8$)alkyl, 2-chloroacryloyl, 2-phenylacryloyl, acryloyloxyphenyl, 2-chloroacryloylamino, 2-phenylacryloylaminocarbonyl, oxetanyl, glycidyl, cyano, isocyanato($C_1$-$C_{18}$) alkyl, itaconic acid ester, vinyl ether, and vinyl ester.

With further reference to Formulas (I), (II), and (III), and in accordance with some embodiments, $R_1$, independently for each q, is selected from hydrogen, linear or branched $C_1$-$C_6$ alkyl, and the group L. There is the proviso, with some embodiments, that at least one $R_1$ is said group L.

With further reference to Formulas (I), (II), and (III), and in accordance with some embodiments, $R_2$, $R_3$, $R_4$, and $R_5$, are each independently chosen in each case from hydrogen, linear or branched $C_1$-$C_6$ alkyl, $C_3$-$C_7$ cycloalkyl, unsubstituted phenyl, and substituted phenyl, where said phenyl substituents are selected from at least one of hydroxyl, halogen, and cyano, linear or branched $C_1$-$C_{10}$ alkyl, linear or branched $C_1$-$C_{10}$ alkoxy, and —N($R_9$)$R_{10}$, wherein $R_9$ and $R_{10}$ are each independently selected from hydrogen and linear or branched $C_1$-$C_{10}$ alkyl.

In accordance with some alternative embodiments, and with reference to Formulas (I), (II), and (III), $R_2$ and $R_3$ together form an optionally substituted $C_5$-$C_5$ cyclic ring optionally having one ethylenically unsaturated group in the cyclic ring.

In accordance with some further alternative embodiments, and with reference to Formulas (I), (II), and (III), $R_4$ and $R_5$ together form an optionally substituted $C_5$-$C_6$ cyclic ring optionally having one ethylenically unsaturated group in the cyclic ring.

In accordance with some additional embodiments, and with further reference to group L as represented by Formula (IV), (b) each $S_1$, $S_2$, $S_3$, $S_4$, and $S_5$ is independently chosen for each occurrence from a spacer unit selected from (ii) and (iii) as follows. With some embodiments, (b) each $S_1$, $S_2$, $S_3$, $S_4$, and $S_5$ is independently chosen for each occurrence from a spacer unit selected from (ii) —N(Z)—, —C(Z)=C(Z)—, and a single bond, wherein Z for each occurrence is independently selected from hydrogen, $C_1$-$C_8$ alkyl, $C_3$-$C_6$ cycloalkyl and aryl, and Z' for each occurrence is independently selected from $C_1$-$C_8$ alkyl, $C_3$-$C_6$ cycloalkyl and aryl. With some further embodiments, (b) each $S_1$, $S_2$, $S_3$, $S_4$, and $S_5$ is independently chosen for each occurrence from a spacer unit selected from (iii) —O—, —C(=O)—, —C≡C—, and straight-chain or branched $C_1$-$C_6$ alkylene residue, said $C_1$-$C_6$ alkylene residue being unsubstituted, mono-substituted by cyano or halogen, or poly-substituted by halogen.

With some further embodiments, and with further reference to group L as represented by Formula (IV), (c) P for each occurrence is independently selected from hydrogen, hydroxy, amino, $C_2$-$C_8$ alkenyl, $C_2$-$C_8$ alkynyl, and aryl.

With reference to Formulas (I), (II), and (III), $R_1$, independently for each q, is selected from hydrogen, linear or branched $C_1$-$C_6$ alkyl, and said group L, provided that one $R_1$ is said group L, and said group L is bonded to Position-8. With additional reference to Formulas (I), (II), and (III), B and B' are each independently selected from phenyl, phenyl substituted with $C_1$-$C_6$ alkoxy, phenyl substituted with halogen, phenyl substituted with morpholino, and phenyl substituted with piperidinyl.

In accordance with some embodiments, and with reference to Formulas (I), (II), and (III), the group L is in each case independently selected from the following Formulas (VII-A) through (VII-I):

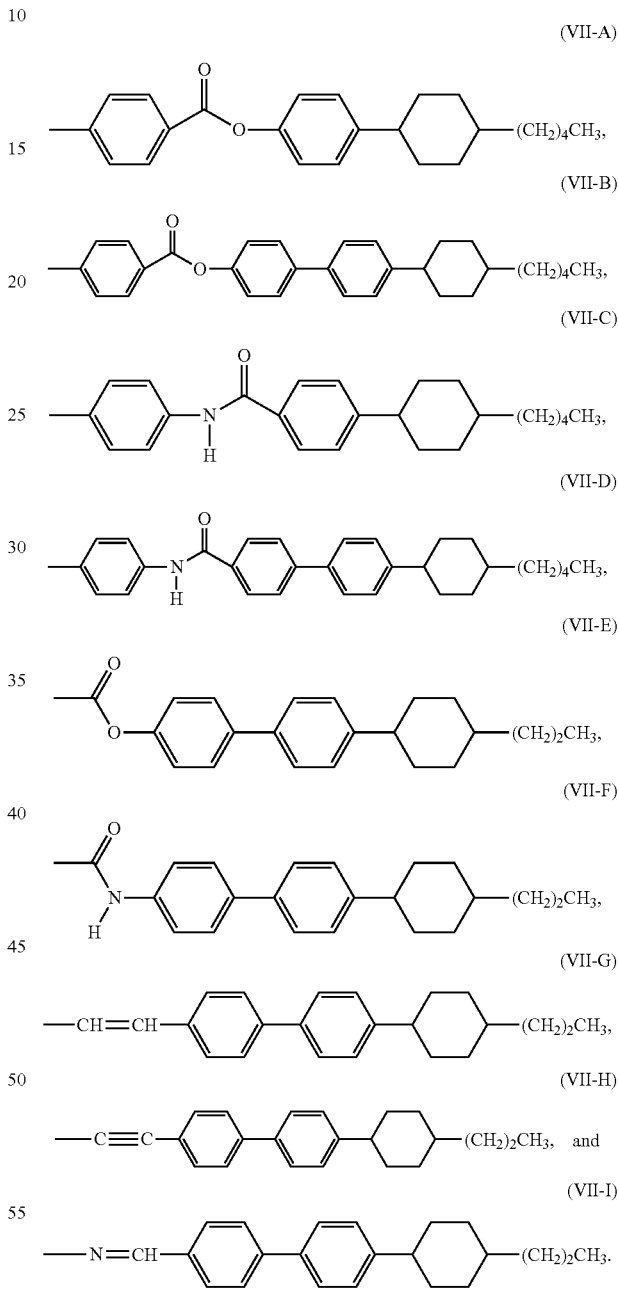

In accordance with some embodiments, the naphthopyran compound of the present invention, such as represented by Formulas (I), (II), and (III), is selected from at least one of:

2-(4-morpholinophenyl)-2-phenyl-9-(4-(4-(4-pentylcyclohexyl)phenyloxycarbonyl)phenyl)-2,5-dihydro-7-oxo-furo[3',4':3,4]naphtho[1,2-b]pyran, as represented by Formula (E-1) of the Examples;

2-(4-morpholinophenyl)-2,5,5-triphenyl-9-(4-(4-(4-pentylcyclohexyl)phenyloxycarbonyl)phenyl)-2,5-dihydro-7-oxo-furo[3',4':3,4]naphtho[1,2-b]pyran, as represented by Formula (E-2) of the Examples;

5,5-dimethyl-2-(4-morpholinophenyl)-2-phenyl-9-(4-(4-(4-pentylcyclohexyl)phenyloxycarbonyl)phenyl)-2,5-dihydro-7-oxo-furo[3',4':3,4]naphtho[1,2-b]pyran, as represented by Formula (E-3) of the Examples;

2-(4-morpholinophenyl)-2-phenyl-9-(4-(4-(4-pentylcyclohexyl)phenyloxycarbonyl)phenyl)-2,5-dihydro-7-oxo-spiro[cyclopent[3]ene-1',5-furo[3',4':3,4]naphtho[1,2-b]pyran, as represented by Formula (E-4) of the Examples;

2-(4-morpholinophenyl)-2-phenyl-9-(4-(4-(4-pentylcyclohexyl)phenyloxycarbonyl)phenyl)-2,5-dihydro-5-oxo-spiro[cyclopent[3]ene-1',7-furo[3',4':3,4]naphtho(1,2-b)pyran, as represented by Formula (E-5) of the Examples;

5,5-dimethyl-2-(2-fluorophenyl)-2-(4-morpholinophenyl)-9-(4-(4(4-pentylcyclohexyl)phenyloxycarbonyl)phenyl)-2,5-dihydro-7-oxo-furo[3',4':3,4]naphtho[1,2-b]pyran, as represented by Formula (E-6) of the Examples;

5,5-dimethyl-2-(2-fluorophenyl)-2-(4-morpholinophenyl)-9-(4-(4'-(4-pentylcyclohexyl)-[1,1'-biphenyl]-4-ylcarboxamido)phenyl)-2,5-dihydro-7-oxo-furo[3',4':3,4]naphtho[1,2-b]pyran, as represented by Formula (E-7) of the Examples;

5,5-dimethyl-2-(4-morpholinophenyl)-2-phenyl-9-(4-(4-(4-pentylcyclohexyl)phenyloxycarbonyl)phenyl)-2,5,7-trihydro-furo[3',4':3,4]naphtho[1,2-b]pyran, as represented by Formula (E-8) of the Examples;

5,5-dimethyl-2-(4-fluorophenyl)-2-(4-morpholinophenyl)-9-(4-(4-(4-pentylcyclohexyl)phenyloxycarbonyl)phenyl)-2,5,7-trihydro-furo[3',4':3,4]naphtho[1,2-b]pyran, as represented by Formula (E-9) of the Examples;

5,5-dimethyl-2,2-di-(methoxyphenyl)-9-(4-(4-(4-pentylcyclohexyl)phenyloxycarbonyl)phenyl)-2,5,7-trihydro-furo[3',4':3,4]naphtho[1,2-b]pyran, as represented by Formula (E-10) of the Examples;

5,5-dimethyl-2-(methoxyphenyl)-2-(4-morpholinophenyl)-9-(4-(4-(4-pentylcyclohexyl)phenyloxycarbonyl)phenyl)-2,5,7-trihydro-furo[3,4':3,4]naphtho[1,2-b]pyran, as represented by Formula (E-11) of the Examples; and 5,5-diethyl-2-(4-morpholinophenyl)-2-phenyl-9-(4-(4-(4-pentylcyclohexyl)phenyloxycarbonyl)phenyl)-2,5,7-trihydro-furo[3',4':3,4]naphtho[1,2-b]pyran, as represented by Formula (E-12) of the Examples.

In accordance with some embodiments, the naphthopyran compound of the present invention, such as represented by Formulas (I), (II), and (III), is a photochromic-dichroic naphthopyran compound. The photochromic-dichroic naphthopyran compounds of the present invention posses a combination of photochromic properties and dichroic properties, and can, with some embodiments, be used to prepare or as part of photochromic-dichroic articles.

In accordance with some embodiments of the present invention the naphthopyran compounds, including photochromic-dichroic naphthopyran compounds, of the present invention have at least a first state and a second state, in which the naphthopyran compound has an average dichroic ratio at least 1.5 in at least one state as determined according to the CELL METHOD, which is described in detail below. With some embodiments, the naphthopyran compounds, including photochromic-dichroic naphthopyran compounds of the present invention, have an average dichroic ratio at least 1.5 in an activated state as determined according to the CELL METHOD. As used herein with respect to naphthopyran compounds of the present invention, the term "activated state" refers to the naphthopyran compound when exposed to sufficient actinic radiation to cause at least a portion of the naphthopyran compound to switch states. Further, as used herein the term "compound" means a substance formed by the union of two or more elements, components, ingredients, or parts and includes, without limitation, molecules and macromolecules (for example polymers or oligomers) formed by the union of two or more elements, components, ingredients, or parts.

In general, the CELL METHOD of measuring average dichroic ratio of a photochromic-dichroic compound involves obtaining an absorption spectrum for the photochromic-dichroic compound, in an activated or unactived state, in each of two orthogonal polarization directions while the photochromic-dichroic compound is at least partially aligned in an aligned liquid crystal medium that is contained within a cell assembly. More specifically, the cell assembly includes two opposing glass substrates that are spaced apart by 20 microns+/−1 micron. The substrates are sealed along two opposite edges to form the cell. The inner surface of each of the glass substrates is coated with a polyimide coating, the surface of which has been at least partially ordered by rubbing. Alignment of the photochromic-dichroic compound is achieved by introducing the photochromic-dichroic compound and a liquid crystal medium into the cell assembly and allowing the liquid crystal medium to align with the rubbed polyimide surface. Because the photochromic-dichroic compound is contained within the liquid crystal medium, alignment of the liquid crystal medium causes the photochromic-dichroic compound to be aligned. The choice of the liquid crystal medium and the temperature used during testing can affect the measured dichroic ratio, as is recognized in the art. Accordingly, and with some embodiments, for purposes of the CELL METHOD, dichroic ratio measurements are taken at room temperature (73° F.+/−0.5° F. or better) and the liquid crystal medium is Licristal® E7 (which is reported to be a mixture of cyanobiphenyl and cyanoterphenyl liquid crystal compounds).

Once the liquid crystal medium and the photochromic-dichroic compound are aligned, the cell assembly is placed on an art-recognized optical bench. To obtain the average dichroic ratio in the activated state, activation of the photochromic-dichroic compound is achieved by exposing the photochromic-dichroic compound to UV radiation for a time sufficient to reach a saturated or near saturated state (i.e., a state wherein the absorption properties of the photochromic-dichroic compound do not substantially change over the interval of time during which the measurements are made). Absorption measurements are taken over a period of time (typically 10 to 300 seconds) at 3 second intervals for light that is linearly polarized in a plane perpendicular to the optical bench (referred to as the 0° polarization plane or direction) and light that is linearly polarized in a plane that is parallel to the optical bench (referred to as the 90° polarization plane or direction) in the following sequence: 0°, 90°, 90°, 0° etc. The absorbance of the linearly polarized light by the cell is measured at each time interval for all of the wavelengths tested and the unactivated absorbance (i.e., the absorbance of the cell with the liquid crystal material and the unactivated photochromic-dichroic compound) over the same range of wavelengths is subtracted to obtain absorption spectra for the photochromic-dichroic compound in each of the 0° and 90° polarization planes to obtain an average difference absorption spectrum in each polarization plane for the photochromic-dichroic compound in the saturated or near-saturated state.

For purposes of non-limiting illustration and with reference to FIG. 1, there is shown a representative average difference absorption spectrum (generally indicated 10) in one polarization plane that for a photochromic-dichroic compound. The average absorption spectrum (generally indicated 11) is the average difference absorption spectrum obtained for the same photochromic-dichroic compound in the orthogonal polarization plane.

Based on the average difference absorption spectra obtained for the photochromic-dichroic compound, the average dichroic ratio for the photochromic-dichroic compound is obtained as follows. The dichroic ratio of the photochromic-dichroic compound at each wavelength in a predetermined range of wavelengths corresponding to $\lambda_{max\text{-}vis}$ +/−5 nanometers (generally indicated as 14 in FIG. 1), wherein $\lambda_{max\text{-}vis}$ is the wavelength at which the photochromic compound had the highest average absorbance in any plane, is calculated according to the following equation:

$$DR_{\lambda,i} = Ab^1_{\lambda,i} / Ab^2_{\lambda,i} \qquad \text{Eq. 1}$$

wherein, $DR_{\lambda,i}$ is the dichroic ratio at wavelength $\lambda i$, $Ab^1_{\lambda,i}$ is the average absorption at wavelength $\lambda i$ in the polarization direction (i.e., 0° or 90°) having the higher absorbance, and $Ab^2_{\lambda,i}$ is the average absorption at wavelength $\lambda i$ in the remaining polarization direction. As previously discussed, the "dichroic ratio" refers to the ratio of the absorbance of radiation linearly polarized in a first plane to the absorbance of the same wavelength radiation linearly polarized in a plane orthogonal to the first plane, wherein the first plane is taken as the plane with the highest absorbance.

The average dichroic ratio ("DR") for the photochromic-dichroic compound is then calculated by averaging the individual dichroic ratios obtained for the wavelengths within the predetermined range of wavelengths (i.e., $\lambda_{max\text{-}vis}$ +/−5 nanometers) according to the following equation:

$$DR = (\lambda DR_{\lambda,i}) / n_i \qquad \text{Eq. 2}$$

wherein, DR is average dichroic ratio for the photochromic compound, $DR_{\lambda,i}$ are the individual dichroic ratios (as determined above in Eq. 1) for each wavelength within the predetermined the range of wavelengths (i.e., $\lambda_{max\text{-}vis}$ +/−5 nanometers), and n, is the number of individual dichroic ratios averaged.

Conventional thermally reversible photochromic compounds are adapted to switch from a first state to a second state in response to actinic radiation, and to revert back to the first state in response to thermal energy. More specifically, conventional thermally reversible, photochromic compounds are capable of transforming from one isomeric form (for example and without limitation, a closed form) to another isomeric form (for example and without limitation, an open form) in response to actinic radiation, and reverting back to the closed form when exposed to thermal energy. Generally, however, conventional thermally reversible photochromic compounds do not strongly demonstrate dichroism.

The naphthopyran compounds of the present invention, which can be photochromic-dichroic naphthopyran compounds, with some embodiments have an average dichroic ratio at least 1.5, such as from 1.5 to 50, or from 2 to 50, or from 3 to 30, or from 4 to 20, in at least one state as determined according to the CELL METHOD. It will be appreciated by those skilled in the art that the higher the average dichroic ratio of a photochromic-dichroic compound, the more linearly polarizing the photochromic-dichroic compound is. As such, in accordance with some embodiments, the naphthopyran compounds of the present invention, which can be photochromic-dichroic compounds, can have any average dichroic ratio required to achieve or provide a desired level of linear polarization.

In accordance with the present invention there is also provided a photochromic-dichroic article comprising one or more photochromic-dichroic naphthopyran compounds of the present invention, such as represented by Formulas (I), (II), and/or (III).

With some embodiments, the photochromic-dichroic article of the present invention is selected from ophthalmic articles, display articles, windows, mirrors, and active liquid crystal cell articles, and passive liquid crystal cell articles.

As used herein the term "liquid crystal cell" refers to a structure containing a liquid crystal material that is capable of being ordered. A non-limiting example of a liquid crystal cell element is a liquid crystal display.

As used herein the term "window" means an aperture adapted to permit the transmission of radiation there-through. Non-limiting examples of windows include automotive and aircraft transparencies, windshields, filters, shutters, and optical switches. As used herein the term "mirror" means a surface that specularly reflects a large fraction of incident light.

The photochromic-dichroic articles of the present invention are, with some embodiments, selected from ophthalmic articles, and the ophthalmic articles are selected from corrective lenses, non-corrective lenses, contact lenses, intra-ocular lenses, magnifying lenses, protective lenses, and visors.

Non-limiting examples of ophthalmic elements include corrective and non-corrective lenses, including single vision or multi-vision lenses, which can be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, magnifying lenses, protective lenses, visors, goggles, as well as, lenses for optical instruments (for example, cameras and telescopes).

With additional embodiments, the photochromic-dichroic articles of the present invention are selected from display articles, and the display articles are selected from screens, monitors, and security elements.

As used herein the term "display" means the visible or machine-readable representation of information in words, numbers, symbols, designs or drawings. Non-limiting examples of display elements include screens, monitors, and security elements, such as security marks.

Articles can be rendered photochromic or photochromic-dichroic with the naphthopyran compounds of the present invention by methods including, but not limited to, imbibition methods, cast-in-place methods, coating methods, in-mold coating methods, over-mold methods, and lamination methods. With imbibition methods, the naphthopyran compound is typically diffused into a host material, such as an organic host material, such as a polymeric material of a previously formed or fabricated article, such as a substrate or previously applied coating, film, and/or sheet. Imbibition can be performed by immersing the polymeric material of a previously formed or fabricated article in a solution containing the naphthopyran compound, with or without heating. Thereafter, although not required, the naphthopyran compound can be bonded with the polymeric material (e.g., of the substrate or coating).

With cast-in-place methods, and in accordance with some embodiments, the naphthopyran compound(s) can be mixed with: a polymer and/or oligomer composition in solution or melt form; or monomer composition in liquid form, so as to form a castable photochromic-dichroic composition. The castable photochromic-dichroic composition is then typically introduced into the cavity of a mold (e.g., a lens mold). The castable photochromic-dichroic composition is then set (e.g., cured) within the mold so as to form a photochromic-dichroic article.

With articles that include a substrate, the naphthopyran compounds of the present invention can be connected to at least a portion of the substrate as part of a coating that is connected to at least a portion of the substrate. The substrate can be a polymeric substrate or an inorganic substrate (such as, but not limited to, a glass substrate). The naphthopyran compound of the present invention can be incorporated into at least a portion of a coating composition prior to application of the coating composition to the substrate. Alternatively, a coating composition can be applied to the substrate, at least partially set, and thereafter the naphthopyran compound of the present invention can be imbibed into at least a portion of the coating. As used herein, the terms "set" and "setting" include, without limitation, curing, polymerizing, crosslinking, cooling, and drying.

Photochromic-dichroic articles can be prepared using the naphthopyran compounds of the present invention by art-recognized in-mold coating (or in-mold casting) methods. With in-mold coating methods, a photochromic-dichroic coating composition including the naphthopyran compound(s) of the present invention, which can be a liquid coating composition or a powder coating composition, is applied to at least a portion of the interior surface of a mold, and then at least partially set. Thereafter, a polymer solution or melt, or oligomeric or monomeric solution or mixture is cast or molded within the mold cavity and in contact with the previously applied photochromic coating composition, and at least partially set. The resulting photochromic-dichroic article is then removed from the mold. Non-limiting examples of powder coatings in which the naphthopyran compounds according to various non-limiting embodiments of the present invention can be employed are set forth in U.S. Pat. No. 6,068,797 at col. 7, line 50 to col. 19, line 42, which disclosure is hereby specifically incorporated by reference herein.

Photochromic-dichroic articles prepared using the naphthopyran compounds of the present invention can also be formed by art-recognized over-mold methods. Over-mold methods typically involve forming a substrate within a mold, and then forming an interior space between the substrate and an interior surface of the mold, into which a photochromic-dichroic coating composition is then subsequently introduced (e.g., injected) and then set (e.g., cured). Alternatively, over-mold methods can involve introducing a previously formed substrate into a mold, such that an interior space is defined between the substrate and an interior mold surface, and thereafter a photochromic-dichroic coating composition is introduced (e.g., injected) into the interior space.

Photochromic-dichroic articles, prepared using the naphthopyran compounds of the present invention, can also be formed by art-recognized lamination methods. With lamination methods, a film comprising the naphthopyran compounds of the present invention can be adhered or otherwise connect to a portion of the substrate, with or without an adhesive and/or the application of heat and pressure. Thereafter, if desired, a second substrate can be applied over the first substrate and the two substrates can be laminated together (e.g., by the application of heat and pressure) to form an element wherein the film comprising the naphthopyran compound is interposed between the two substrates. Methods of forming films comprising a photochromic-dichroic material can include for example and without limitation, combining a photochromic-dichroic material with a polymeric solution or oligomeric solution or mixture, casting or extruding a film therefrom, and, if required, at least partially setting the film. Additionally or alternatively, a film can be formed (with or without a photochromic material) and imbibed with the photochromic material.

The photochromic-dichroic articles according to some embodiments of the present invention can include a host material, such as an organic host material, that can, with some embodiments be in the form of a substrate. With some embodiments, the organic host material can be chosen from a polymeric material, an oligomeric material and/or a monomeric material. Examples of polymeric materials that can be used as a host material of the photochromic-dichroic articles of the present invention include, but are not limited to: polymers of bis(allyl carbonate) monomers; diethylene glycol dimethacrylate monomers; diisopropenyl benzene monomers; ethoxylated bisphenol A dimethacrylate monomers; ethylene glycol bismethacrylate monomers; poly(ethylene glycol)bismethacrylate monomers; ethoxylated phenol bismethacrylate monomers; alkoxylated polyhydric alcohol acrylate monomers, such as ethoxylated trimethylol propane triacrylate monomers; urethane acrylate monomers; vinylbenzene monomers; and styrene. Other non-limiting examples of suitable polymeric materials include polymers of polyfunctional, e.g., mono-, di- or multi-functional, acrylate and/or methacrylate monomers; poly($C_1$-$C_{12}$ alkyl methacrylates), such as poly(methyl methacrylate); poly(oxyalkylene) dimethacrylate; poly(alkoxylated phenol methacrylates); cellulose acetate; cellulose triacetate; cellulose acetate propionate; cellulose acetate butyrate; poly(vinyl acetate); poly(vinyl alcohol); poly(vinyl chloride); poly(vinylidene chloride); polyurethanes; polythiourethanes; thermoplastic polycarbonates; polyesters; poly(ethylene terephthalate); polystyrene; poly(alpha-methylstyrene); copolymers of styrene and methyl methacrylate; copolymers of styrene and acrylonitrile; polyvinylbutyral; and polymers of diallylidene pentaerythritol, particularly copolymers with polyol (allyl carbonate) monomers, e.g., diethylene glycol bis(allyl carbonate), and acrylate monomers, e.g., ethyl acrylate, butyl acrylate. Also contemplated are copolymers of the aforementioned monomers, combinations, and blends of the aforementioned polymers and copolymers with other polymers, such as in the form of interpenetrating network materials.

In accordance with some embodiments the organic host material can be a transparent polymeric material. For example, according to various non-limiting embodiments, the polymeric material can be an optically clear polymeric material prepared from a thermoplastic polycarbonate resin, such as the resin derived from bisphenol A and phosgene, which is sold under the trademark, LEXAN®; a polyester, such as the material sold under the trademark, MYLAR®; a poly(methyl methacrylate), such as the material sold under the trademark, PLEXIGLAS®; and polymerizates of a polyol (allyl carbonate) monomer, especially diethylene glycol bis (allyl carbonate), which monomer is sold under the trademark CR-39®; and polyurea-polyurethane (polyurea urethane) polymers, which are prepared, for example, by the reaction of a polyurethane oligomer and a diamine curing agent, a composition for one such polymer being sold under the trademark TRIVEX® by PPG Industries, Inc. Other non-limiting examples of suitable polymeric materials include polymerizates of copolymers of a polyol (allyl carbonate), e.g., diethylene glycol bis(allyl carbonate), with other copolymerizable monomeric materials, such as, but not limited to: copolymers with vinyl acetate, copolymers with a polyurethane having terminal diacrylate functionality, and copolymers with aliphatic urethanes, the terminal portion of which contain allyl or acrylyl functional groups. Still other suitable polymeric materials include, without limitation, poly(vinyl acetate), polyvinylbutyral, polyurethane, polythiourethanes, polymers chosen from diethylene glycol dimethacrylate monomers, diisopropenyl benzene monomers, ethoxylated bisphenol A dimethacrylate monomers, ethylene glycol bismethacrylate monomers, poly(ethylene glycol)bismethacrylate monomers, ethoxylated phenol bismethacrylate monomers and ethoxylated trimethylol propane triacrylate monomers, cellulose acetate, cellulose propionate, cellulose butyrate, cellulose acetate butyrate, polystyrene and copolymers of styrene with methyl methacrylate, vinyl acetate and acrylonitrile. According to one non-limiting embodiment, the polymeric material can be an optical resins sold by PPG Industries, Inc. under the CR-designation, e.g., CR-307, CR-407, and CR-607.

In accordance with some embodiments, the organic host material can be a polymeric material which is chosen from poly(carbonate), copolymers of ethylene and vinyl acetate; copolymers of ethylene and vinyl alcohol; copolymers of ethylene, vinyl acetate, and vinyl alcohol (such as those that result from the partial saponification of copolymers of ethylene and vinyl acetate); cellulose acetate butyrate; poly(urethane); poly(acrylate); poly(methacrylate); epoxies; aminoplast functional polymers; poly(anhydride); poly(urea urethane); N-alkoxymethyl(meth)acrylamide functional polymers; poly(siloxane); poly(silane); and combinations and mixtures thereof.

The naphthopyran compounds of the present invention, can be used alone or in combination with other photochromic materials. Classes of photochromic materials that can be used in combination (e.g., in mixture) with the naphthopyran compounds of the present invention include, but are not limited to: spiro(indoline)naphthoxazines and spiro(indoline)benzoxazines, for example as described in U.S. Pat. Nos. 3,562,172, 3,578,602, 4,215.010, 4,342,668, 5,405,958, 4,637,698, 4,931,219, 4,816,584, 4,880,667, and 4,818,096; benzopyrans, for example as described in U.S. Pat. Nos. 3,567,605, 4,826,977, 5,066,818, 4,826,977, 5,066,818, 5,466,398, 5,384,077, 5,238,931, and 5,274,132; photochromic organometal dithizonates, such as, (arylazo)-thioformic arylhydrazidates, e.g., mercury dithizonates which are described in, for example, U.S. Pat. No. 3,361,706; and fulgides and fulgimides, e.g., the 3-furyl and 3-thienyl fulgides and fulgimides which are described in U.S. Pat. No. 4,931,220 at column 20, line 5 through column 21, line 38.

The present invention also relates to a photochromic-dichroic composition that includes: (a) a naphthopyran compound of the present invention; and at least one of (b-i) an organic material selected from a polymer, an oligomer, a monomer, and combinations of two or more thereof; and (b-ii) a solvent. The polymer of the photochromic-dichroic composition can be selected from, with some embodiments, polycarbonate, polyamide, polyimide, poly(meth)acrylate, polycyclic alkene, polyurethane, poly(urea)urethane, polythiourethane, polythio(urea)urethane, polyol(allyl carbonate), cellulose acetate, cellulose diacetate, cellulose triacetate, cellulose acetate propionate, cellulose acetate butyrate, polyalkene, polyalkylene-vinyl acetate, poly(vinylacetate), poly(vinyl alcohol), poly(vinyl chloride), poly(vinylformal), poly(vinylacetal), poly(vinylidene chloride), poly(ethylene terephthalate), polyester, polysulfone, polyolefin, copolymers thereof, and combinations thereof. Examples of oligomers that can be included in the photochromic-dichroic composition include, but are not limited to, oligomeric versions of the previously recited polymers, with some embodiments.

Examples of monomers that can be included in the photochromic-dichroic composition include, but are not limited to, ethylenically unsaturated radically polymerizable monomer. As used herein, the term "ethylenically unsaturated radically polymerizable monomer" and similar terms includes, but are not limited to, vinyl monomers, allylic monomers, olefins and other ethylenically unsaturated monomers that are radically polymerizable.

Classes of vinyl monomers that can be included in the photochromic-dichroic composition include, but are not limited to, (meth)acrylates, vinyl aromatic monomers, vinyl halides, and vinyl esters of carboxylic acids, each of which can, with some embodiments, optionally include one or more functional groups selected from hydroxyl groups, thiol groups, primary amine groups, secondary amine groups, and oxirane groups. With some embodiments, the (meth)acrylates are selected from at least one of: alkyl(meth)acrylates having from 1 to 20 carbon atoms in the alkyl group; and alkyl(meth)acrylates having from 1 to 20 carbon atoms in the alkyl group, in which the alkyl group includes or is substituted with one or more functional groups selected from hydroxyl groups, thiol groups, primary amine groups, secondary amine groups, and oxirane groups. Examples of alkyl(meth)acrylates having from 1 to 20 carbon atoms in the alkyl group that can be used include, but are not limited to, methyl(meth)acrylate, ethyl(meth)acrylate, propyl(meth)acrylate, isopropyl(meth)acrylate, butyl(meth)acrylate, isobutyl(meth)acrylate, tert-butyl(meth)acrylate, 2-ethylhexyl(meth)acrylate, lauryl(meth)acrylate, isobornyl(meth)acrylate, cyclohexyl(meth)acrylate and 3,3,5-trimethylcyclohexyl(meth)acrylate, one or more of which can, with some embodiments, optionally include in the alkyl group thereof one or more functional groups selected from hydroxyl groups, thiol groups, primary amine groups, secondary amine groups, and oxirane groups.

Examples of oxirane functional monomers that can be included in the photochromic-dichroic composition include, but are not limited to, glycidyl(meth)acrylate, 3,4-epoxycyclohexylmethyl(meth)acrylate, 2-(3,4-epoxycyclohexyl)ethyl(meth)acrylate and allyl glycidyl ether. With some embodiments, oxirane functionality can be incorporated into the polymer by post-reaction, such as by preparing a hydroxyl functional precursor polymer and converting the precursor polymer to an oxirane functional polymer by reacting at least some of the hydroxyl groups with epichlorohydrin, in accordance with art-recognized methods.

Examples of vinyl aromatic monomers that can be included in the photochromic-dichroic composition include, but are not limited to, styrene, p-chloromethylstyrene, divinyl benzene, vinyl naphthalene and divinyl naphthalene. Vinyl halides from which each M can be independently derived include, but are not limited to, vinyl chloride and vinylidene fluoride. Vinyl esters of carboxylic acids include, but are not limited to, vinyl acetate, vinyl butyrate, vinyl 3,4-dimethoxybenzoate and vinyl benzoate.

As used herein, by "olefin" and like terms is meant unsaturated aliphatic hydrocarbons having one or more double bonds, such as obtained by cracking petroleum fractions. Examples of olefins that can be included in the photochromic-dichroic composition include, but are not limited to, propylene, 1-butene, 1,3-butadiene, isobutylene and diisobutylene.

As used herein, by "allylic monomer(s)" is meant monomers containing substituted and/or unsubstituted allylic functionality, such as one or more radicals represented by the following Formula (VIII), $$H_2C=C(R^1)-CH_2-\qquad\qquad(VIII)$$

With reference to Formula (VIII), $R^1$ is hydrogen, halogen or a $C_1$ to $C_4$ alkyl group. With some embodiments, $R^1$ is hydrogen or methyl and consequently Formula (VII) represents an unsubstituted(meth)allyl radical. Examples of allylic monomers include, but are not limited to: (meth)allyl alcohol; (meth)allyl ethers, such as methyl(meth)ally ether; allyl esters of carboxylic acids, such as (meth)allyl acetate, (meth)allyl butyrate, (meth)allyl 3,4-dimethoxybenzoate and (meth)allyl benzoate.

Other ethylenically unsaturated radically polymerizable monomers that can be included in the photochromic-dichroic composition include, but are not limited to: cyclic anhydrides, such as maleic anhydride, 1-cyclopentene-1,2-dicarboxylic anhydride and itaconic anhydride; esters of acids that are unsaturated but do not have alpha, beta-ethylenic unsaturation, such as methyl ester of undecylenic acid; and diesters of ethylenically unsaturated dibasic acids, such as diethyl maleate.

The photochromic-dichroic compositions of the present invention can, with some embodiments, include one or more solvents, selected from water, organic solvents, and combinations thereof.

Classes of organic solvents that can be present in photochromic-dichroic compositions of the present invention include, but are not limited to: alcohols, e.g., methanol, ethanol, n-propanol, iso-propanol, n-butanol, sec-butyl alcohol, tert-butyl alcohol, iso-butyl alcohol, furfuryl alcohol and tetrahydrofurfuryl alcohol; ketones or ketoalcohols, e.g., acetone, methyl ethyl ketone, and diacetone alcohol; ethers, e.g., dimethyl ether and methyl ethyl ether, cyclic ethers, e.g., tetrahydrofuran and dioxane; esters, e.g., ethyl acetate, ethyl lactate, ethylene carbonate and propylene carbonate; polyhydric alcohols, e.g., ethylene glycol, diethylene glycol, triethylene glycol, propylene glycol, tetraethylene glycol, polyethylene glycol, glycerol, 2-methyl-2,4-pentanediol and 1,2,6-hexantriol; hydroxy functional ethers of alkylene glycols, e.g., butyl 2-hydroxyethyl ether, hexyl 2-hydroxyethyl ether, methyl 2-hydroxypropyl ether and phenyl 2-hydroxypropyl ether; nitrogen containing cyclic compounds, e.g., pyrrolidone, N-methyl-2-pyrrolidone and 1,3-dimethyl-2-imidazolidinone; and sulfur containing compounds—such as thioglycol, dimethyl sulfoxide and tetramethylene sulfone.

Solvent(s) can be present in the photochromic-dichroic compositions of the present invention, in an amount of at least 5 percent by weight, or at least 15 percent by weight, or at least 30 percent by weight, based on the total weight of the photochromic-dichroic compositions. The solvent(s) can also be present in the photochromic-dichroic compositions in an amount of less than 95 percent by weight, or less than 80 percent by weight, or less than 60 percent by weight, based on the total weight of the photochromic-dichroic compositions. The amount of solvent present in the photochromic-dichroic compositions can range between any combination of these values, inclusive of the recited values, with some embodiments, such as from 5 to 95 percent by weight, or from 15 to 80 percent by weight, or from 30 to 60 percent by weight, in each case based on the total weight of the photochromic-dichroic compositions.

The photochromic-dichroic compositions of the present invention can optionally further include, at least one additive selected from dyes, alignment promoters, photoinitiators, thermal initiators, polymerization inhibitors, solvents, light stabilizers, heat stabilizers, mold release agents, rheology control agents, leveling agents, free radical scavengers, and adhesion promoters. Additives can be present in the photochromic-dichroic compositions of the present invention in an effective amount, such as up to 40% by weight, or up to 20% by weight, or up to 10% by weight, based on total solids weight of the composition.

The present invention also relates to a photochromic-dichroic coating composition that includes: (a) a naphthopyran compound of the present invention; (b) a film forming composition selected from a curable resin composition, a thermoplastic resin composition, and combinations thereof; and (c) optionally a solvent composition. The solvent can be selected from one or more solvents, and can be present in amounts as described with regard to the photochromic-dichroic compositions of the present invention.

The curable film forming composition includes, with some embodiments: (i) a first reactant selected from one or more polymers and/or oligomers and/or monomers as described previously herein with regard to the photochromic-dichroic compositions of the present invention, in which the first reactant includes one or more, such as at least two, first reactive group(s); and (ii) a crosslinking agent that has at least two second reactive groups that are reactive with the first reactive groups of the first reactant.

With some embodiments, the first reactant of the film forming composition has at least two active hydrogen groups selected from hydroxyl, thiol, carboxylic acid, primary amine, and secondary amine; and the crosslinking agent includes at least two functional groups selected from cyclic carboxylic acid anhydrides, oxiranes, thiooxiranes, isocyanates, thioisocyanates, cyclic carboxylic acid esters, cyclic amides, and cyclic carbonates.

With some additional embodiments, the first reactant of the film forming composition has at least two functional groups selected from cyclic carboxylic acid anhydrides, oxiranes, thiooxiranes, isocyanates, thioisocyanates, cyclic carboxylic acid esters, cyclic amides, and cyclic carbonates; and the crosslinking agent has at least two active hydrogen groups selected from hydroxyl, thiol, carboxylic acid, primary amine, and secondary amine.

The photochromic-dichroic coating compositions of the present invention can include one or more additives, which can be selected from and present in amounts as described with regard to the photochromic-dichroic compositions of the present invention.

The photochromic-dichroic coating compositions of the present invention can be cured, with some embodiments, by exposure to elevated temperature, such as a temperature within the range of 90° C. to 204° C., or from 149° C. to 204° C., or from 154° C. to 177° C., for a period of 20 to 60 minutes, inclusive of the recited values.

The relative amounts of the naphthopyran compound(s) of the present invention and optional photochromic compound(s) used can vary and depend in part upon the relative intensities of the color of the activated species of such compounds, and the ultimate color desired, with some embodiments. With some embodiments, the amount of total naphthopyran compound(s) of the present invention and optional photochromic compound(s) incorporated into or applied to a photochromic-dichroic article (such as a substrate of the resulting photochromic-dichroic article) can range from 0.05 to 2.0, or from 0.2 to 1.0, milligrams per square centimeter of surface of the photochromic-dichroic article. The amount of naphthopyran compound(s) of the present invention and optional photochromic compound(s) incorporated into a photochromic-dichroic composition or a photochromic-dichroic coating composition of the present invention can range from 0.1 to 40 weight percent, based on the weight of the photochromic-dichroic composition or the photochromic-dichroic coating composition, with some embodiments.

For purposes of non-limiting illustration, the naphthopyran compounds of the present invention, such as represented by Formulas (I), (II), and (III) can be prepared in accordance with the following general descriptions, which are made with reference to synthetic Schemes 1-7 of FIGS. 2-8 of the drawings.

In Schemes 1-7 (of FIGS. 2-8) the following abbreviations have the following meanings:
Et$_3$N means triethylamine;
RM means organometallic compounds;
KF means potassium fluoride;
THF means tetrahydrofuran;
Suzuki means the art-recognized Suzuki reaction;
DCC means N,N'-dicyclohexylcarbodiimide;
DMAP means 4-(Dimethylamino)pyridine;
dppf means 1,1'-bis(diphenylphosphino)ferrocene;
Pd$_2$(dba)$_3$ means tris(dibenzylideneacetone)dipalladium(O);
DIBAL means diisobutylaluminium hydride;
mCPBA means meta-chloroperoxybenzoic acid;
TBAF means tetra-n-butylammonium fluoride; and
BINAP means 2,2'-bis(diphenylphosphino)-1,1'-binaphthyl.

Figure 2:
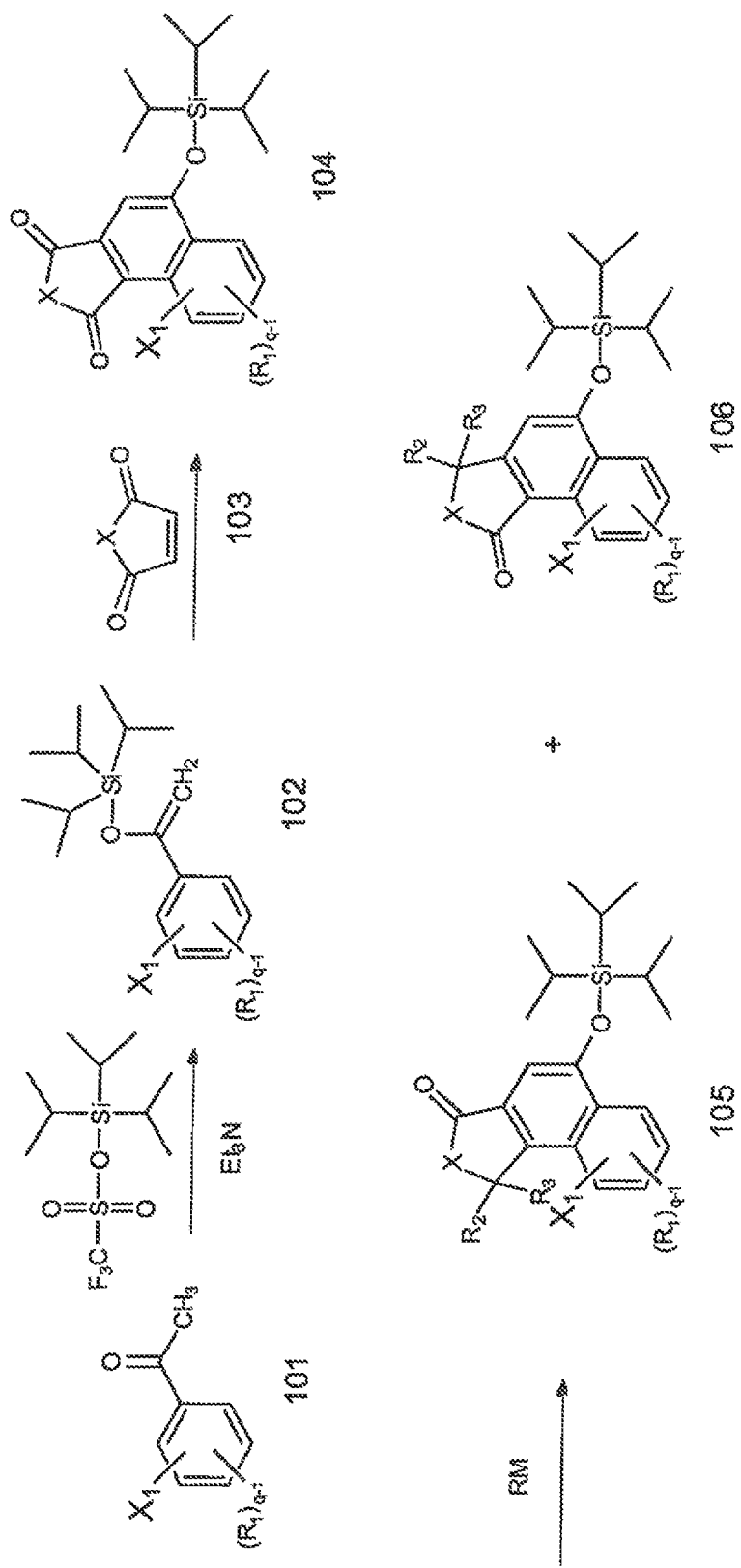
FIG. 2 is a representative synthetic scheme (Scheme 1) by which some intermediates compounds can be prepared, which can be used to prepare naphthopyran compounds of the present invention.

With reference to Scheme 1 of FIG. 2 of the drawings, there is depicted the preparation of intermediates 105 and 106, which can be used to prepare naphthopyran compounds according to the present invention. Formation of 104 begins with the synthesis of the protected enol ether 102 from a substituted acetophenone 101 where $X_1$ is at least a halogen. The precursor 102 undergoes a [4+2]cycloaddition with an appropriate cyclic anhydride (X=O) or imide (X=N) 103 with the resulting cycloadduct being oxidized in situ by chloranil to provide 104 (See Sato et al. Bull. Chem. Soc. Jpn. 1988, 61, 2238). Treatment of 104 with an alkyl metal (Li, Mg, La, Zn or a mixture) or reducing agent (See: a) Bailey, D. M.; Johnson, R. E. *J. Org. Chem.* 1970, 35, 3574; b) Horii, Z.-I.; Iwata, C.; Tamura, Y. *J. Org. Chem.* 1961, 26, 2273) provides a mixture of reduced products, 105 and 106, which can be separated by chromatography.

Figure 3:
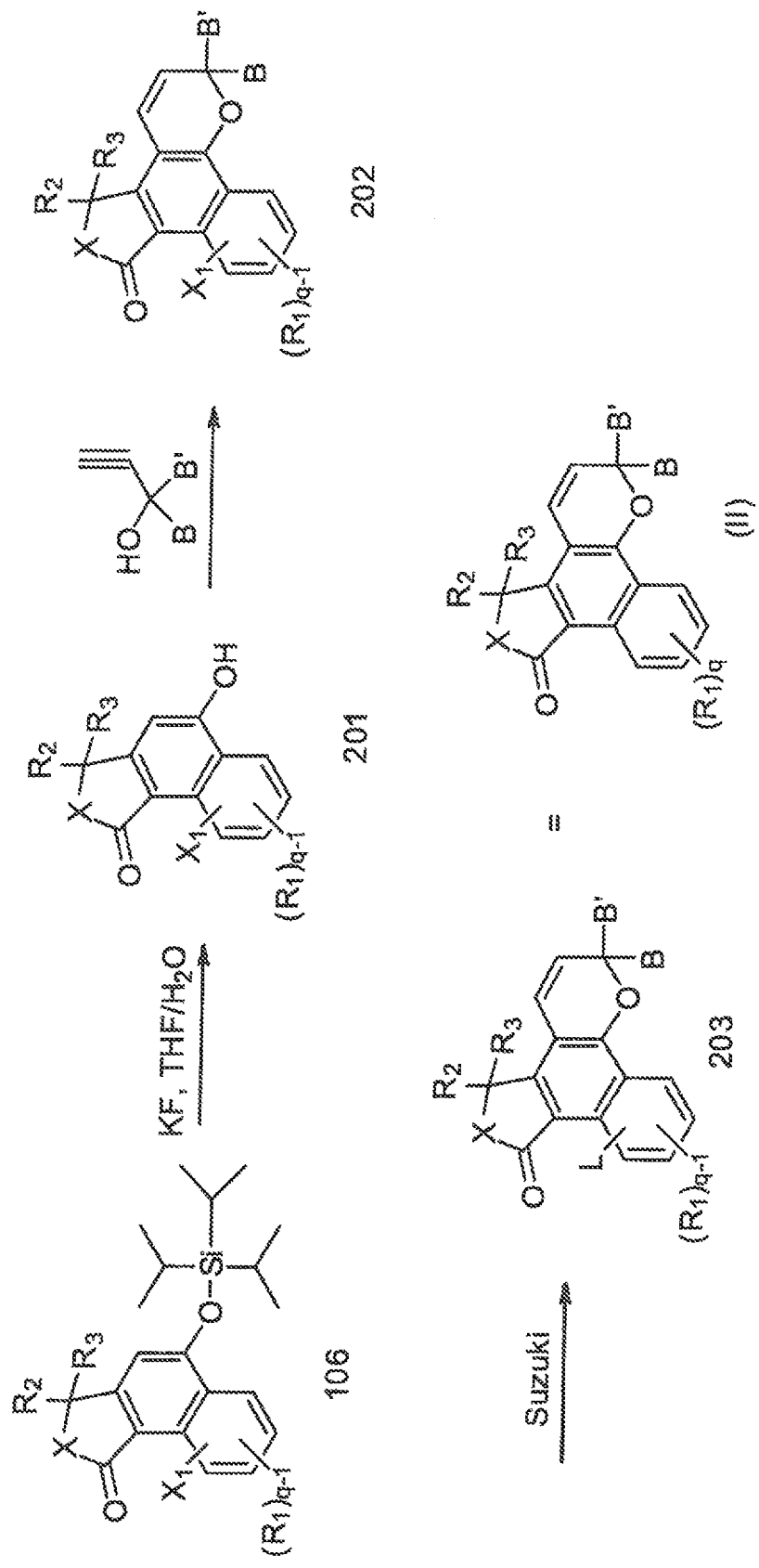
FIG. 3 is a representative synthetic scheme (Scheme 2) by which an intermediate compound of Scheme 1 can be converted to naphthopyran compounds according to the present invention.
Figure 4:
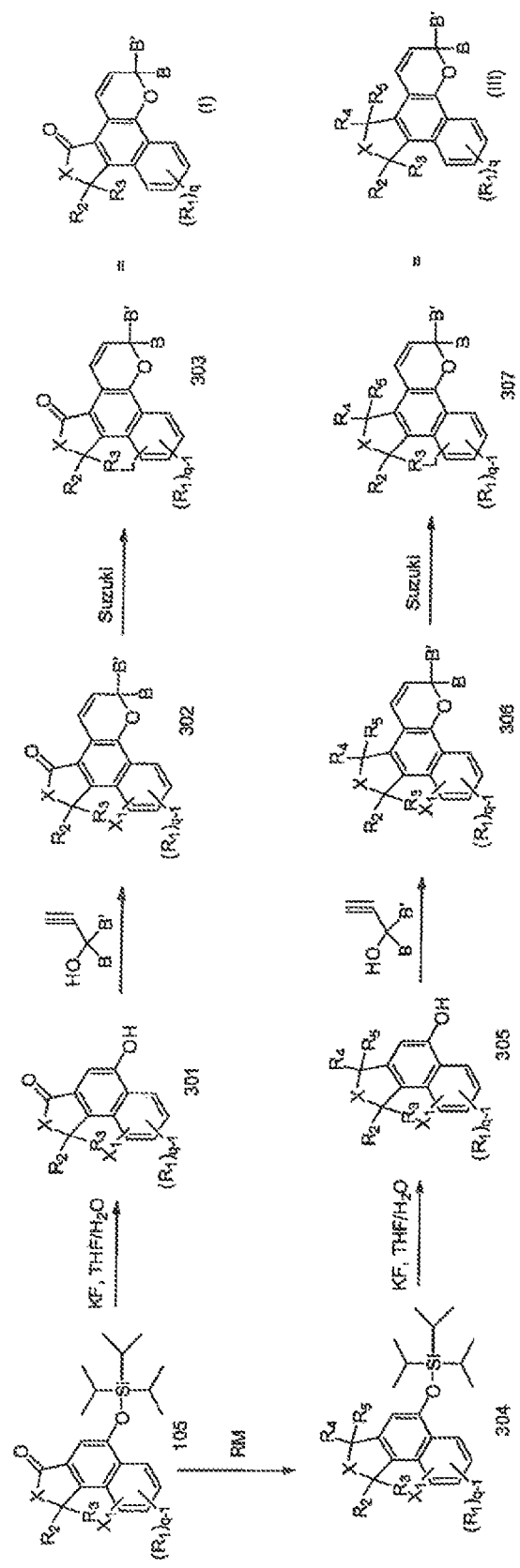
FIG. 4 is a representative synthetic scheme (Scheme 3) by which an intermediate compound of Scheme 1 can be converted to naphthopyran compounds according to the present invention.
Figure 5:
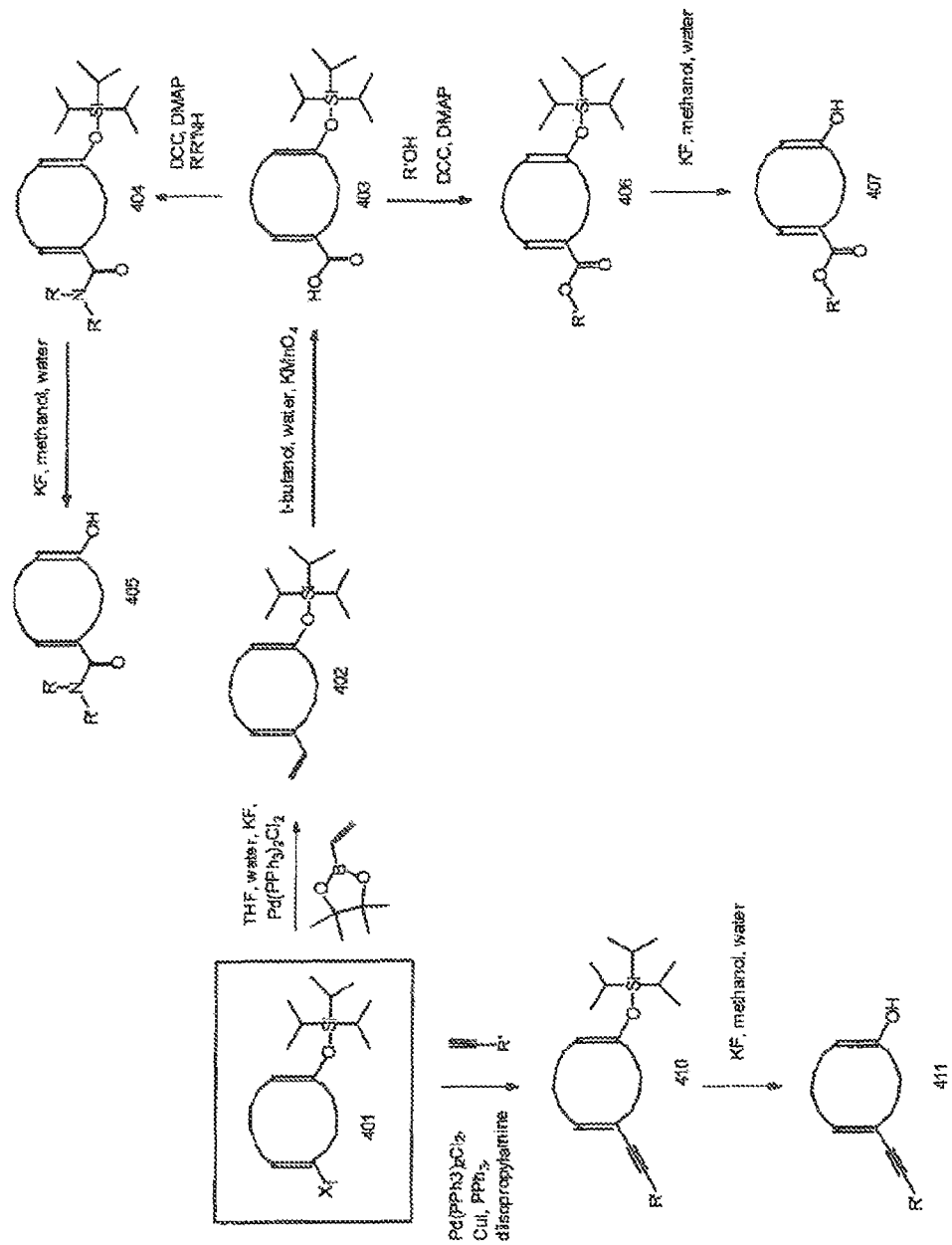
FIG. 5 is a representative synthetic scheme (Scheme 4) by which intermediate compounds can be prepared, which can be converted to naphthopyran compounds according to the present invention using the propargyl alcohol chemistry depicted in Schemes 2 and 3.
Figure 6:
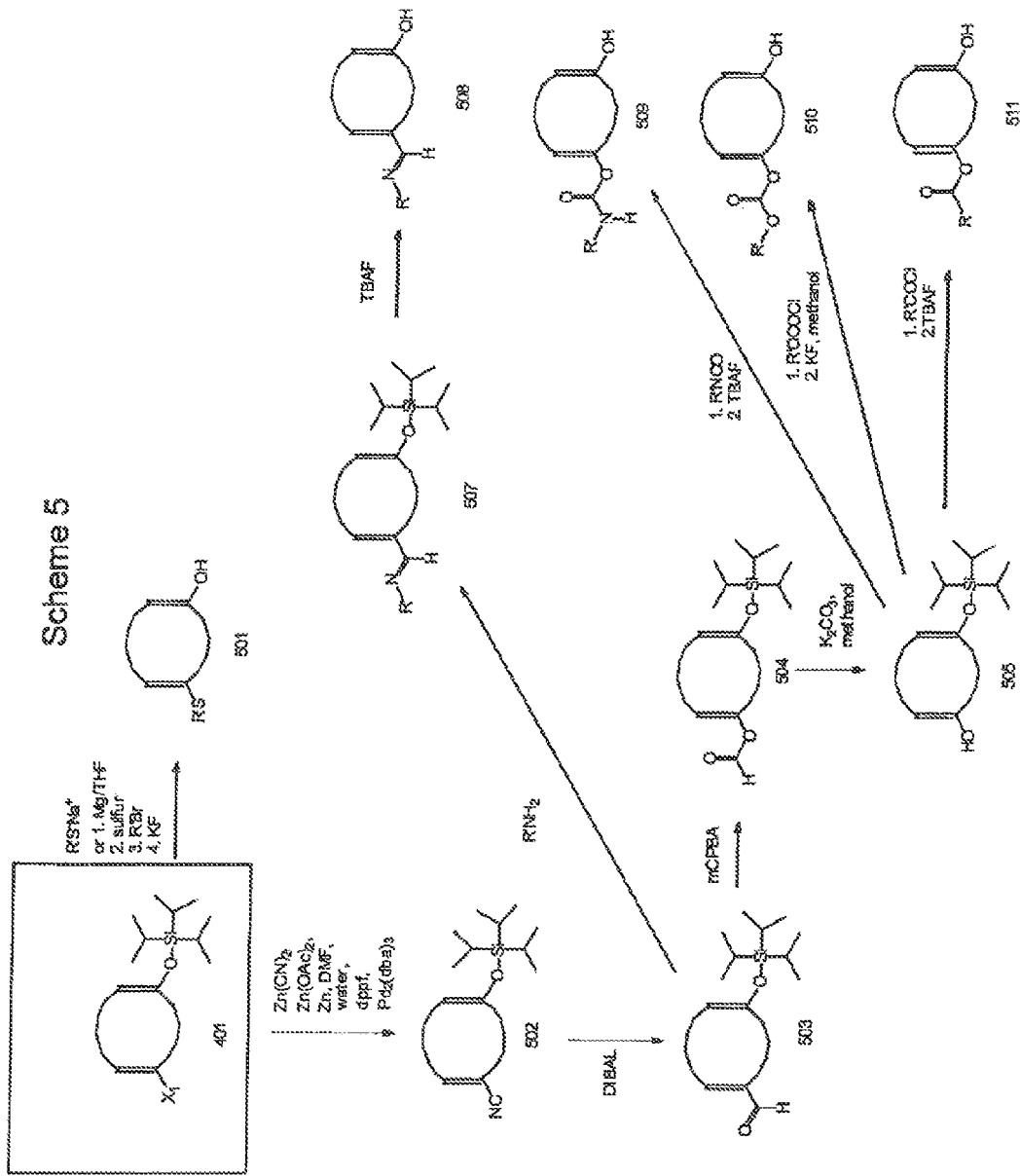
FIG. 6 is a representative synthetic scheme (Scheme 5) by which intermediate compounds can be prepared, which can be converted to naphthopyran compounds according to the present invention using the propargyl alcohol chemistry depicted in Schemes 2 and 3.
Figure 7:
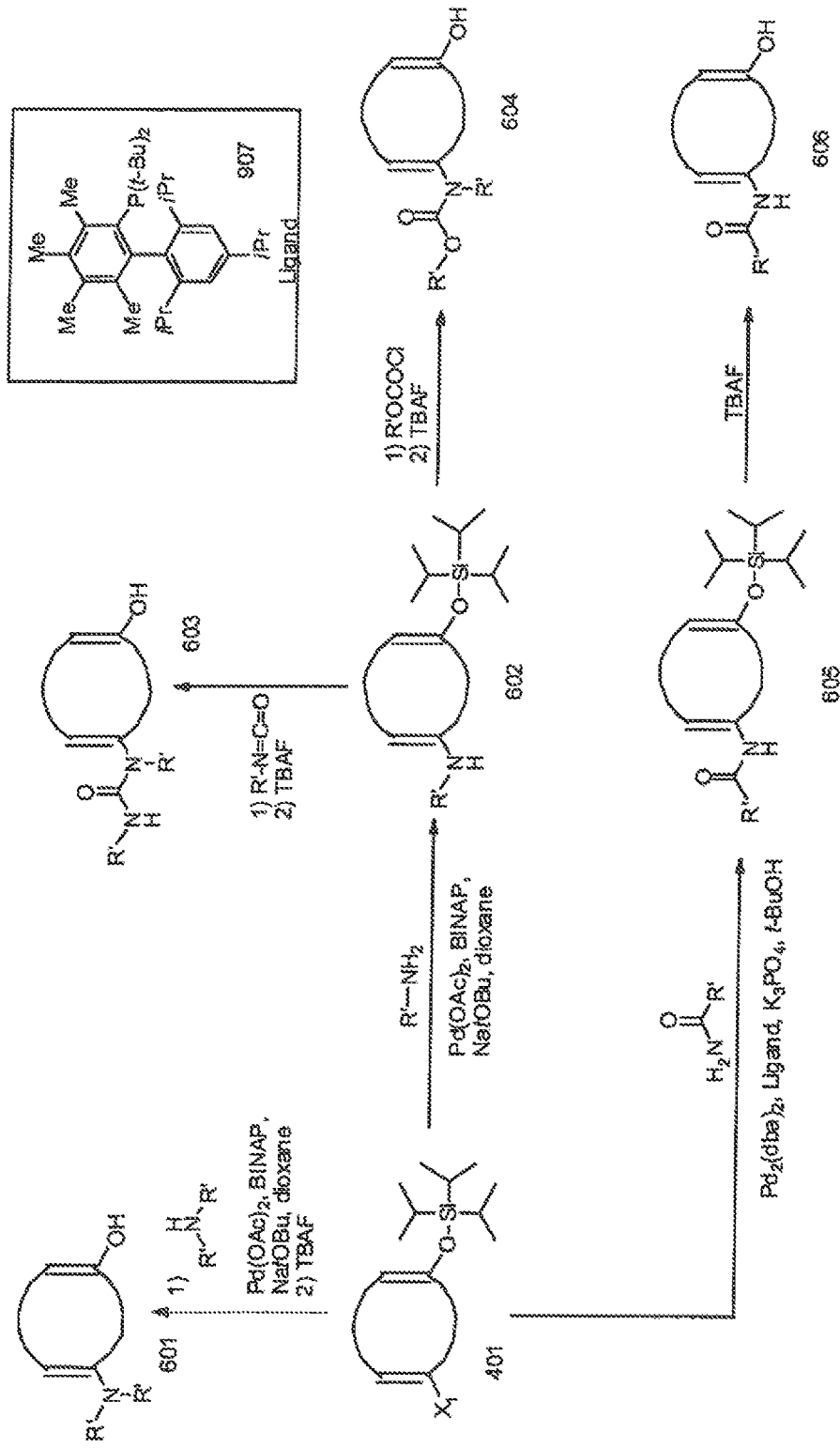
FIG. 7 is a representative synthetic scheme (Scheme 6) by which intermediate compounds can be prepared, which can be converted to naphthopyran compounds according to the present invention using the propargyl alcohol chemistry depicted in Schemes 2 and 3.

With reference to Schemes 2 and 3 of FIGS. 3 and 4, there are depicted methods of converting intermediates 105 and 106 to naphthopyran compounds according to Formulas (I), (II) and (III).

With reference to Scheme 3 of FIG. 4, removal of the protecting group from 105 and 106, followed by treatment of the naphthols with propargylic alcohol provides 202 and 303. Installation of the lengthening group L by Suzuki coupling of 202 and 303 provides structures according to Formulas (I) and (II) (Schemes 2 and 3 of FIGS. 3 and 4). Intermediate 105 can be further treated with an alkyl metal or reducing agent to provide 304. Deprotection of 304 followed by treatment of the naphthol with propargylic alcohol provides 306. Installation of the lengthening group L by Suzuki coupling of 306 provides naphthopyran compounds according to Formula (III) (Scheme 3).

With reference to Schemes 2 and 3 (of FIGS. 3 and 4) $S_1$ of L of Formula (IV) is a single bond. With reference to Schemes 4-7 (FIGS. 5-8), the preparation of naphthopyran compounds in which S of L of Formula (IV) is other than single bond, is depicted.

With reference to Schemes 4 to 7 (of FIGS. 5-8), R' represents the following portion of L of Formula (IV), as represented by the following Formula (IV-a),

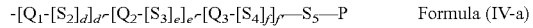
-[Q₁-[S₂]_d]_d'-[Q₂-[S₃]_e]_e'-[Q₃-[S₄]_f]_f'—S₅—P     Formula (IV-a)

For purposes of illustration and with reference to compound 411 of Scheme 4, R' is represented by Formula (IV-a) above, and with further reference to Formula (IV), c is 1, and S1 is —C≡C—.

Schemes 4 to 6 (of FIGS. 5-7) illustrate details of converting halogen to other functional groups that are either lengthening group L themselves or can be further converted to lengthening group L. The chemistries are done at the protected (silyl ether) hydroxy stage starting from compounds 105, 106 and 304, which is simplified as compound 401 in Schemes 4, 5 and 6. Each of the hydroxy products of compounds 405, 407, 411, 501, 508, 509, 510, 511, 601, 603, 604 and 606 can be converted to naphthopyran compounds according to the present invention using the propargyl alcohol chemistry shown in Schemes 2 and 3 (of FIGS. 3 and 4).

Figure 8:
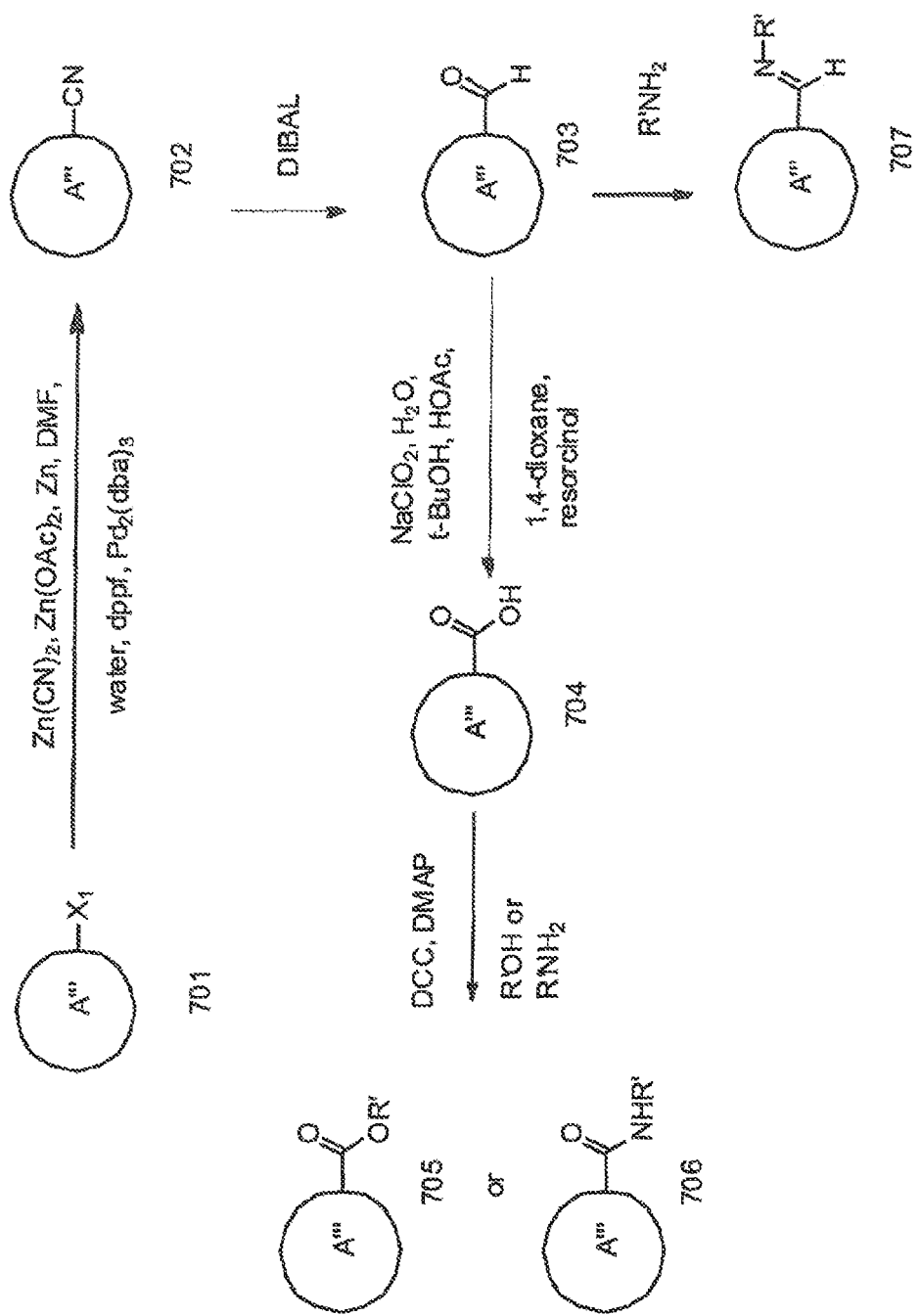
FIG. 8 is a representative synthetic scheme (Scheme 7) by which naphthopyran compounds according to the present invention can be prepared.

With reference to Scheme 7 of FIG. 8 there are depicted additional chemistries that can be performed on the naphthopyran compounds for purposes of attaching lengthening group L. Substituent A'" is an abbreviated representation of 202, 302 and 306. Scheme 7 complements what can be done from Scheme 1 to 6 for attaching L. The cyanation and oxidation methods are described in U.S. Patent Application Publication No. US 2009/0309076 A1, in which these cyanation and oxidation methods are incorporated herein by reference.

The present invention is more particularly described in the following examples, which are intended to be illustrative only, since numerous modifications and variations therein will be apparent to those skilled in the art. Unless otherwise specified, all parts and all percentages are by weight.

EXAMPLES

Part 1 describes the preparation of naphthopyran compounds in Examples 1-12. Part 2 describes the testing of the photochromic properties of the naphthopyran compounds of Examples 1-12. Part 3 describes the testing of the dichroic properties of the napthopyran compounds of Examples 1-12.
Part 1—Preparation of Examples 1-12

In the following examples, the synthetic procedures for preparing naphthopyran compounds according to the present invention are described.

Example 1

A naphthopyran compound according to Formula (II) of the present invention and as represented by the following Formula (E-1) was prepared in accordance with the following procedure.

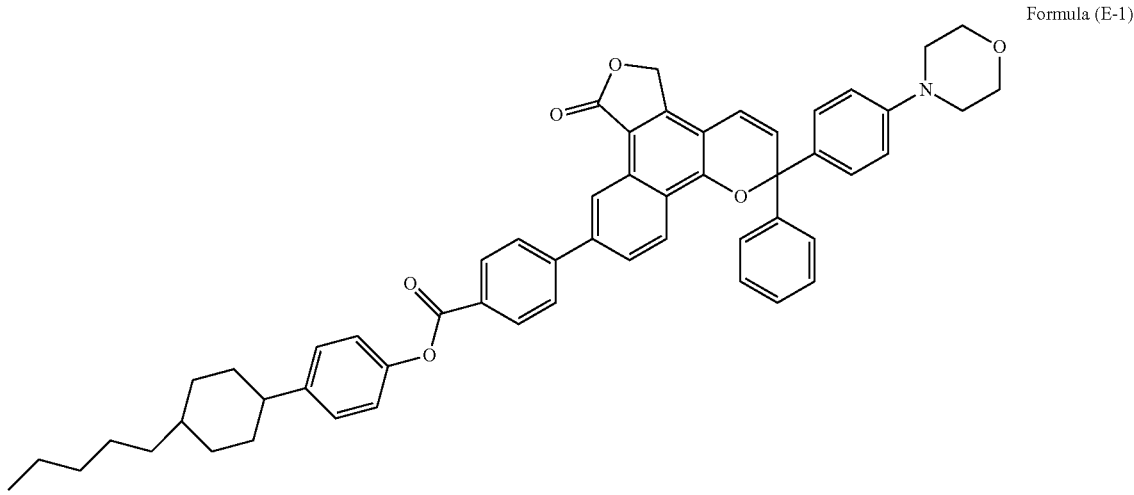 [SMILES: CCCCCC1CCC(c2ccc(OC(=O)c3ccc(-c4ccc5c6c(c7c(c5c4)C(=O)OC7)C=CC(c4ccccc4)(c4ccc(N5CCOCC5)cc4)O6)cc3)cc2)CC1]
Formula (E-1)

Step 1

A dichloromethane solution (0.5 L) of 4-bromoacetophenone (100.0 g) and triethylamine (210 mL) was cooled to 5-10° C. Triisopropylsilyl trifluoromethanesulfonate (162 mL) was added drop wise over a 30 min interval. After 1 h, the reaction mixture was diluted with dichloromethane (1 L) and poured into a saturated solution of sodium bicarbonate (1 L). The mixture was stirred for 10 min and partitioned. The dichloromethane solution was collected and dried with anhydrous sodium sulfate. The solvent was removed under vacuum and the residue was purified by filtration through a plug of basic alumina using 4:1 dichloromethane-hexane mixture as the eluent. Fractions containing the desired material were grouped and concentrated to provide a colorless oil (160 g). NMR analysis of the colorless oil indicated a structure that was consistent with ((1-(4-bromophenyl)vinyl)oxy) triisopropylsilane.

Step 2

To a flask containing the product from Step 1 (160 g) was added toluene (200 mL), maleic anhydride (50.0 g) and chloranil (145 g). The mixture was heated to reflux for 20 h. The reaction mixture was cooled to room temperature and filtered. The filtrate was collected and the solvent was removed under vacuum to provide a residue. The residue was purified by column chromatography using 4:1 hexane ethyl acetate mixture as the eluent. Fractions containing the desired material were grouped and concentrated to provide an orange colored solid (79 g). NMR analysis of the orange colored solid indicated a structure that was consistent with 8-bromo-5-((triisopropylsilyl)oxy)naphtho[1,2-c]furan-1,3-dione.

Step 3

To a tetrahydrofuran solution (10 mL) of the product from Step 2 (5 g) at 0° C. was added sodium borohydride (0.46 g). The reaction mixture was warmed to room temperature and stirred for 2 h. The reaction mixture was acidified to pH 4 with 10% aqueous hydrochloric acid. The solvent was removed under vacuum and the aqueous solution was extracted with ethyl acetate (3×100 mL). The combined ethyl acetate extracts were dried with anhydrous sodium sulfate and the solvent was removed under vacuum. The residue was purified by column chromatography using 9:1 hexane-ethyl acetate mixture as the eluent. Fractions containing the desired material were grouped and concentrated to provide a solid (1.7 g). NMR analysis of the solid indicated a structure that was consistent with 8-bromo-5-((triisopropylsilyl)oxy)naphtha[1,2-c]furan-1(3H)-one.

Step 4

The product from Step 3 (1.59 g) was dissolved in tetrahydrofuran (10 mL) and an aqueous solution of potassium fluoride (2.1 g in 10 mL of water) was added. The mixture was stirred at room temperature for 18 h. The mixture was diluted with ethyl acetate (100 mL) and partitioned. The ethyl acetate extract was dried with anhydrous sodium sulfate and concentrated in vacuo to provide a residue. The residue was precipitated from dichloromethane. The precipitate was collected by vacuum filtration and dried to provide a solid (0.82 g). NMR analysis of the solid indicated a structure that was consistent with 8-bromo-5-hydroxynaphtho[1,2-c]furan-1(3H)-one.

Step 5

To a chloroform solution (50 mL) of the product from Step 4 (0.82 g) were added 1-phenyl-1-(4-(N-morpholino)phenyl) prop-2-yn-1-ol (1.1 g), triisopropyl orthoformate (1 mL) and pyridine p-toluenesulfonate (0.07 g). The mixture was heated to reflux for 16 h. The reaction mixture was cooled to room temperature and the solvent was removed under vacuum. The residue was purified by column chromatography using 4:1 hexane ethyl acetate mixtures as the eluent. Fractions containing the desired material were grouped and concentrated to provide an oily residue (0.42 g). NMR analysis of the residue indicated a structure that was consistent with 9-bromo-2-(4-morpholinophenyl)-2-phenyl-2,5-dihydro-7-oxo-furo[3',4':3,4]naphtho[1,2-b]pyran.

Step 6

A mixture of the product from Step 5 (0.42 g), 4-(4-trans-pentylcyclohexyl)pheny-4-(4,4,5,5-tetramethyl-1,3,2-dioxaborolan-2-yl)benzoate (0.43 g), dichlorobis(triphenylphosphine)palladium (II) (0.03 g), potassium fluoride (0.71 g), THF (10 mL) and water (10 mL) was degassed for 10 min and heated to reflux for 16 h. The reaction mixture was cooled and diluted with ethyl acetate (100 mL). The mixture was filtered through CELITE® filtering aid and the filtrate was collected and concentrated in vacuo to provide a residue. The residue was purified by column chromatography using 4:1 hexane-ethyl acetate mixture as the eluent. Fractions containing the desired material were grouped and concentrated in vacuo to provide a solid (0.5 g). NMR of the solid indicated a structure that was consistent with 2-(4-morpholinophenyl)-2-phenyl-9-(4-(4-(4-pentylcyclohexyl)phenyloxycarbonyl)phenyl)-2,5-dihydro-7-oxo-furo[3',4':3,4]naphtho[1,2-b]pyran, as represented by Formula (E-1) above. The compound demonstrated a dichroic ratio of 5.7 according to the CELL METHOD.

Example 2

A naphthopyran compound according to Formula (II) of the present invention and as represented by the following Formula (E-2) was prepared in accordance with the following procedure.

Formula (E-2)

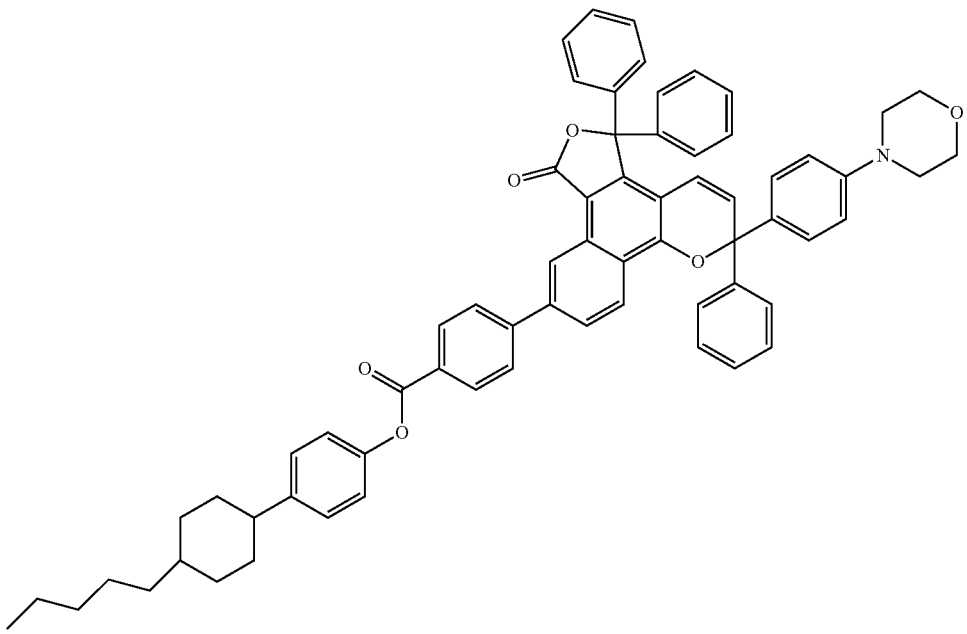

Step 1

The procedures of Steps 1 to 6 of Example 1 were followed except phenylmagnesium bromide was used instead of sodium borohydride in Step 3. NMR analysis showed that the structure was consistent with 2-(4-morpholinophenyl)-2,5,5-triphenyl-9-(4-(4-(4-pentylcyclohexyl)phenyloxycarbonyl)phenyl)-2,5-dihydro-7-oxo-furo[3',4':3,4]naphtho[1,2-b]pyran, as represented by Formula (E-2) above. The compound demonstrated a dichroic ratio of 6.1 according to the CELL METHOD.

Example 3

A naphthopyran compound according to Formula (II) of the present invention and as represented by the following Formula (E-3) was prepared in accordance with the following procedure.

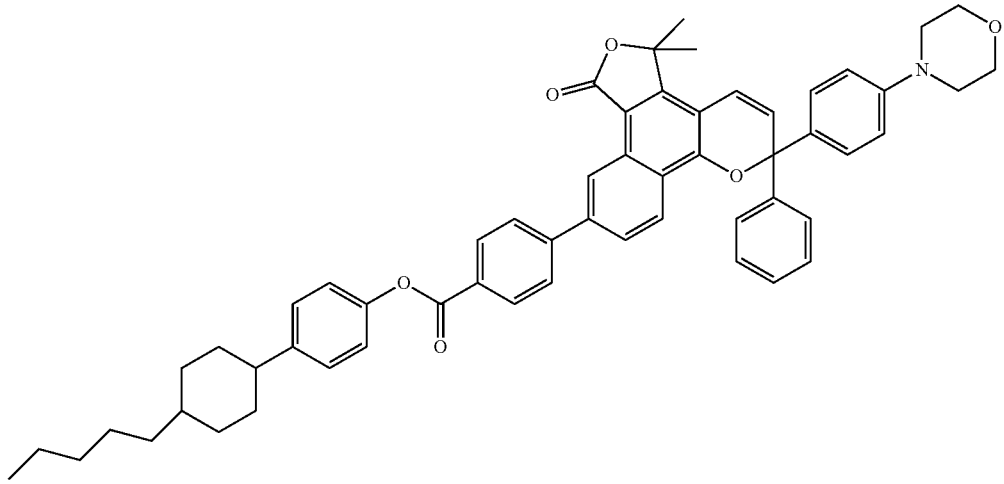

Formula (E-3)

Step 1

The procedures of Steps 1 to 6 of Example 1 were followed except methylmagnesium bromide was used instead of sodium borohydride in Step 3. NMR analysis showed that the structure was consistent with 5,5-dimethyl-2-(4-morpholinophenyl)-2-phenyl-9(4-(4-(4-pentylcyclohexyl)phenyloxycarbonyl)phenyl)-2,5-dihydro-7-oxo-furo[3',4':3,4]naphtho[1,2-b]pyran, as represented by Formula (E-3) above. The compound demonstrated a dichroic ratio of 5.7 according to the CELL METHOD.

Example 4

A naphthopyran compound according to Formula (II) of the present invention and as represented by the following Formula (E-4) was prepared in accordance with the following procedure.

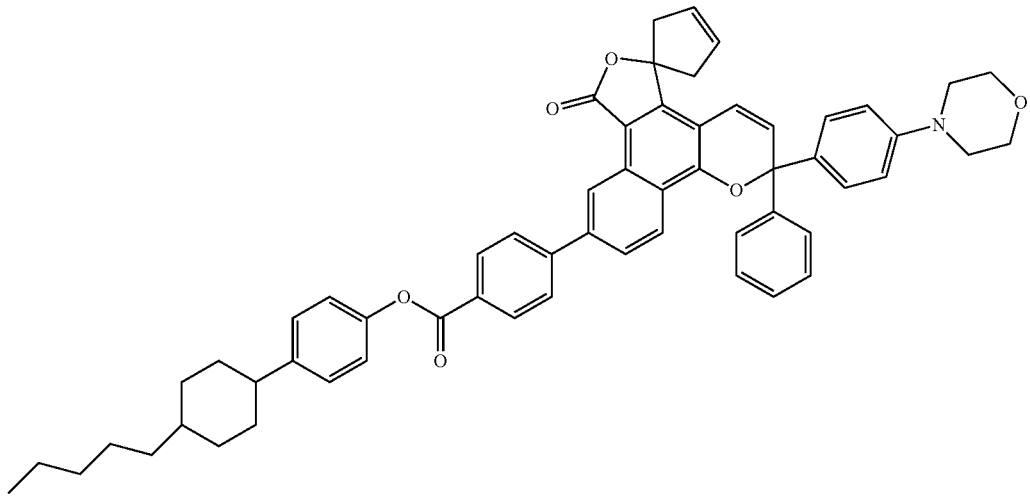

Formula (E-4)

Step 1

The procedures of Steps 1 to 3 of Example 1 were followed except that allylmagensium bromide was used instead of sodium borohydride as in Step 3. A mixture of compounds was obtained and this was used in the next step.

Step 2

The mixture of compounds from the previous step (1.96 g) was dissolved in toluene (40 ml) and degassed for 10 min. Grubbs II catalyst (1,3-bis(2,4,6-trimethylphenyl)-2-imidazolidinylidene)dichloro(phenylmethylene)tricyclhexylphosphine)ruthenium) (0.16 g) was added and the mixture heated at reflux for 4 h. The reaction mixture was cooled to room temperature. The solvent was removed under vacuum. The residue was purified by column chromatography using 9:1 hexane-ethyl acetate mixture as the eluent. Fractions containing the desired material were grouped and concentrated to provide a residue that was used in the next step.

Step 3

The residue from Step 2 of the present Example 4 was subjected to the procedure of Step 4 of Example 1. Two compounds were isolated in a ratio of 2:1. NMR analysis of the major compound indicated a structure that was consistent with 2-(4-morpholinophenyl)-2-phenyl-9-bromo-2,5-dihydro-7-oxo-spiro[cyclopent[3]ene-1',5-furo[3',4':3,4]naphtho[1,2-b]pyran. NMR analysis of the minor compound indicated a structure that was consistent with 2-(4-morpholinophenyl)-2-phenyl-9-bromo-2,5-dihydro-5-oxo-spiro[cyclopent[3]ene-1',7-furo[3',4':3,4]naphtho[1,2-b]pyran.

Step 4

The major compound from Step 3 of the present Example 4 was subjected to the procedures of Steps 5 and 6 of Example 1. NMR analysis showed that the structure was consistent with 2-(4-morpholinophenyl)-2-phenyl-9-(4-(4-(4-pentylcyclohexyl)phenyloxycarbonyl)phenyl)-2,5-dihydro-7-oxo-spiro[cyclopent[3]ene-1',5-furo[3',4':3,4]naphtho[1,2-b]pyran, as represented by Formula (E-4) above. The compound of the present Example 4 demonstrated a dichroic ratio of 6.2 according to the CELL METHOD.

Example 5

A naphthopyran compound according to Formula (I) of the present invention and as represented by the following Formula (E-5) was prepared in accordance with the following procedure.

Formula (E-5)

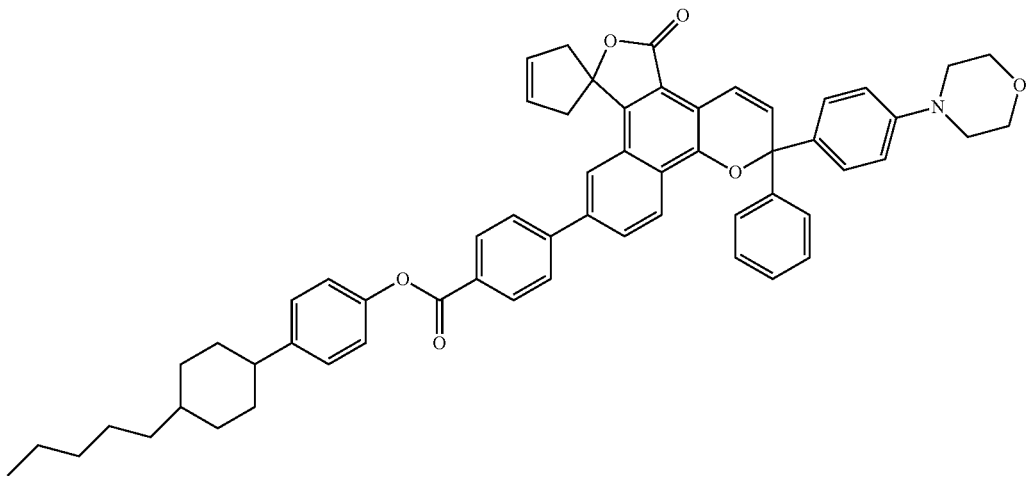

Step 1

The procedures of Steps 1 to 3 of Example 4 were followed. The minor compound from Step 3 of Example 4 was subjected to the procedures of Steps 5 and 6 of Example 1. NMR analysis showed that the structure was consistent with 2-(4-morpholinophenyl)-2-phenyl-9-(4-(4-(4-pentylcyclohexyl)phenyloxycarbonyl)phenyl)-2,5-dihydro-5-oxo-spiro[cyclopent(3]ene-1',7-furo[3',4':3,4]naphtho[1,2-b]pyran, as represented by Formula (E-5) above. The compound of the present Example 5 demonstrated a dichroic ratio of 6.9 according to the CELL METHOD.

Example 6

A naphthopyran compound according to Formula (II) of the present invention and as represented by the following Formula (E-6) was prepared in accordance with the following procedure.

Formula (E-6)

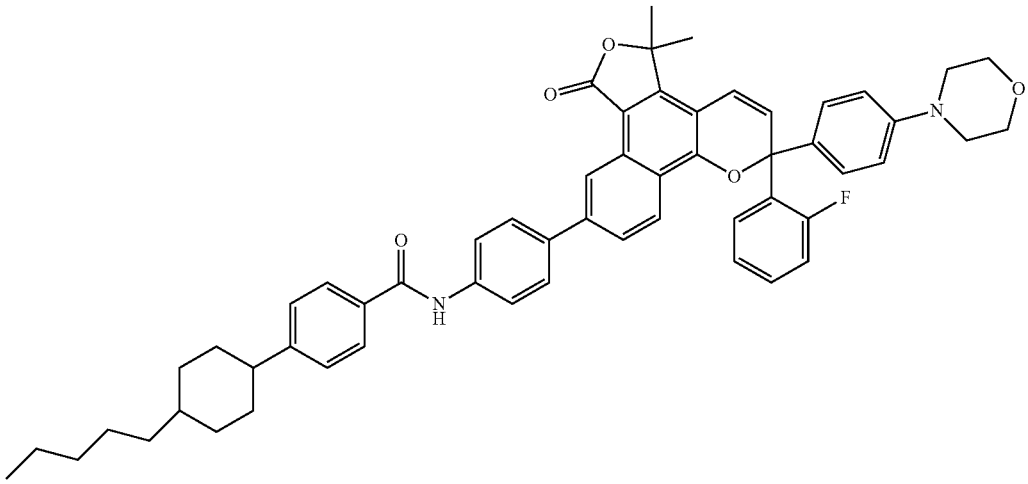

Step 1

The procedures of Steps 1 to 6 of Example 1 were followed except methylmagnesium bromide was used instead of sodium borohydride in Step 3, 1-(2-fluorophenyl-1-(4-(N-morpholino)phenyl)prop-2-yn-1-ol was used instead of 1-phenyl-1-(4-(N-morpholino)phenyl)prop-2-yn-1-ol in Step 5 and 4-(4-trans-pentylcyclohexyl)pheny-4-(4,4,5,5-tetramethyl-1,3,2-dioxaborolan-2-yl)benzamide was used instead of 4-(4-trans-pentylcyclohexyl)pheny-4-(4,4,5,5-tetramethyl-1,3,2-dioxaborolan-2-yl)benzoate in Step 6. NMR analysis showed that the structure was consistent with 5,5-dimethyl-2-(2-fluorophenyl)-2-(4-morpholinophenyl)- 9-(4-(4-(4-pentylcyclohexyl)phenyloxycarbonyl)phenyl)-2,5-dihydro-7-oxo-furo[3',4':3,4]naphtho[1,2-b]pyran, as represented by Formula (E-6) above. The compound demonstrated a dichroic ratio of 5.8 according to the CELL METHOD.

Example 7

A naphthopyran compound according to Formula (II) of the present invention and as represented by the following Formula (E-7) was prepared in accordance with the following procedure.

Formula (E-7)

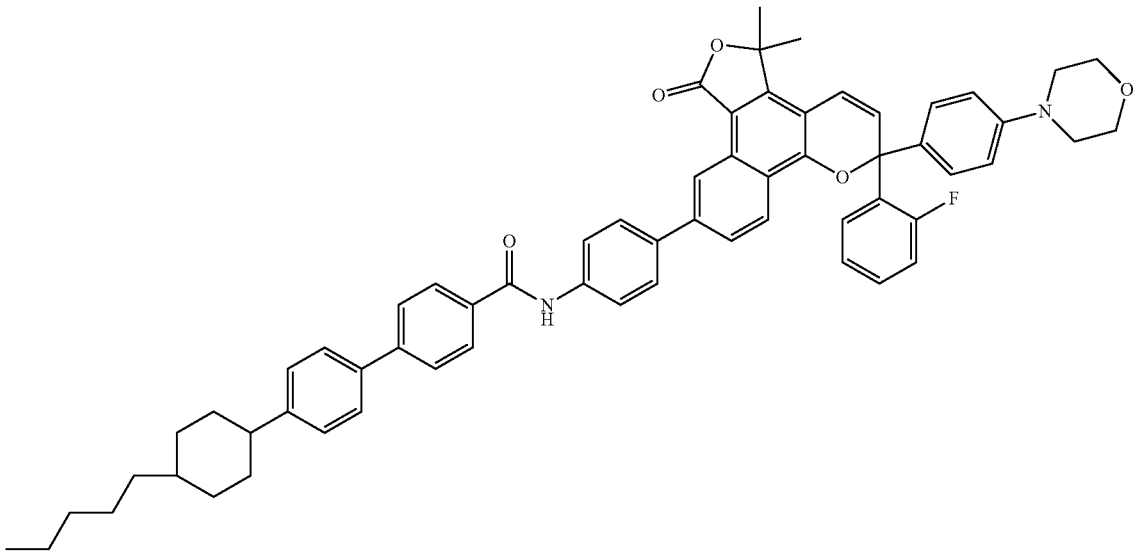

Step 1

The procedures of Steps 1 to 6 of Example 1 were followed except methylmagnesium bromide was used instead of sodium borohydride in Step 3, 1-(2-fluorophenyl)-1-(4-(N-morpholino)phenyl)prop-2-yn-1-ol was used instead of 1-phenyl-1-(4-(N-morpholino)phenyl)prop-2-yn-1-ol in Step 5 and 4'-(4-trans-pentylcyclohexyl)-N-(4-(4,4,5,5-tetramethyl-1,3,2-dioxaborolan-2-yl)phenyl)-[1,1'-biphenyl]-4-carboxamide was used instead of 4-(4-trans-pentylcyclohexyl)pheny-4-(4,4,5,5-tetramethyl-1,3,2-dioxaborolan-2-yl)benzoate in Step 6. NMR analysis showed that the structure was consistent with 5,5-dimethyl-2-(2-fluorophenyl)-2-(4-morpholinophenyl)-9-(4-(4'-(4-pentylcyclohexyl)-[1,1'-biphenyl]-4-ylcarboxamido)phenyl)-2,5-dihydro-7-oxo-furo[3',4':3,4]naphtho[1,2-b]pyran, as represented by Formula (E-7) above. The compound demonstrated a dichroic ratio of 6.2 according to the CELL METHOD.

Example 8

A naphthopyran compound according to Formula (III) of the present invention and as represented by the following Formula (E-8) was prepared in accordance with the following procedure.

Step 2

A 1M solution of diisobutylaluminium hydride in hexane (20 mL) was added drop wise to the product from Step 1 of Example 8 (0.52 g) in THF (10 mL). The reaction mixture was stirred at room temperature for 1 h. The reaction mixture was quenched with 10% aqueous hydrochloric acid. The solvent was removed under vacuum and the aqueous solution was extracted with ethyl acetate (3×100 mL). The combined ethyl acetate extracts were dried with anhydrous sodium sulfate and the solvent was removed under vacuum. The residue was purified by column chromatography using 9:1 hexane-ethyl acetate mixture as the eluent. Fractions containing the desired material were grouped and concentrated to provide a solid (0.26 g). NMR analysis of the solid indicated a structure that was consistent with 8-bromo-3,3-dimethyl-1,3-dihydronaphtho[1,2-c]furan-5-ol.

Step 3

The procedures of Steps 5 and 6 of Example 1 were followed. NMR analysis showed that the structure is consistent with 5,5-dimethyl-2-(4-morpholinophenyl)-2-phenyl-9-(4-(4-(4-pentylcyclohexyl)phenyloxycarbonyl)phenyl)-2,5,7-trihydro-furo[3',4':3,4]naphtho[1,2-b]pyran, as represented by Formula (E-8) above. The compound demonstrated a dichroic ratio of 5.8 according to the CELL METHOD.

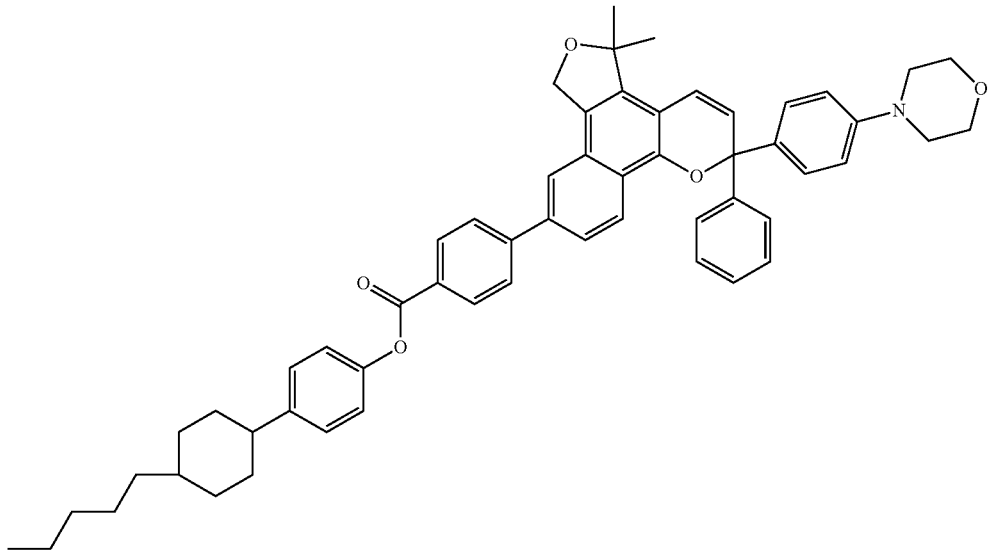

Formula (E-8)

Step 1

The procedures of Steps 1 to 4 of Example 1 were followed except methylmagnesium bromide was used instead of sodium borohydride in Step 3. NMR analysis showed that the structure was consistent with 8-bromo-5-hydroxy-3,3-dimethylnaphtho[1,2-c]furan-1 (3H)-one.

Example 9

A naphthopyran compound according to Formula (III) of the present invention and as represented by the following Formula (E-9) was prepared in accordance with the following procedure.

Formula (E-9)

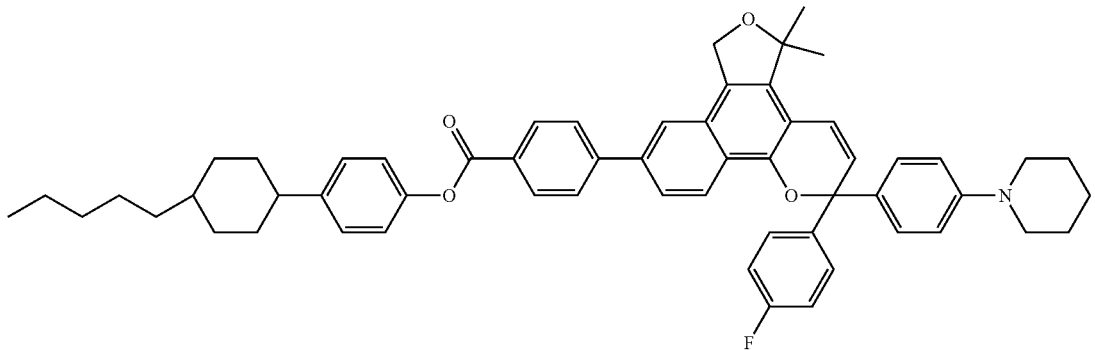

Step 1

The procedures of Steps 1 and 2 of Example 8 were followed to provide 8-bromo-3,3-dimethyl-1,3-dihydronaphtho[1,2-c]furan-5-ol.

Step 2

The procedures of Steps 5 and 6 of Example 1 were followed except that 1-(4-fluorophenyl)-1-(4-(N-piperidine)phenyl)prop-2-yn-1-ol was used instead of 1-phenyl-1-(4-(N-morpholino)phenyl)prop-2-yn-1-ol in Step 5. NMR analysis showed that the structure was consistent with 5,5-dimethyl-2-(4-fluorophenyl)-2-(4-morpholinophenyl)-9-(4-(4-(4-pentylcyclohexyl)phenyloxycarbonyl)phenyl)-2,5,7-trihydro-furo[3',4':3,4]naphtho[1,2-b]pyran, as represented by Formula (E-9) above. The compound demonstrated a dichroic ratio of 7.7 according to the CELL METHOD.

Example 10

A naphthopyran compound according to Formula (III) of the present invention and as represented by the following Formula (E-10) was prepared in accordance with the following procedure.

Formula (E-10)

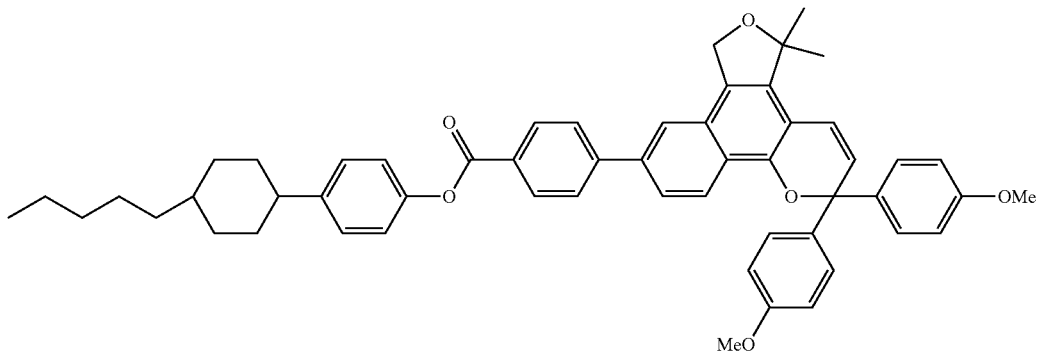

Step 1

The procedures of Steps 1 and 2 of Example 8 were followed to provide 8-bromo-3,3-dimethyl-1,3-dihydronaphtho[1,2-c]furan-5-ol.

Step 2

The procedures of Steps 5 and 6 of Example 1 were followed except that 1,1-bis(4-methoxyphenyl)prop-2-yn-1-ol was used instead of 1-phenyl-1-(4-(N-morpholino)phenyl)prop-2-yn-1-ol in Step 5. NMR analysis showed that the structure was consistent with 5,5-dimethyl-2,2-di-(methoxyphenyl)-9-(4-(4-(4-pentylcyclohexyl)phenyloxycarbonyl)phenyl)-2,5,7-trihydro-furo[3,4':3,4]naphtho[1,2-b]pyran, as represented by Formula (E-10) above. The compound demonstrated a dichroic ratio of 8.9 according to the CELL METHOD.

Example 11

A naphthopyran compound according to Formula (III) of the present invention and as represented by the following Formula (E-11) was prepared in accordance with the following procedure.

Formula (E-11)

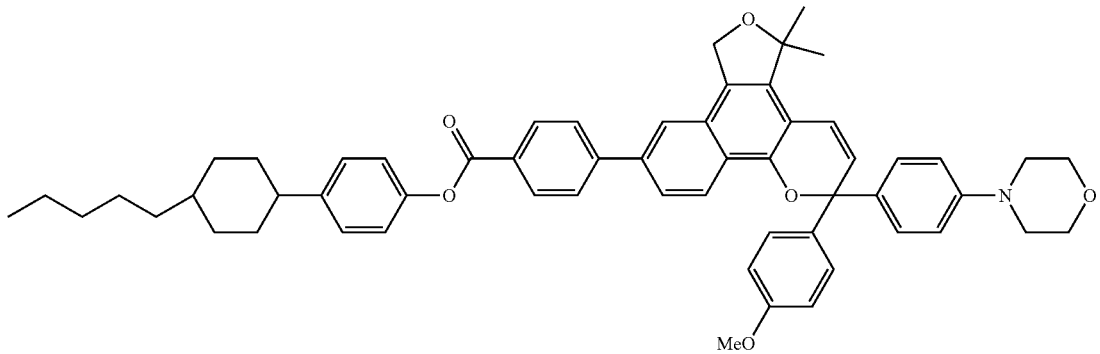

Step 1

The procedures of Steps 1 and 2 of Example 8 were followed to provide 8-bromo-3,3-dimethyl-1,3-dihydronaphtho[1,2-c]furan-5-ol.

Step 2

The procedures of Steps 5 and 6 of Example 1 were followed except that 1-(4-methoxyphenyl)-1-(4-(N-morpholino)phenyl)prop-2-yn-1-ol was used instead of 1-phenyl-1-(4-(N-morpholino)phenyl)prop-2-yn-1-ol in Step 5. NMR analysis showed that the structure was consistent with 5,5-dimethyl-2-(methoxyphenyl)-2-(4-morpholinophenyl)-9-(4-(4-(4-pentylcyclohexyl)phenyloxycarbonyl)phenyl)-2,5,7-trihydro-furo[3',4':3,4]naphtho[1,2-b]pyran, as represented by Formula (E-11) above. The compound demonstrated a dichroic ratio of 7.7 according to the CELL METHOD.

Example 12

A naphthopyran compound according to Formula (III) of the present invention and as represented by the following Formula (E-12) was prepared in accordance with the following procedure.

borohydride in Step 3. NMR analysis showed that the structure was consistent with 8-bromo-5-hydroxy-3,3-diethyl-naphtho[1,2-c]furan-1(3H)-one.

Step 2

The procedure of Step 2 of Example 8 was followed. NMR analysis showed that the structure was consistent with 8-bromo-3,3-diethyl-1,3-dihydronaphtho[1,2-c]furan-5-ol.

Step 3

The procedure of Steps 5 and 6 of Example 1 were followed. NMR analysis showed that the structure was consistent with 5,5-diethyl-2-(4-morpholinophenyl)-2-phenyl-9-(4-(4-(4-pentylcyclohexyl)phenyloxycarbonyl)phenyl)-2,5,7-trihydro-furo[3',4':3,4]naphtho[1,2-b]pyran, as represented by Formula (E-12) above. The compound demonstrated a dichroic ratio of 7.2 according to the CELL METHOD.

Part 2—Photochromic Property Testing

Part 2A—Test Square Preparation

Testing was done with the compounds described in Examples 1-12 in the following manner. A quantity of compound calculated to yield a $1.5 \times 10^{-3}$ molal solution was added to a flask containing 50 grams of a monomer blend of 4 parts ethoxylated bisphenol A dimethacrylate (BPA 2EO Formula (E-12)

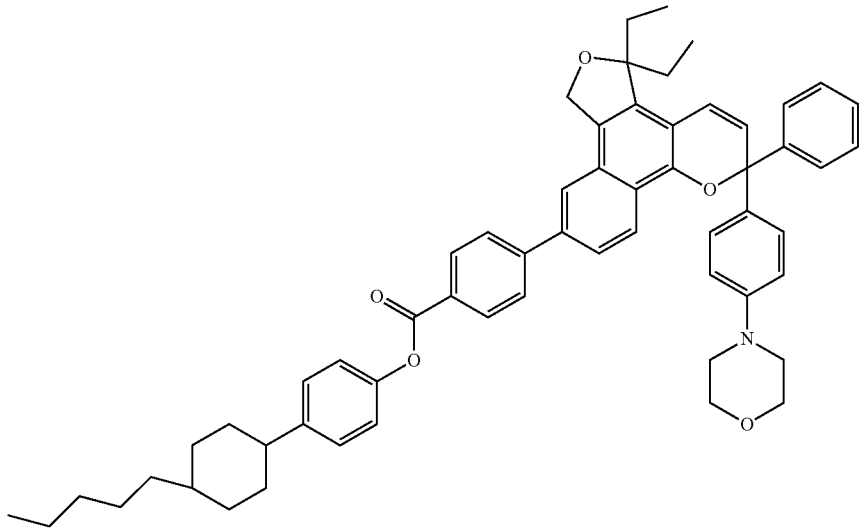

Step 1

The procedures of Steps 1 to 4 of Example 1 were followed except ethylmagnesium bromide was used instead of sodium DMA), 1 part poly(ethylene glycol) 600 dimethacrylate, and 0.033 weight percent 2,2'-azobis(2-methyl propionitrile) (AIBN). Each compound was dissolved into the monomer blend by stirring and gentle heating, if necessary. After a clear solution was obtained, the sample was degassed in a vacuum oven for 5-10 minutes at 25 torr. Using a syringe, the sample was poured into a flat sheet mold having an interior dimension of 2.2 mm+/−0.3 mm×6 inch (15.24 cm)×6 inch (15.24 cm). The mold was sealed and placed in a horizontal airflow, programmable oven to ramp from 40° C. to 95° C. over a 5 hour interval, hold the temperature at 95° C. for 3 hours, ramp down to 60° C. over a 2 hour interval and then hold at 60° C. for 16 hours. After curing, the mold was opened, and the polymer sheet was cut into 2 inch (5.1 cm) test squares using a diamond blade saw.

Part 2B—Response Testing

Prior to response testing on an optical bench, the test squares from Part 2A were conditioned by exposing them to 365 nm ultraviolet light for 10 minutes at a distance of about 14 cm from the source in order to pre-activate the photochromic compounds in samples. The UVA irradiance at the sample surface was measured with a Licor Model Li-1800 spectroradiometer and found to be 22.2 Watts per square meter. The samples were then placed under a halogen lamp (500 W, 120V) for about 10 minutes at a distance of about 36 cm from the lamp in order to bleach, or inactivate, the photochromic compounds in the samples. The illuminance at the sample was measured with the Licor spectroradiometer and found to be 21.9 Klux. The samples were then kept in a dark environment for at least 1 hour prior to testing in order to cool and continue to fade back to a ground state.

The optical bench was fitted with an Newport Model #67005 300-watt Xenon arc lamp, and Model 69911 power supply, Vincent Associates (model VS25S2ZM0R3 with VMM-D4 controller) high-speed computer controlled shutter, a Schott 3 mm KG-2 band-pass filter, which removed short wavelength radiation, neutral density filter(s) to attenuate light from the xenon lamp, a fused silica condensing lens for beam collimation, and a fused silica water cell/sample holder for maintaining sample temperature in which the test sample to be tested was inserted. The temperature in the water cell was controlled with a pumped water circulation system in which the water passed through copper coils that were placed in the reservoir of a chiller unit. The water cell used to hold test samples contained fused silica sheets on the front and back facings in order to eliminate spectral change of the activation or monitoring light beams. The filtered water passing through the water cell was maintained at 72° F.±2° for photochromic response testing. A Newport Model 689456 Digital Exposure Timer was used to control the intensity of the xenon arc lamp during activation of the sample.

A broadband light source for monitoring response measurements was positioned in a perpendicular manner to a surface of the cell assembly. Increased signal of shorter visible wavelengths was obtained by collecting and combining separately filtered light from a 100-Watt tungsten halogen lamp (controlled by a Lambda UP60-14 constant voltage power supply) with a split-end, bifurcated fiber optical cable. Light from one side of the tungsten halogen lamp was filtered with a Schott KG1 filter to absorb heat and a Hoya B-440 filter to allow passage of the shorter wavelengths. The other side of the light was either filtered with a Schott KG1 filter or unfiltered. The light was collected by focusing light from each side of the lamp onto a separate end of the split-end, bifurcated fiber optic cable, and subsequently combined into one light source emerging from the single end of the cable. A 4" light pipe was attached to the single end of the cable to insure proper mixing. After passing through the sample, the light was refocused into a 2-inch integrating sphere and fed to an Ocean Optics S2000 spectrophotometer by fiber optic cables. Ocean Optics SpectraSuite and PPG proprietary software were used to measure response and control the operation of the optical bench.

Irradiance for response testing of the samples on the optical bench was established at the sample surface using an International Light Research Radiometer, Model IL-1700 with a detector system comprising a Model SED033 detector, B Filter and diffuser. The output display of the radiometer was corrected (factor values set) against a Licor 1800-02 Optical Calibration Calibrator in order to display values representing Watts per square meter UVA. The irradiance at the sample point for initial response testing was set at to 3.0 Watts per square meter UVA and approximately 8.6 Klux illuminance. During sample response testing, if a sample darkened beyond an acceptable detection capability limit, the irradiance was lowered to 1.0 Watts per square meter UVA or the sample was remade at a one-half concentration in the copolymer. Adjusting the output of the filtered xenon arc lamp was accomplished by increasing or decreasing the current to the lamp through the controller and/or by adding or removing neutral density filters in the light path. The test samples were exposed to the activation light at 31 normal to its surface while being perpendicular to the monitoring light.

Samples were activated in the 73° F.(22.8° C.) controlled water cell for 30 minutes, then allowed to fade under room light conditions until the change in optical density of the activated sample faded to ¼ of its highest dark (saturated) state or for a maximum of 30 minutes of fade.

Change in optical density ($\Delta OD$) from the bleached state to the darkened state was determined by establishing the initial transmittance, opening the shutter from the Xenon lamp to provide ultraviolet radiation to change the test lens from the bleached state to an activated (i.e., darkened) state. Data was collected at selected intervals of time, measuring the transmittance in the activated state, and calculating the change in optical density according to the formula: $\Delta OD = \log(\% Tb/\% Ta)$, where % Tb is the percent transmittance in the bleached state, % Ta is the percent transmittance in the activated state and the logarithm is to the base 10.

The $\lambda_{max\text{-}vis}$ in the visible light range is the wavelength in the visible spectrum at which the maximum absorption of the activated form of the photochromic compound occurs. The $\lambda_{max\text{-}vis}$ was determined by testing the photochromic test square in a Varian Cary 4000 UV-Visible spectrophotometer or comparable equipment.

The $\Delta OD/Min$, which represents the sensitivity of the photochromic compound's response to UV light, was measured over the first five (5) seconds of UV exposure, then expressed on a per minute basis. The saturation optical density ($\Delta OD$ at saturation) was taken under identical conditions except UV exposure was continued for a total of 30 minutes. The fade half life is the time interval in seconds for the $\Delta OD$ of the activated form of the photochromic compound in the test squares to reach one half the $\Delta OD$ measured after thirty minutes, or after saturation or near-saturation was achieved, at room temperature after removal of the source of activating light, e.g., by closing the shutter. Results are listed in Table I.

TABLE 1

Photochromic Performance Test Results

| Example # | $\lambda_{max\text{-}vis}$ (nm) | Sensitivity ($\Delta OD/Min$) | $\Delta OD$ at saturation | T ½ (sec) |
|---|---|---|---|---|
| 1 | 604 | 0.14 | 0.14 | 405 |
| 2 | 631 | 0.13 | 0.11 | 46 |
| 3 | 614 | 0.17 | 0.09 | 27 |
| 4 | 616 | 0.28 | 0.20 | 35 |
| 5 | 574 | 0.49 | 0.41 | 54 |
| 6 | 609 | 0.52 | 0.99 | 144 |
| 7 | 611 | 0.67 | 1.07 | 121 |
| 8 | 550 | 0.59 | 1.32 | 298 |
| 9 | 573 | 0.62 | 1.03 | 167 |
| 10 | 525 | 0.69 | 1.01 | 173 |
| 11 | 558 | 0.57 | 0.86 | 149 |
| 12 | 553 | 0.74 | 1.41 | 250 |

Part 3—Dichroic Property Testing
Part 3A—Liquid Crystal Cell Preparation

The average dichroic ratio of each of the compounds of Examples 1-12 was determined according to the CELL METHOD described as follows.

A cell assembly having the following configuration was obtained from Design Concepts, Inc. Each of the cell assemblies was formed from two opposing glass substrates that are spaced apart with a glass bead spacer having a diameter of 20 microns+/−1 micron. The inner surfaces of each of the glass substrates had oriented polyimide coating thereon to provide for the alignment of a liquid crystal material as discussed below. Two opposing edges of the glass substrates were sealed with an epoxy sealant, leaving the remaining two edges open for filling.

The gap between the two glass substrates of the cell assembly was filled with a liquid crystal solution containing the one of the compounds of Examples 1-12. The liquid crystal solution was formed by mixing the following components in the weight percents listed below with heating, if necessary, to dissolve the test material.

| Material | Weight Percent |
|---|---|
| Licristal ™ E7 | 97-99.5 |
| Example Compound | 0.5-3 |

Part 3B—Liquid Crystal Cell Testing

An optical bench was used to measure the optical properties of the cell and derive the absorption ratios for each of the Test Materials. The filled cell assembly was placed on the optical bench with an activating light source (an Oriel Model 66011 300-Watt Xenon arc lamp fitted with a Vincent Associates (model VS25S2ZM0R3 with VMM-D4 controller) high-speed computer controlled shutter that momentarily closed during data collection so that stray light would not interfere with the data collection process, a Schott 3 mm KG-1 band-pass filter, which removed short wavelength radiation, neutral density filter(s) for intensity attenuation and a condensing lens for beam collimation) positioned at a 30° to 35° angle of incidence a surface of the cell assembly.

A broadband light source for monitoring response measurements was positioned in a perpendicular manner to a surface of the cell assembly. Increased signal of shorter visible wavelengths was obtained by collecting and combining separately filtered light from a 100-Watt tungsten halogen lamp (controlled by a Lambda UP60-14 constant voltage powder supply) with a split-end, bifurcated fiber optical cable. Light from one side of the tungsten halogen lamp was filtered with a Schott KG1 filter to absorb heat and a Hoya B-440 filter to allow passage of the shorter wavelengths. The other side of the light was either filtered with a Schott KG1 filter or unfiltered. The light was collected by focusing light from each side of the lamp onto a separate end of the split-end, bifurcated fiber optic cable, and subsequently combined into one light source emerging from the single end of the cable. A 4" light pipe was attached to the single end of the cable to insure proper mixing.

Polarization of the light source was achieved by passing the light from the single end of the cable through a Moxtek, Proflux Polarizer held in a computer driven, motorized rotation stage (Model M-061-PD from Polytech, PI). The monitoring beam was set so that the one polarization plane (0°) was perpendicular to the plane of the optical bench table and the second polarization plane (90°) was parallel to the plane of the optical bench table. The samples were run in air, at room temperature (73° F.±0.3° F. or better (22.8° C.±0.1°)) maintained by the lab air conditioning system or a temperature controlled air cell.

To conduct the measurements, the cell assembly and the coating stack were exposed to 6.7 W/m² of UVA from the activating light source for 5 to 15 minutes to activate the Test Material. This was done for all of the Examples except Example 33, when tested in the coating stack, it was exposed to 2.0 W/m² of UVA. The lower exposure level was needed to obtain measurable results. An International Light Research Radiometer (Model IL-1700) with a detector system (Model SED033 detector, B Filter, and diffuser) was used to verify exposure prior to each test. Light from the monitoring source that was polarized to the 0° polarization plane was then passed through the coated sample and focused on a 1" integrating sphere, which was connected to an Ocean Optics S2000 spectrophotometer using a single function fiber optic cable. The spectral information, after passing through the sample, was collected using Ocean Optics SpectraSuite and PPG propriety software. While the photochromic-dichroic material was activated, the position of the polarizer was rotated back and forth to polarize the light from the monitoring light source to the 90° polarization plane and back. Data was collected for approximately 10 to 300 seconds at 5-second intervals during activation. For each test, rotation of the polarizers was adjusted to collect data in the following sequence of polarization planes: 0°, 90°, 90°, 0°, etc.

Absorption spectra were obtained and analyzed for each cell assembly using the Igor Pro software (available from WaveMetrics). The change in the absorbance in each polarization direction for each cell assembly was calculated by subtracting out the 0 time (i.e., unactivated) absorption measurement for the cell assembly at each wavelength tested. Average absorbance values were obtained in the region of the activation profile where the response of the Examples 1-12 was saturated or nearly saturated (i.e., the regions where the measured absorbance did not increase or did not increase significantly over time) for each cell assembly by averaging absorbance at each time interval in this region. The average absorbance values in a predetermined range of wavelengths corresponding $\lambda_{max-vis}$+/−5 nm were extracted for the 0° and 90° polarizations, and the absorption ratio for each wavelength in this range was calculated by dividing the larger average absorbance by the small average absorbance. For each wavelength extracted, 5 to 100 data points were averaged. The average absorption ratio for the Test Material was then calculated by averaging these individual absorption ratios.

For the Examples listed in Table 2 the above-described procedure was run at least twice. The tabled value for the Average Absorption Ratio represents an average of the results obtained from the runs measured at the wavelength indicated. The results of these tests are present in Table 2 below.

TABLE 2

Absorption Ratio (AR) Test Data

| Example # | Wavelength (nm) | Absorption Ratio |
|---|---|---|
| 1 | 611 | 5.7 |
| 2 | 630 | 6.1 |
| 3 | 618 | 6.2 |
| 4 | 617 | 6.2 |
| 5 | 576 | 6.9 |
| 6 | 610 | 5.8 |
| 7 | 610 | 6.2 |
| 8 | 554 | 5.8 |
| 9 | 576 | 7.7 |
| 10 | 527 | 8.9 |
| 11 | 560 | 7.7 |
| 12 | 554 | 7.2 |

The present invention has been described with reference to specific details of particular embodiments thereof. It is not intended that such details be regarded as limitations upon the scope of the invention except insofar as to the extent that they are included in the accompanying claims.

What is claimed is:

1. A naphthopyran compound selected from the group consisting of Formula (I), Formula (II), and Formula (III),

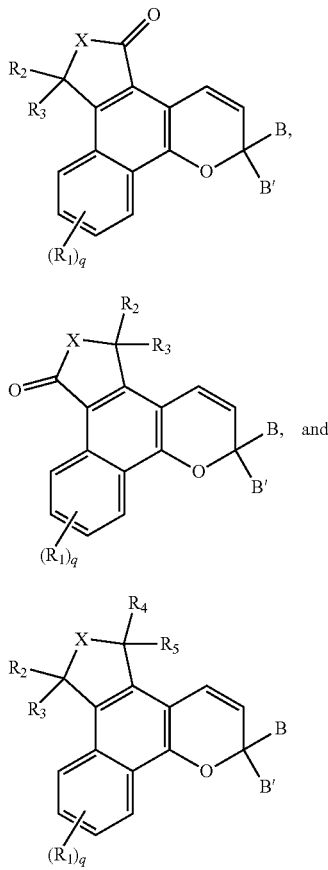

wherein each X is independently selected from —O—, —S—, and —N($R_6$)— where $R_6$ is selected from hydrogen, hydrocarbyl, and substituted hydrocarbyl, each q is independently from 1 to 4;

$R_1$ for each q is independently selected from: hydrogen, hydrocarbyl, and substituted hydrocarbyl each optionally and independently interrupted with at least one of —O—, —S—, —C(O)—, —C(O)O—, —S(O)—, —S($O_2$)—, —N=N—, —N($R_7$)— where $R_7$ is selected from hydrogen, hydrocarbyl or substituted hydrocarbyl, —Si(O$R_8$)$_w$($R_8$)$_t$—, where w and t are each independently selected from 0 to 2, provided that the sum of w and t is 2, and each $R_7$ is independently selected from hydrogen, hydrocarbyl and substituted hydrocarbyl, and combinations of two or more thereof; halogen; cyano; —N($R_9$)$R_{10}$, wherein $R_9$ and $R_{10}$ are each independently selected from hydrogen, hydrocarbyl or substituted hydrocarbyl, or $R_9$ and $R_{10}$ together form a ring structure optionally including at least one heteroatom; and a group L defined below;

$R_2$, $R_3$, $R_4$, and $R_5$ are each independently selected from hydrogen, hydrocarbyl and substituted hydrocarbyl each optionally and independently interrupted with at least one of —O—, —S—, —N($R_7$)— where $R_7$ is selected from hydrogen, hydrocarbyl or substituted hydrocarbyl, —Si(O$R_8$)$_w$($R_8$)$_t$—, where w and t are each independently selected from 0 to 2, provided that the sum of w and t is 2, and each $R_8$ is independently selected from hydrogen, hydrocarbyl and substituted hydrocarbyl, and combinations of two or more thereof; halogen; —N($R_9$)$R_{10}$, wherein $R_9$ and $R_{10}$ are each independently selected from hydrogen, hydrocarbyl or substituted hydrocarbyl, or $R_9$ and $R_{10}$ together form a ring structure optionally including at least one heteroatom, or R2 and $R_3$ together form a ring structure optionally including at least one heteroatom, or $R_4$ and $R_5$ together form a ring structure optionally including at least one heteroatom;

B and B' are each independently selected from, hydrogen, unsubstituted aryl, substituted aryl, unsubstituted heteroaryl, and substituted heteroaryl, or B and B' taken together form a ring structure selected from unsubstituted fluoren-9-ylidene, substituted fluoren-9-ylidene, saturated spiro-monocyclic hydrocarbon ring, saturated spiro-bicyclic hydrocarbon ring, and spiro-tricyclic hydrocarbon ring;

provided that at least one of (i) at least one $R_1$ is said group L, and (ii) at least one of B and B' is substituted with at least one group L, wherein each group L is independently represented by the following Formula (IV),

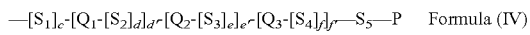

wherein:

(a) $Q_1$, $Q_2$, and $Q_3$ for each occurrence, are independently selected from a divalent group selected from optionally substituted aryl, optionally substituted heteroaryl, optionally substituted cycloalkyl, and optionally substituted heterocycloalkyl;

wherein the aryl substituents, heteroaryl substituents, cycloalkyl substituents, and heterocycloalkyl substituents are each independently selected from P, liquid crystal mesogens, halogen, poly($C_1$-$C_{18}$ alkoxy), $C_1$-$C_{18}$ alkoxycarbonyl, $C_1$-$C_{18}$ alkylcarbonyl, $C_1$-$C_{18}$ alkoxycarbonyloxy, aryloxycarbonyloxy, perfluoro($C_1$-$C_{18}$) alkoxy, perfluoro($C_1$-$C_{18}$)alkoxycarbonyl, perfluoro($C_1$-$C_{18}$)alkylcarbonyl, perfluoro($C_1$-$C_{18}$)alkylamino, di-(perfluoro($C_1$-$C_{18}$)alkyl)amino, perfluoro($C_1$-$C_{18}$) alkylthio, $C_1$-$C_{18}$ alkylthio, $C_1$-$C_{18}$ acetyl, $C_3$-$C_{10}$ cycloalkyl, $C_3$-$C_{10}$ cycloalkoxy, straight-chain $C_1$-$C_{18}$ alkyl, and branched $C_1$-$C_{18}$ alkyl;

wherein said straight-chain $C_1$-$C_{18}$ alkyl and branched $C_1$-$C_{18}$ alkyl are mono-substituted with a group selected from cyano, halogen, and $C_1$-$C_{18}$ alkoxy; or wherein said straight-chain $C_1$-$C_{18}$ alkyl and branched $C_1$-$C_{18}$ alkyl are poly-substituted with at least two groups independently selected from halogen, -M(T)$_{(v-1)}$ and -M(OT)$_{(v-1)}$, wherein M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and v is the valence of M;

(b) c, d, e, and f are each independently chosen from an integer from 1 to 20; and each $S_1$, $S_2$, $S_3$, $S_4$, and $S_5$ is independently chosen for each occurrence from a spacer unit selected from:

(i) optionally substituted alkylene, optionally substituted haloalkylene, —Si($CH_2$)$_g$—, and —(Si[($CH_3$)$_2$]O)$_h$—, wherein g for each occurrence is independently chosen from an integer from 1 to 20; h for each occurrence is independently chosen from an integer from 1 to 16; and said substitutes for the alkylene and haloalkylene are independently selected from $C_1$-$C_{18}$ alkyl, $C_3$-$C_{10}$ cycloalkyl and aryl;

(ii) —N(Z)—, —C(Z)=C(Z)—, —C(Z)=N—, —C(Z')$_2$—C(Z')$_2$—, and a single bond, wherein Z for each occurrence is independently selected from hydrogen, $C_1$-$C_{18}$ alkyl, $C_3$-$C_{10}$ cycloalkyl and aryl, and Z' for each occurrence is independently selected from $C_1$-$C_{18}$ alkyl, $C_3$-$C_{10}$ cycloalkyl and aryl; and (iii) —O—, —C(=O)—, —N=N—, —S—, —S(=O)—, —(O=)S(=O)—, —(O=)S(=O)O—, —O(O=)S(=O)O— and straight-chain or branched $C_1$-$C_{24}$ alkylene residue, said $C_1$-$C_{24}$ alkylene residue being unsubstituted, mono-substituted by cyano or halogen, or poly-substituted by halogen, provided that when two spacer units comprising heteroatoms are linked together the spacer units are linked so that heteroatoms are not directly linked to each other, each bond between Si and the naphthopyran compound represented by Formula (I), Formula (II), and Formula (III) is in each case free of two heteroatoms linked together, and the bond between $S_5$ and P is free of two heteroatoms linked to each other, and provided that S2 is other than —N(H)— and —O—;
(c) P for each occurrence is independently selected from hydroxy, amino, $C_2$-$C_{18}$ alkenyl, $C_2$-$C_{18}$ alkynyl, azido, silyl, siloxy, silylhydride, (tetrahydro-2H-pyran-2-yl)oxy, thio, isocyanato, thioisocyanato, acryloyloxy, methacryloyloxy, 2-(acryloyloxy)ethylcarbamyl, 2-(methacryloyloxy)ethylcarbamyl, aziridinyl, allyloxycarbonyloxy, epoxy, carboxylic acid, carboxylic ester, acryloylamino, methacryloylamino, aminocarbonyl, $C_1$-$C_{18}$ alkyl aminocarbonyl, aminocarbonyl($C_1$-$C_{18}$)alkyl, $C_1$-$C_{18}$ alkyloxycarbonyloxy, halocarbonyl, hydrogen, aryl, hydroxy($C_1$-$C_{18}$)alkyl, $C_1$-$C_{18}$ alkyl, $C_1$-$C_{18}$ alkoxy, amino($C_1$-$C_{18}$)alkyl, $C_1$-$C_{18}$ alkylamino, di-($C_1$-$C_{18}$)alkylamino, $C_1$-$C_{18}$ alkyl($C_1$-$C_{18}$) alkoxy, $C_1$-$C_{18}$ alkoxy($C_1$-$C_{18}$)alkoxy, nitro, poly($C_1$-$C_{18}$)alkyl ether, ($C_1$-$C_{18}$)alkyl($C_1$-$C_{18}$)alkoxy($C_1$-$C_{18}$) alkyl, polyethyleneoxy, polypropyleneoxy, ethylene, acryloyl, acryloyloxy($C_1$-$C_{18}$)alkyl, methacryloyl, methacryloyloxy($C_1$-$C_{18}$)alkyl, 2-chloroacryloyl, 2-phenylacryloyl, acryloyloxyphenyl, 2-chloroacryloylamino, 2-phenylacryloylaminocarbonyl, oxetanyl, glycidyl, cyano, isocyanato($C_1$-$C_{18}$)alkyl, itaconic acid ester, vinyl ether, vinyl ester, a styrene derivative, main-chain and side-chain liquid crystal polymers, siloxane derivatives, ethyleneimine derivatives, maleic acid derivatives, maleimide derivatives, fumaric acid derivatives, unsubstituted cinnamic acid derivatives, cinnamic acid derivatives that are substituted with at least one of methyl, methoxy, cyano and halogen, and substituted or unsubstituted chiral or non-chiral monovalent or divalent groups chosen from steroid radicals, terpenoid radicals, alkaloid radicals and mixtures thereof, wherein the substituents are independently chosen from $C_1$-$C_{18}$ alkyl, $C_1$-$C_{18}$ alkoxy, amino, $C_3$-$C_{10}$ cycloalkyl, $C_1$-$C_{18}$ alkyl($C_1$-$C_{18}$)alkoxy, fluoro($C_1$-$C_{18}$)cyano, cyano($C_1$-$C_{18}$)alkyl, cyano($C_1$-$C_{18}$)alkoxy or mixtures thereof, or P is a structure having from 2 to 4 reactive groups, or P is an unsubstituted or substituted ring opening metathesis polymerization precursor, or P is a substituted or unsubstituted photochromic compound; and
(d) d' is chosen from 1, 2, 3, and 4, and
e' and f' are each independently chosen from 0, 1, 2, 3, and 4,
provided that a sum of d'+e'+f' is at least 2.
2. The naphthopyran compound of claim 1 wherein,
$R_1$ for each q is independently chosen from:
a reactive substituent; a compatiblizing substituent; hydrogen; fluoro; chloro; $C_1$-$C_6$ alkyl; $C_3$-$C_7$ cycloalkyl; substituted or unsubstituted phenyl; —$OR_{10'}$ or —OC(=O)$R_{10'}$, wherein $R_{10'}$ is hydrogen, $C_1$-$C_6$ alkyl, phenyl($C_1$-$C_3$)alkyl, mono($C_1$-$C_6$) alkyl substituted phenyl($C_1$-$C_3$)alkyl, mono($C_1$-$C_6$) alkoxy substituted phenyl($C_1$-$C_3$)alkyl, ($C_1$-$C_6$) alkoxy($C_2$-$C_4$)alkyl, $C_3$-$C_7$ cycloalkyl, or mono($C_1$-$C_4$)alkyl substituted $C_3$-$C_7$ cycloalkyl, and said phenyl substituents being hydroxyl, halogen, carbonyl, $C_1$-$C_6$ alkoxycarbonyl, cyano, halo($C_1$-$C_6$)alkyl, $C_1$-$C_6$ alkyl or $C_1$-$C_6$ alkoxy; —N($R_{11'}$)$R_{12'}$, wherein $R_{11'}$ and $R_{12'}$ are each independently hydrogen, $C_1$-$C_8$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$-$C_8$ alkylaryl, $C_3$-$C_{20}$ cycloalkyl, $C_4$-$C_{20}$ bicycloalkyl, $C_5$-$C_{20}$ tricycloalkyl or $C_1$-$C_{20}$ alkoxyalkyl, wherein said aryl group is phenyl or naphthyl, or $R_{11'}$ and $R_{12'}$ come together with the nitrogen atom to form a $C_3$-$C_{20}$ hetero-bicycloalkyl ring or a $C_4$-$C_{20}$ hetero-tricycloalkyl ring; a nitrogen containing ring represented by the following graphic formula VA:

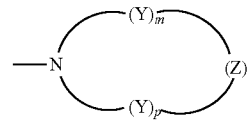

VA wherein each —Y— is independently chosen for each occurrence from —$CH_2$—, —CH($R_{13'}$)—, —C($R_{13'}$)$_2$—, —CH(aryl)-, —C(aryl)$_2$-, and —C($R_{13'}$)(aryl)-, and Z is —Y—, —O—, —S—, —S(O)—, —$SO_2$—, —NH—, —N($R_{13'}$)—, or —N(aryl)-, wherein each $R_{13}$' is independently $C_1$-$C_6$ alkyl, each aryl is independently phenyl or naphthyl, p is an integer 1, 2 or 3, and m is an integer 0, 1, 2, or 3 and provided that when m is 0, Z is —Y—; a group represented by one of the following graphic formulae VB or VC:

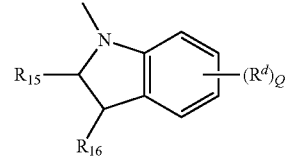

VB

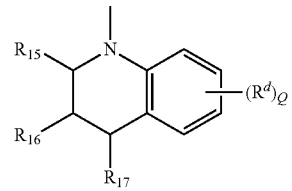

VC wherein $R_{15}$, $R_{16}$, and $R_{17}$ are each independently hydrogen, $C_1$-$C_6$ alkyl, phenyl, or naphthyl, or the groups $R_{15}$ and $R_{16}$ together form a ring of 5 to 8 carbon atoms and each $R^d$ is independently for each occurrence selected from $C_1$-$C_6$ alkyl, $C_1$-$C_6$ alkoxy, fluoro or chloro, and Q is an integer 0, 1, 2, or 3; and unsubstituted, mono-, or di-substituted $C_4$-$C_{18}$ spirobicyclic amine, or unsubstituted, mono-, and di-substituted $C_4$-$C_{18}$ spirotricyclic amine, wherein said substituents are independently aryl, $C_1$-$C_6$ alkyl, $C_1$-$C_6$ alkoxy, or phenyl($C_1$-$C_6$)alkyl; or two adjacent $R^1$ groups as Position-7 and Position-8 together form a group represented by one of VD and VE:

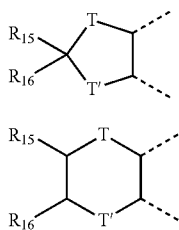

(VD)

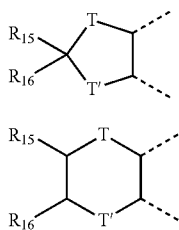

(VE)

wherein T and T' are each independently oxygen or the group —NR$_{11'}$—, where R$_{11'}$, R$_{15}$, and R$_{16}$ are as set forth above, provided that at least one R$_1$ is said group L;

R$_2$, R$_3$, R$_4$, and R$_5$, are each independently chosen in each case from hydrogen, linear or branched C$_1$-C$_{20}$ alkyl, C$_3$-C$_7$ cycloalkyl, unsubstituted aryl, and substituted aryl, where said aryl substituents are selected from at least one of hydroxyl, halogen, cyano, hydrocarbyl, substituted hydrocarbyl, alkoxy, and —N(R$_9$)R$_{10}$, or R$_2$ and R$_3$ together form an optionally substituted C$_5$-C$_8$ cyclic ring, or R$_4$ and R$_5$ together form an optionally substituted C$_5$-C$_8$ cyclic ring;

B and B' are each independently:

an aryl group that is mono-substituted with a reactive substituent or a compatiblizing substituent; a substituted phenyl; a substituted aryl; a substituted 9-julolindinyl; a substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl, wherein the phenyl, aryl, 9-julolindinyl, or heteroaromatic substituent is the reactive substituent R; an unsubstituted, mono-, di-, or tri-substituted phenyl or aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl, wherein each of the phenyl, aryl and heteroaromatic substituents are each independently:

hydroxyl, a group —C(=O)R$_{21}$, wherein R$_{21}$ is —OR$_{22}$, —N(R$_{23}$)R$_{24}$, piperidino, or morpholino, wherein R$_{22}$ is allyl, C$_1$-C$_6$ alkyl, phenyl, mono(C$_1$-C$_6$)alkyl substituted phenyl, mono(C$_1$-C$_6$)alkoxy substituted phenyl, phenyl(C$_1$-C$_3$)alkyl, mono(C$_1$-C$_6$)alkyl substituted phenyl(C$_1$-C$_3$)alkyl, mono(C$_1$-C$_6$)alkoxy substituted phenyl(C$_1$-C$_3$)alkyl, C$_1$-C$_6$ alkoxy(C$_2$-C$_4$)alkyl or C$_1$-C$_6$ haloalkyl, R$_{23}$ and R$_{24}$ are each independently C$_1$-C$_6$ alkyl, C$_5$-C$_7$ cycloalkyl, phenyl or substituted phenyl, the phenyl substituents being C$_1$-C$_6$ alkyl or C$_1$-C$_6$ alkoxy, and said halo substituent is chloro or fluoro, aryl, mono(C$_1$-C$_{12}$)alkoxyaryl, di(C$_1$-C$_{12}$)alkoxyaryl, mono (C$_1$-C$_{12}$)alkylaryl, di(C$_1$-C$_{12}$)alkylaryl, haloaryl, C$_3$-C$_7$ cycloalkylaryl, C$_3$-C$_7$ cycloalkyl, C$_3$-C$_7$ cycloalkyloxy, C$_3$-C$_7$ cycloalkyloxy(C$_1$-C$_{12}$)alkyl, C$_3$-C$_7$ cycloalkyloxy(C$_1$-C$_{12}$)alkoxy, aryl(C$_1$-C$_{12}$)alkyl, aryl(C$_1$-C$_{12}$)alkoxy, aryloxy, aryloxy(C$_1$-C$_{12}$)alkyl, aryloxy(C$_1$-C$_{12}$)alkoxy, mono- or di(C$_1$-C$_{12}$)alkylaryl(C$_1$-C$_{12}$)alkyl, mono- or di-(C$_1$-C$_{12}$)alkoxyaryl(C$_1$-C$_{12}$)alkyl, mono- or di-(C$_1$-C$_{12}$)alkylaryl(C$_1$-C$_{12}$)alkoxy, mono- or di-(C$_1$-C$_{12}$)alkoxyaryl(C$_1$-C$_{12}$)alkoxy, amino, mono- or di-(C$_1$-C$_{12}$)alkylamino, diarylamino, piperazino, N—(C$_1$-C$_{12}$)alkylpiperazino, N-arylpiperazino, aziridino, indolino, piperidino, morpholino, thiomorpholino, tetrahydroquinolino, tetrahydroisoquinolino, pyrrolidyl, C$_1$-C$_{12}$ alkyl, C$_1$-C$_{12}$ haloalkyl, C$_1$-C$_{12}$ alkoxy, mono(C$_1$-C$_{12}$)alkoxy(C$_1$-C$_{12}$)alkyl, acryloxy, methacryloxy, or halogen;

an unsubstituted or mono-substituted group chosen from pyrazolyl, imidazolyl, pyrazolinyl, imidazolinyl, pyrrolinyl, phenothiazinyl, phenoxazinyl, phenazinyl, and acridinyl, each of said substituents being C$_1$-C$_{12}$ alkyl, C$_1$-C$_{12}$ alkoxy, phenyl, or halogen;

a group represented by one of:

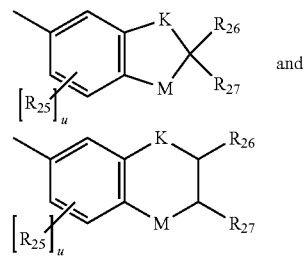

wherein K is —CH$_2$— or —O—, and M is —O— or substituted nitrogen, provided that when M is substituted nitrogen, K is —CH$_2$—, the substituted nitrogen substituents being hydrogen, C$_1$-C$_{12}$ alkyl, or C$_1$-C$_{12}$ acyl, each R$_{25}$ being independently chosen for each occurrence from C$_1$-C$_{12}$ alkyl, C$_1$-C$_{12}$ alkoxy, hydroxy, and halogen, R$_{26}$ and R$_{27}$ each being independently hydrogen or C$_1$-C$_{12}$ alkyl, and u is an integer ranging from 0 to 2; or a group represented by:

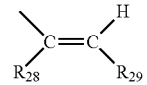

wherein R$_{28}$ is hydrogen or C$_1$-C$_{12}$ alkyl, and R$_{29}$ is an unsubstituted, mono-, or di-substituted group chosen from naphthyl, phenyl, furanyl, and thienyl, wherein the substituents are C$_1$-C$_{12}$ alkyl, C$_1$-C$_{12}$ alkoxy, or halogen; or B and B' taken together form one of a fluoren-9-ylidene, mono-, or di-substituted fluoren-9-ylidene, each of said fluoren-9-ylidene substituents being independently chosen from C$_1$-C$_{12}$ alkyl, C$_1$-C$_{12}$ alkoxy, and halogen;

wherein for said group L represented by Formula (IV), (a) Q$_1$, Q$_2$, and Q$_3$ for each occurrence, are independently selected from optionally substituted aryl and optionally substituted cycloalkyl, (b) each S$_1$, S$_2$, S$_3$, S$_4$, and S$_5$ is independently chosen for each occurrence from a spacer unit selected from, (ii) —N(Z)—, —C(Z)=C(Z)—, —C(Z)=N—, —C(Z')$_2$—C(Z')$_2$—, and a single bond, wherein Z for each occurrence is independently selected from hydrogen, C$_1$-C$_8$ alkyl, C$_3$-C$_6$ cycloalkyl and aryl, and Z' for each occurrence is independently selected from C$_1$-C$_8$ alkyl, C$_3$-C$_6$ cycloalkyl and aryl, and (iii) —O—, —C(=O)—, —N=N—, —S—, —S(=O)—, and straight-chain or branched C$_1$-C$_{12}$ alkylene residue, said C$_1$-C$_{12}$ alkylene residue being unsubstituted, mono-substituted by cyano or halogen, or poly-substituted by halogen, and (c) P for each occurrence is independently selected from hydrogen, hydroxy, amino, C$_2$-C$_8$ alkenyl, C$_2$-C$_8$ alkynyl, acryloyloxy, methacryloyloxy, 2-(acryloyloxy)ethylcarbamyl, 2-(methacryloyloxy)ethylcarbamyl, epoxy, carboxylic acid, carboxylic ester, acryloylamino, methacryloylamino, aminocarbonyl, C$_1$-C$_8$ alkyl aminocarbonyl, aminocarbonyl($C_1$-$C_8$)alkyl, $C_1$-$C_8$ alkyloxycarbonyloxy, halocarbonyl, aryl, hydroxy($C_1$-$C_8$)alkyl, $C_1$-$C_8$ alkyl, $C_1$-$C_8$ alkoxy, amino($C_1$-$C_8$)alkyl, $C_1$-$C_8$ alkylamino, di-($C_1$-$C_8$)alkylamino, $C_1$-$C_8$ alkyl($C_1$-$C_8$) alkoxy, $C_1$-$C_8$ alkoxy($C_1$-$C_8$)alkoxy, nitro, poly($C_1$-$C_8$) alkyl ether, ($C_1$-$C_8$)alkyl($C_1$-$C_8$)alkoxy($C_1$-$C_8$)alkyl, polyethyleneoxy, polypropyleneoxy, ethylene, acryloyl, acryloyloxy($C_1$-$C_{18}$)alkyl, methacryloyl, methacryloyloxy($C_1$-$C_8$)alkyl, 2-chloroacryloyl, 2-phenylacryloyl, acryloyloxyphenyl, 2-chloroacryloylamino, 2-phenylacryloylaminocarbonyl, oxetanyl, glycidyl, cyano, isocyanato($C_1$-$C_{18}$)alkyl, itaconic acid ester, vinyl ether, and vinyl ester.

3. The naphthopyran compound of claim 2 wherein,
$R_1$, independently for each q, is selected from hydrogen, linear or branched $C_1$-$C_6$ alkyl, and said group L, provided that at least one $R_1$ is said group L;
$R_2$, $R_3$, $R_4$, and $R_5$, are each independently chosen in each case from hydrogen, linear or branched $C_1$-$C_6$ alkyl, $C_3$-$C_7$ cycloalkyl, unsubstituted phenyl, and substituted phenyl, where said phenyl substituents are selected from at least one of hydroxyl, halogen, and cyano, linear or branched $C_1$-$C_{10}$ alkyl, linear or branched $C_1$-$C_{10}$ alkoxy, and —N($R_9$)$R_{10}$, wherein $R_9$ and $R_{10}$ are each independently selected from hydrogen and linear or branched $C_1$-$C_{10}$ alkyl,
  or $R_2$ and $R_3$ together form an optionally substituted $C_5$-$C_6$ cyclic ring optionally having one ethylenically unsaturated group in the cyclic ring,
  or $R_4$ and $R_5$ together form an optionally substituted $C_5$-$C_6$ cyclic ring optionally having one ethylenically unsaturated group in the cyclic ring;
B and B' are each independently selected from aryl, aryl substituted with $C_1$-$C_6$ alkoxy, aryl substituted with halogen, aryl substituted with morpholino, and aryl substituted with piperidinyl;
wherein for said group L represented by Formula (IV),
(b) each $S_1$, $S_2$, $S_3$, $S_4$, and $S_5$ is independently chosen for each occurrence from a spacer unit selected from,
  (ii) —N(Z)—, —C(Z)═C(Z)—, and a single bond, wherein Z for each occurrence is independently selected from hydrogen, $C_1$-$C_8$ alkyl, $C_3$-$C_6$ cycloalkyl and aryl, and Z' for each occurrence is independently selected from $C_1$-$C_8$ alkyl, $C_3$-$C_6$ cycloalkyl and aryl, and
  (iii) —O—, —C(═O)—, —C≡C—, and straight-chain or branched $C_1$-$C_6$ alkylene residue, said $C_1$-$C_6$ alkylene residue being unsubstituted, mono-substituted by cyano or halogen, or poly-substituted by halogen, and
(c) P for each occurrence is independently selected from hydrogen, hydroxy, amino, $C_2$-$C_8$ alkenyl, $C_2$-$C_8$ alkynyl, and aryl.

4. The naphthopyran compound of claim 3 wherein,
$R_1$, independently for each q, is selected from hydrogen, linear or branched $C_1$-$C_6$ alkyl, and said group L, provided that one $R_1$ is said group L, and said group L is bonded to Position-8; and
B and B' are each independently selected from phenyl, phenyl substituted with $C_1$-$C_6$ alkoxy, phenyl substituted with halogen, phenyl substituted with morpholino, and phenyl substituted with piperidinyl.

5. The naphthopyran compound of claim 3 wherein,
said group L is in each case independently selected from,

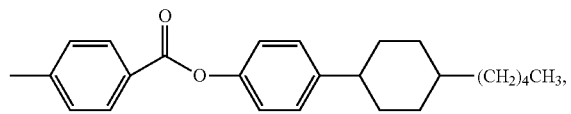

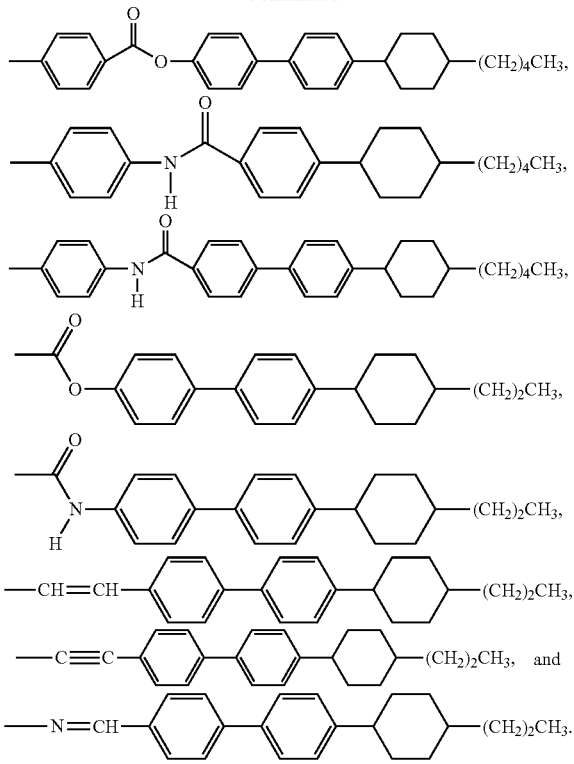

6. The naphthopyran compound of claim 1, wherein said naphthopyran compound is selected from the group consisting of,
  2-(4-morpholinophenyl)-2-phenyl-9-(4-(4-(4-pentylcyclohexyl)phenyloxycarbonyl)phenyl)-2,5-dihydro-7-oxo-furo[3',4':3,4]naphtho[1,2-b]pyran
  2-(4-morpholinophenyl)-2,5,5-triphenyl-9-(4-(4-(4-pentylcyclohexyl)phenyloxycarbonyl)phenyl)-2,5-dihydro-7-oxo-furo[3',4':3,4]naphtho[1,2-b]pyran
  5,5-dimethyl-2-(4-morpholinophenyl)-2-phenyl-9-(4-(4-(4-pentylcyclohexyl)phenyloxycarbonyl)phenyl)-2,5-dihydro-7-oxo-furo[3',4':3,4]naphtho[1,2-b]pyran
  2-(4-morpholinophenyl)-2-phenyl-9-(4-(4-(4-pentylcyclohexyl)phenyloxycarbonyl)phenyl)-2,5-dihydro-7-oxo-spiro[cyclopent[3]ene-1',5-furo[3',4':3,4]naphtho[1,2-b]pyran
  2-(4-morpholinophenyl)-2-phenyl-9-(4-(4-(4-pentylcyclohexyl)phenyloxycarbonyl)phenyl)-2,5-dihydro-5-oxo-spiro[cyclopent[3]ene-1',7-furo[3',4':3,4]naphtho[1,2-b]pyran
  5,5-dimethyl-2-(2-fluorophenyl)-2-(4-morpholinophenyl)-9-(4-(4-(4-pentylcyclohexyl)phenyloxycarbonyl)phenyl)-2,5-dihydro-7-oxo-furo[3',4':3,4]naphtho[1,2-b]pyran
  5,5-dimethyl-2-(2-fluorophenyl)-2-(4-morpholinophenyl)-9-(4-(4'(4-pentylcyclohexyl)-[1,1'-biphenyl]-4-yl-carboxamido)phenyl)-2,5-dihydro-7-oxo-furo[3',4':3,4]naphtho[1,2-b]pyran
  5,5-dimethyl-2-(4-morpholinophenyl)-2-phenyl-9-(4-(4-(4-pentylcyclohexyl)phenyloxycarbonyl)phenyl)-2,5,7-trihydro-furo[3',4':3,4]naphtho[1,2-b]pyran
  5,5-dimethyl-2-(4-fluorophenyl)-2-(4-morpholinophenyl)-9-(4-(4-(4-pentylcyclohexyl)phenyloxycarbonyl)phenyl)-2,5,7-trihydro-furo[3',4':3,4]naphtho[1,2-b]pyran
  5,5-dimethyl-2,2-di-(methoxyphenyl)-9-(4-(4-(4-pentylcyclohexyl)phenyloxycarbonyl)phenyl)-2,5,7-trihydro-furo[3',4':3,4]naphtho[1,2-b]pyran 5,5-dimethyl-2-(methoxyphenyl)-2-(4-morpholinophenyl)-9-(4-(4-(4-pentylcyclohexyl)phenyloxycarbonyl)phenyl)-2,5,7-trihydro-furo[3',4':3,4]naphtho[1,2-b]pyran, and 5,5-diethyl-2-(4-morpholinophenyl)-2-phenyl-9-(4-(4-(4-pentylcyclohexyl)phenyloxycarbonyl)phenyl)-2,5,7-trihydro-furo[3',4':3,4]naphtho[1,2-b]pyran.

7. The naphthopyran compound of claim 1, wherein said naphthopyran compound is a photochromic-dichroic naphthopyran compound.

8. A photochromic-dichroic article comprising said photochromic-dichroic naphthopyran compound of claim 7.

9. The photochromic-dichroic article of claim 8, wherein said photochromic-dichroic article is selected from ophthalmic articles, display articles, windows, mirrors, and active liquid crystal cell articles, and passive liquid crystal cell articles.

10. The photochromic-dichroic article of claim 9, wherein said photochromic-dichroic article is selected from ophthalmic articles, the ophthalmic articles being selected from corrective lenses, non-corrective lenses, contact lenses, intraocular lenses, magnifying lenses, protective lenses, and visors.

11. The photochromic-dichroic article of claim 9, wherein said photochromic-dichroic article is selected from display articles, the display articles being selected from screens, monitors, and security elements.

* * * * *